(12) United States Patent
Conner

(10) Patent No.: US 8,980,282 B2
(45) Date of Patent: Mar. 17, 2015

(54) VIRUSES

(75) Inventor: Joe Conner, Glasgow (GB)

(73) Assignee: Virttu Biologics Limited, Glasgow (GB)

( * ) Notice: Subject to any disclaimer, the term of this patent is extended or adjusted under 35 U.S.C. 154(b) by 1222 days.

(21) Appl. No.: 12/670,551

(22) PCT Filed: Apr. 2, 2008

(86) PCT No.: PCT/GB2008/001156
§ 371 (c)(1),
(2), (4) Date: Jul. 6, 2010

(87) PCT Pub. No.: WO2009/013448
PCT Pub. Date: Jan. 29, 2009

(65) Prior Publication Data
US 2010/0272691 A1    Oct. 28, 2010

(30) Foreign Application Priority Data

Jul. 26, 2007  (GB) .................................. 0714578.2

(51) Int. Cl.
*C12N 7/00* (2006.01)
*A01N 63/00* (2006.01)
*A61K 47/48* (2006.01)

(52) U.S. Cl.
CPC ..... *A61K 47/48776* (2013.01); *A61K 47/48561* (2013.01); *A61K 47/48623* (2013.01); *A61K 47/48638* (2013.01)
USPC ...................................... 424/235.1; 424/93.6

(58) Field of Classification Search
None
See application file for complete search history.

(56) References Cited

U.S. PATENT DOCUMENTS

2007/0110720 A1 *  5/2007  Brown et al. ................ 424/93.2

FOREIGN PATENT DOCUMENTS

| WO | WO 03/068809 A2 | 8/2003 |
|---|---|---|
| WO | WO 2005/005637 A2 | 1/2005 |
| WO | WO 2007/027774 A1 | 3/2007 |

OTHER PUBLICATIONS

Cocchi et al. (May 2004) PNAS, 101(19):7445-7450, "The soluble ectodomain of herpes simplex virus gD contains a membrane-proximal pro-fusion domain and suffices to mediate virus entry".
Connolly et al. (Jul. 2003) Journal of Virology, 77(14):8127-8140, "Structure-Based Mutagenesis of Herpes Simplex Virus Glycoprotein D Defines Three Critical Regions at the gD-HveA/HVEM Binding Interface".
Fusco et al. (Jun. 2005) PNAS, 102(26):9323-9328, "The pro-fusion domain of herpes simplex virus glycoprotein D (gD) interacts with the gD N terminus and is displaced by soluble forms of viral receptors".
Menotti et al. (Jun. 2006) Journal of Virology, 80(11):5531-5539, "A Herpes Simplex Virus Recombinant That Exhibits a Single-Chain Antibody to HER2/neu Enters Cells through the Mammary Tumor Receptor, Independently of the gD Receptors".
Nakano et al. (Apr. 2005) Molecular Therapy, 11(4):617-626, "Herpes Simplex Virus Targeting to the EGF Receptor by a gD-Specific Soluble Bridging Molecule".
Reske et al. (2007) Reviews in Medical Virology, 17:205-215, "Understanding HSV-1 entry glycoproteins".
Spear et al. (2006) Virology, 344:17-24, "Different receptors binding to distinct interfaces on herpes simplex virus gD can trigger events leading to cell fusion and viral entry".
Zhou et al. (Nov. 2002) PNAS, 99(23):15124-15129, "Engineered herpes simplex virus 1 is dependent on IL13R$\alpha$2 receptor for cell entry and independent of glycoprotein D receptor interaction".
Zhou et al. (Apr. 2006) PNAS, 103(14):5508-5513, "Construction and properties of a herpes simplex virus 1 designed to enter cells solely via the IL-13$\alpha$2 receptor".

* cited by examiner

*Primary Examiner* — Michael Burkhart
(74) *Attorney, Agent, or Firm* — Swanson & Bratschun, L.L.C.

(57) ABSTRACT

Herpes Simplex Viruses are disclosed having single-chain antibodies (scFv) embedded in the viral envelope via fusion with glycoprotein D and with glycoprotein H and L.

12 Claims, 24 Drawing Sheets

MGGAAARLGAVILFVVIVGLHGVRSKYALVDASLKMADPNRFRG
KDLPVLDQLTDPPGVRRVYHIQAGLPDPFQPPSLPITVYYAVLERACRSVLLNAPSEA
PQIVRGASEDVRKQPYNLTIAWFRMGGNCAIPITVMEYTECSYNKSLGACPIRTQPRW
NYYDSFSAVSEDNLGFLMHAPAFETAGTYLRLVKINDWTEITQFILEHRAKGSCKYAL
PLRIPPSACLSPQAYQQGVTVDSIGMLPRFIPENQRTVAVYSLKIAGWHGPKAPYTST
LLPPELSETPNATQPELAPEDPEDSALLEDPVGTVAPQIPPNWHIPSIQDAATPYHPP
ATPNNMGLIAGAVGGSLLAALVICGIVYWMRRHTQKAPKRIRLPHIREDDQPSSHQPL
FY

Figure 21a

MGNGLWFVGVIILGVAWGQVHDWTEQTDPWFLDGLGMDRMYWRD
TNTGRLWLPNTPDPQKPPRGFLAPPDELNLTTASLPLLRWYEERFCFVLVTTAEFPRD
PGQLLYIPKTYLLGRPPNASLPAPTTVEPTAQPPPSVAPLKGLLHNPAASVLLRSRAW
VTFSAVPDPEALTFPRGDNVATASHPSGPRDTPPPRPPVGARRHPTTELDITHLHNAS
TTWLATRGLLRSPGRYVYFSPSASTWPVGIWTTGELVLGCDAALVRARYGREFMGLVI
SMHDSPPVEVMVVPAGQTLDRVGDPADENPPGALPGPPGGPRYRVFVLGSLTRADNGS
ALDALRRVGGYPEEGTNYAQFLSRAYAEFFSGDAGAEQGPRPPLFWRLTGLLATSGFA
FVNAAHANGAVCLSDLLGFLAHSRALAGLAARGAAGCAADSVFFNVSVLDPTARLQLE
ARLQHLVAEILEREQSLALHALGYQLAFVLDSPSAYDAVAPSAAHLIDALYAEFLGGR
VLTTPVVHRALFYASAVLRQPFLAGVPSAVQRERARRSLLIASALCTSDVAAATNADL
RTALARADHQKTLFWLPDHFSPCAASLRFDLDESVFILDALAQATRSETPVEVLAQQT
HGLASTLTRWAHYNALIRAFVPEASHRCGGQSANVEPRILVPITHNASYVVTHSPLPR
GIGYKLTGVDVRRPLFLTYLTATCEGSTRDIESKRLVRTQNQRDLGLVGAVFMRYTPA
GEVMSVLLVDTDNTQQQIAAGPTEGAPSVFSSDVPSTALLLFPNGTVIHLLAFDTQPV
AAIAPGFLAASALGVVMITAALAGILKVLRTSVPFFWRRE

Figure 21b

MGILGWVGLIAVGVLCVRGGLPSTEYVIRSRVAREVGDILKVPC
VPLPSDDLDWRYETPSAINYALIDGIFLRYHCPGLDTVLWDRHAQKAYWVNPFLFVAG
FLEDLSYPAFPANTQETETRLALYKEIRQALDSRKQAASHTPVKAGCVNFDYSRTRRC
VGRQDLGPTNGTSGRTPVLPPDDEAGLQPKPLTTPPPIIATSDPTPRRDAATKSRRRR
PHSRRL

Figure 21c

```
                                                                          at
138421 gggggggggct gccgccaggt tggggggccgt gattttgttt gtcgtcatag tgggcctcca
138481 tggggtccgc agcaaatatg ccttggtgga tgcctctctc aagatggccg accccaatcg
138541 ctttcgcggc aaagaccttc cggtcctgga ccagctgacc gaccctccgg gggtccggcg
138601 cgtgtaccac atccaggcgg gcctaccgga cccgttccag ccccccagcc tcccgatcac
138661 ggtttactac gccgtgttgg agcgcgcctg ccgcagcgtg ctcctaaacg caccgtcgga
138721 ggcccccccag attgtccgcg gggcctccga agacgtccgg aaacaaccct acaacctgac
138781 catcgcttgg tttcggatgg gaggcaactg tgctatcccc atcacggtca tggagtacac
138841 cgaatgctcc tacaacaagt ctctgggggc ctgtcccatc cgaacggcagc cccgctggaa
138901 ctactatgac agcttcagcg ccgtcagcga ggataacctg gggttcctga tgcacgcccc
138961 cgcgtttgag accgccggca cgtacctgcg gctcgtgaag ataaacgact ggacggagat
139021 tacacagttt atcctggagc accgagccaa gggctcctgt aagtacgccc tcccgctgcg
139081 catcccccccg tcagcctgcc tctccccccca ggcctaccag caggggggtga cggtggacag
139141 catcgggatg ctgccccgct tcatccccga gaaccagcgc accgtcgccg tatacagctt
139201 gaagatcgcc gggtggcacg ggcccaaggc cccatacacg agcaccctgc tgccccccgga
139261 gctgtccgag acccccaacg ccacgcagcc agaactcgcc ccggaagacc ccgaggattc
139321 ggccctcttg gaggaccccg tggggacggt ggcgccgcaa atcccaccaa actggcacat
139381 accgtcgatc caggacgccc cgacgcctta ccatccccg gccaccccga acaaacatggg
139441 cctgatcgcc ggcgcggtgg gcggcagtct cctggcagcc ctggtcattt gcggaattgt
139501 gtactggatg cgccgccaca ctcaaaaagc cccaaagcgc atacgcctcc cccacatccg
139561 ggaagacgac cagccgtcct cgcaccagcc cttgttttac tag
```

Figure 21d

```
                ttatt cgcgtctcca aaaaaacggg acacttgtcc ggagaacctt taggatgcca
43921 gccagggcgg cggtaatcat aaccacgccc agcgcagagg cggccagaaa cccgggcgca
43981 attgcggcca cgggctgcgt gtcaaaggct agcaaatgaa tgacggttcc gtttggaaat
44041 agcaacaagg ccgtggacgg cacgtcgctc gaaaacacgc ttggggcgcc ctccgtcggc
44101 ccggcggcga tttgctgctg tgtgttgtcc gtatccacca gcaacacaga catgacctcc
44161 ccggccgggg tgtagcgcat aaacacggcc cccacgagcc ccaggtcgcg ctggttttgg
44221 gtgcgcacca gccgcttgga ctcgatatcc cgggtggagc cttcgcatgt cgcggtgagg
44281 taggttagga acagtgggcg tcggacgtcg acgccggtga gcttgtagcc gatccccgg
44341 ggcagagggg agtgggtgac gacgtagctg gcgttgtggg tgatgggtac caggatccgt
44401 ggctcgacgt tggcagactg cccccgcac cgatgtgagg cctcagggac gaaggcgcgg
44461 atcagggcgt tgtagtgtgc ccaacgcgtc agggtcgagg cgaggccgtg ggtctgctgg
44521 gccaggactt cgaccggggt ctcggatcgg gtggcttgag ccagcgcgtc caggataaac
44581 acgctctcgt ctagatcaaa gcgcagggag gccgccatg gcgaaaagtg gtccggaagc
44641 caaaagaggg ttttctggtg gtcggcccgg gccagcgcgg tccggaggtc ggcgttggtc
44701 gctgcggcga cgtcggacgt acacagggcc gaggctatca gaaggctccg gcgggcgcgt
44761 tcccgctgca ccgccgaggg gacgccagcc aagaacggct gccggaggac agccgaggcg
44821 taaaatagcg cccggtggac gaccggggtg gtcagcacgc ggcccctag aaactcggca
44881 tacagggcgt cgatgagatg ggctgcgctg ggcgccactg cgtcgtacgc cgaggggcta
44941 tccagcacga aggccagctg atagcccagc gcgtgtaatg ccaagctctg ttcgcgctcc
45001 agaatctcgg ccaccaggtg ctggagccga gcctctagct gcaggcgggc cgtgggatcc
45061 aagactgaca cattaaaaaa cacagaatcc gcggcacagc ccgcggcccc gcgggcggcc
45121 aacccggcaa gcgcgcgcga gtgggccaaa aagcctagca ggtcggagag gcagaccgcg
45181 ccgtttgcgt gggcggcgtt cacgaaagca aaacccgacg tcgcgagcag ccccgttagg
45241 cgccagaaga gaggggggcc cgggccctgc tcggccccga cgtcccccga gaaaaactcc
45301 gcgtatgccc gcgacaggaa ctggccgtag ttcgtgccct cctccgggta gccgcccacg
45361 cggcggaggg cgtccagcgc ggagccgttg tcggcccgcg tcagggaccc taggacaaag
45421 acccgatacc ggggccgcc cggggcccg ggaagagccc ccgggggtt ttcgtccgcg
45481 gggtccccga cccgatctag cgtctggccc gcggggacca ccatcacttc caccggaggg
45541 ctgtcgtgca tggatatcac gagcccatg aattcccgcc cgtagcgcgc gcgcaccagc
45601 gcggcatcgc acccgagcac cagctccccc gtcgtccaga tgcccacggg ccacgtcgag
45661 gccgacgggg agaaatacac gtacctacct ggggatctca acaggccccg ggtggccaac
45721 caggtcgtgg acgcgttgtg caggtgcgtg atgtccagct ccgtcgtcgg gtgccgccgg
45781 gccccaaccg gcggtcgggg gggcggtgta tcacgcggcc cgctcgggtg gctcgccgtc
45841 gccacgttgt ctccccgcgg gaacgtcagg gcctcgggt cagggacggc cgaaaacgtt
45901 acccaggccc gggaacgcag caacacggag gcgcgtggat tgtgcaagag accccttaagg
45961 ggggcgaccg aggggggagg ctgggcggtc ggctcgaccg tggtggggc gggcaggctc
46021 gcgttcgggg gccggccgag caggtaggtc ttcgggatgt aaagcagctg gccggggtcc
46081 cgcggaaact cggccgtggt gaccaataca aaacaaaagc gctcctcgta ccagcgaaga
46141 aggggcagag atgccgtagt caggtttagt tcgtccggcg gcgccagaaa tccgcgcggt
46201 ggtttttggg ggtcgggggt gtttggcagc cacagacgcc cggtgttcgt gtcgcgccag
46261 tacatgcggt ccatgcccag gccatccaaa aaccatgggt ctgtctgctc agtccagtcg
46321 tggacctgac cccacgcaac gcccaaaata ataaccccca cgaaccataa accattcccc
46381 at
```

Figure 21e

```
                                        atgg ggattttggg ttgggtcggg
9361 cttattgccg ttggggtttt gtgtgtgcgg ggggcttgc cttcaaccga atatgttatt
9421 cggagtcggg tggctcgaga ggtgggggat atattaaagg tgccttgtgt gccgctcccg
9481 tctgacgatc ttgattggcg ttacgagacc ccctcggcta taaactatgc tttgatagac
9541 ggtatatttt tgcgttatca ctgtcccgga ttggacacgg tcttgtggga taggcatgcc
9601 cagaaggcat attgggttaa cccctttta tttgtggcgg gttttttgga ggacttgagt
9661 taccccgcgt ttcctgccaa cacccaggaa acagaaacgc gcttggccct ttataaagag
9721 atacgccagg cgctggacag tcgcaagcag gccgccagcc acacacctgt gaaggctggg
9781 tgtgtgaact ttgactattc gcgcacccgc cgctgtgtag ggcgacagga tttgggacct
9841 accaacgaaa cgtctgacg gaccccggtt ctgccgcgg acgatgaagc gggcctgcag
9901 ccgaagcccc tcaccacgcc gccgcccatc atcgccacgt cggaccccac cccgcgacgg
9961 gacgccgcca caaaaagcag acgccgacga ccccactccc ggcgcctcta a
```

Figure 21f

SEQUENCE LISTING

```
<160> NUMBER OF SEQ ID NOS: 43

<210> SEQ ID NO 1
<211> LENGTH: 394
<212> TYPE: PRT
<213> ORGANISM: Human herpesvirus 1

<400> SEQUENCE: 1
```

| | | | | | | | | | | | | | | |
|---|---|---|---|---|---|---|---|---|---|---|---|---|---|---|
| Met | Gly | Gly | Ala | Ala | Ala | Arg | Leu | Gly | Ala | Val | Ile | Leu | Phe | Val | Val |
| 1 | | | | 5 | | | | | 10 | | | | | 15 | |

| Ile | Val | Gly | Leu | His | Gly | Val | Arg | Ser | Lys | Tyr | Ala | Leu | Val | Asp | Ala |
|  |  |  | 20 |  |  |  |  | 25 |  |  |  |  | 30 |  |  |

| Ser | Leu | Lys | Met | Ala | Asp | Pro | Asn | Arg | Phe | Arg | Gly | Lys | Asp | Leu | Pro |
|  |  | 35 |  |  |  |  | 40 |  |  |  |  | 45 |  |  |  |

| Val | Leu | Asp | Gln | Leu | Thr | Asp | Pro | Pro | Gly | Val | Arg | Arg | Val | Tyr | His |
|  | 50 |  |  |  |  | 55 |  |  |  |  | 60 |  |  |  |  |

| Ile | Gln | Ala | Gly | Leu | Pro | Asp | Pro | Phe | Gln | Pro | Pro | Ser | Leu | Pro | Ile |
| 65 |  |  |  |  | 70 |  |  |  |  | 75 |  |  |  |  | 80 |

| Thr | Val | Tyr | Tyr | Ala | Val | Leu | Glu | Arg | Ala | Cys | Arg | Ser | Val | Leu | Leu |
|  |  |  |  | 85 |  |  |  |  | 90 |  |  |  |  | 95 |  |

| Asn | Ala | Pro | Ser | Glu | Ala | Pro | Gln | Ile | Val | Arg | Gly | Ala | Ser | Glu | Asp |
|  |  |  | 100 |  |  |  |  | 105 |  |  |  |  | 110 |  |  |

| Val | Arg | Lys | Gln | Pro | Tyr | Asn | Leu | Thr | Ile | Ala | Trp | Phe | Arg | Met | Gly |
|  |  | 115 |  |  |  |  | 120 |  |  |  |  | 125 |  |  |  |

| Gly | Asn | Cys | Ala | Ile | Pro | Ile | Thr | Val | Met | Glu | Tyr | Thr | Glu | Cys | Ser |
| | 130 | | | | | 135 | | | | | 140 | | | | |

| Tyr | Asn | Lys | Ser | Leu | Gly | Ala | Cys | Pro | Ile | Arg | Thr | Gln | Pro | Arg | Trp |
| 145 | | | | | 150 | | | | | 155 | | | | | 160 |

| Asn | Tyr | Tyr | Asp | Ser | Phe | Ser | Ala | Val | Ser | Glu | Asp | Asn | Leu | Gly | Phe |
| | | | | 165 | | | | | 170 | | | | | 175 | |

| Leu | Met | His | Ala | Pro | Ala | Phe | Glu | Thr | Ala | Gly | Thr | Tyr | Leu | Arg | Leu |
| | | | 180 | | | | | 185 | | | | | 190 | | |

| Val | Lys | Ile | Asn | Asp | Trp | Thr | Glu | Ile | Thr | Gln | Phe | Ile | Leu | Glu | His |
| | | 195 | | | | | 200 | | | | | 205 | | | |

| Arg | Ala | Lys | Gly | Ser | Cys | Lys | Tyr | Ala | Leu | Pro | Leu | Arg | Ile | Pro | Pro |
| | 210 | | | | | 215 | | | | | 220 | | | | |

| Ser | Ala | Cys | Leu | Ser | Pro | Gln | Ala | Tyr | Gln | Gln | Gly | Val | Thr | Val | Asp |
| 225 | | | | | 230 | | | | | 235 | | | | | 240 |

| Ser | Ile | Gly | Met | Leu | Pro | Arg | Phe | Ile | Pro | Glu | Asn | Gln | Arg | Thr | Val |
| | | | | 245 | | | | | 250 | | | | | 255 | |

| Ala | Val | Tyr | Ser | Leu | Lys | Ile | Ala | Gly | Trp | His | Gly | Pro | Lys | Ala | Pro |
| | | | 260 | | | | | 265 | | | | | 270 | | |

| Tyr | Thr | Ser | Thr | Leu | Leu | Pro | Pro | Glu | Leu | Ser | Glu | Thr | Pro | Asn | Ala |
| | | 275 | | | | | 280 | | | | | 285 | | | |

| Thr | Gln | Pro | Glu | Leu | Ala | Pro | Glu | Asp | Pro | Glu | Asp | Ser | Ala | Leu | Leu |
| | 290 | | | | | 295 | | | | | 300 | | | | |

| Glu | Asp | Pro | Val | Gly | Thr | Val | Ala | Pro | Gln | Ile | Pro | Asn | Trp | His |
| 305 | | | | | 310 | | | | | 315 | | | | | 320 |

| Ile | Pro | Ser | Ile | Gln | Asp | Ala | Ala | Thr | Pro | Tyr | His | Pro | Pro | Ala | Thr |
| | | | | 325 | | | | | 330 | | | | | 335 | |

```
Pro Asn Asn Met Gly Leu Ile Ala Gly Ala Val Gly Gly Ser Leu Leu
                340                 345                 350

Ala Ala Leu Val Ile Cys Gly Ile Val Tyr Trp Met Arg Arg His Thr
        355                 360                 365

Gln Lys Ala Pro Lys Arg Ile Arg Leu Pro His Ile Arg Glu Asp Asp
370                 375                 380

Gln Pro Ser Ser His Gln Pro Leu Phe Tyr
385                 390

<210> SEQ ID NO 2
<211> LENGTH: 838
<212> TYPE: PRT
<213> ORGANISM: Human herpesvirus 1

<400> SEQUENCE: 2

Met Gly Asn Gly Leu Trp Phe Val Gly Val Ile Ile Leu Gly Val Ala
1               5                   10                  15

Trp Gly Gln Val His Asp Trp Thr Glu Gln Thr Asp Pro Trp Phe Leu
                20                  25                  30

Asp Gly Leu Gly Met Asp Arg Met Tyr Trp Arg Asp Thr Asn Thr Gly
            35                  40                  45

Arg Leu Trp Leu Pro Asn Thr Pro Asp Pro Gln Lys Pro Pro Arg Gly
    50                  55                  60

Phe Leu Ala Pro Pro Asp Glu Leu Asn Leu Thr Thr Ala Ser Leu Pro
65                  70                  75                  80

Leu Leu Arg Trp Tyr Glu Glu Arg Phe Cys Phe Val Leu Val Thr Thr
                85                  90                  95

Ala Glu Phe Pro Arg Asp Pro Gly Gln Leu Leu Tyr Ile Pro Lys Thr
            100                 105                 110

Tyr Leu Leu Gly Arg Pro Pro Asn Ala Ser Leu Pro Ala Pro Thr Thr
        115                 120                 125

Val Glu Pro Thr Ala Gln Pro Pro Ser Val Ala Pro Leu Lys Gly
130                 135                 140

Leu Leu His Asn Pro Ala Ala Ser Val Leu Leu Arg Ser Arg Ala Trp
145                 150                 155                 160

Val Thr Phe Ser Ala Val Pro Asp Pro Glu Ala Leu Thr Phe Pro Arg
                165                 170                 175

Gly Asp Asn Val Ala Thr Ala Ser His Pro Ser Gly Pro Arg Asp Thr
            180                 185                 190

Pro Pro Pro Arg Pro Pro Val Gly Ala Arg Arg His Pro Thr Thr Glu
        195                 200                 205

Leu Asp Ile Thr His Leu His Asn Ala Ser Thr Thr Trp Leu Ala Thr
210                 215                 220

Arg Gly Leu Leu Arg Ser Pro Gly Arg Tyr Val Tyr Phe Ser Pro Ser
225                 230                 235                 240

Ala Ser Thr Trp Pro Val Gly Ile Trp Thr Thr Gly Glu Leu Val Leu
                245                 250                 255

Gly Cys Asp Ala Ala Leu Val Arg Ala Arg Tyr Gly Arg Glu Phe Met
            260                 265                 270

Gly Leu Val Ile Ser Met His Asp Ser Pro Val Gly Val Met Val
        275                 280                 285

Val Pro Ala Gly Gln Thr Leu Asp Arg Val Gly Asp Pro Ala Asp Glu
290                 295                 300

Asn Pro Pro Gly Ala Leu Pro Gly Pro Pro Gly Gly Pro Arg Tyr Arg
305                 310                 315                 320
```

```
Val Phe Val Leu Gly Ser Leu Thr Arg Ala Asp Asn Gly Ser Ala Leu
                325                 330                 335

Asp Ala Leu Arg Arg Val Gly Gly Tyr Pro Glu Glu Gly Thr Asn Tyr
                340                 345                 350

Ala Gln Phe Leu Ser Arg Ala Tyr Ala Glu Phe Phe Ser Gly Asp Ala
                355                 360                 365

Gly Ala Glu Gln Gly Pro Arg Pro Leu Phe Trp Arg Leu Thr Gly
        370                 375                 380

Leu Leu Ala Thr Ser Gly Phe Ala Phe Val Asn Ala Ala His Ala Asn
385                 390                 395                 400

Gly Ala Val Cys Leu Ser Asp Leu Leu Gly Phe Leu Ala His Ser Arg
                405                 410                 415

Ala Leu Ala Gly Leu Ala Ala Arg Gly Ala Ala Gly Cys Ala Ala Asp
                420                 425                 430

Ser Val Phe Phe Asn Val Ser Val Leu Asp Pro Thr Ala Arg Leu Gln
                435                 440                 445

Leu Glu Ala Arg Leu Gln His Leu Val Ala Glu Ile Leu Glu Arg Glu
        450                 455                 460

Gln Ser Leu Ala Leu His Ala Leu Gly Tyr Gln Leu Ala Phe Val Leu
465                 470                 475                 480

Asp Ser Pro Ser Ala Tyr Asp Ala Val Ala Pro Ser Ala Ala His Leu
                485                 490                 495

Ile Asp Ala Leu Tyr Ala Glu Phe Leu Gly Gly Arg Val Leu Thr Thr
                500                 505                 510

Pro Val His Arg Ala Leu Phe Tyr Ala Ser Ala Val Leu Arg Gln
        515                 520                 525

Pro Phe Leu Ala Gly Val Pro Ser Ala Val Gln Arg Glu Arg Ala Arg
        530                 535                 540

Arg Ser Leu Leu Ile Ala Ser Ala Leu Cys Thr Ser Asp Val Ala Ala
545                 550                 555                 560

Ala Thr Asn Ala Asp Leu Arg Thr Ala Leu Ala Arg Ala Asp His Gln
                565                 570                 575

Lys Thr Leu Phe Trp Leu Pro Asp His Phe Ser Pro Cys Ala Ala Ser
                580                 585                 590

Leu Arg Phe Asp Leu Asp Glu Ser Val Phe Ile Leu Asp Ala Leu Ala
                595                 600                 605

Gln Ala Thr Arg Ser Glu Thr Pro Val Glu Val Leu Ala Gln Gln Thr
        610                 615                 620

His Gly Leu Ala Ser Thr Leu Thr Arg Trp Ala His Tyr Asn Ala Leu
625                 630                 635                 640

Ile Arg Ala Phe Val Pro Glu Ala Ser His Arg Cys Gly Gly Gln Ser
                645                 650                 655

Ala Asn Val Glu Pro Arg Ile Leu Val Pro Ile Thr His Asn Ala Ser
                660                 665                 670

Tyr Val Val Thr His Ser Pro Leu Pro Arg Gly Ile Gly Tyr Lys Leu
                675                 680                 685

Thr Gly Val Asp Val Arg Arg Pro Leu Phe Leu Thr Tyr Leu Thr Ala
        690                 695                 700

Thr Cys Glu Gly Ser Thr Arg Asp Ile Glu Ser Lys Arg Leu Val Arg
705                 710                 715                 720

Thr Gln Asn Gln Arg Asp Leu Gly Leu Val Gly Ala Val Phe Met Arg
                725                 730                 735
```

```
Tyr Thr Pro Ala Gly Glu Val Met Ser Val Leu Leu Val Asp Thr Asp
                740                 745                 750
Asn Thr Gln Gln Gln Ile Ala Ala Gly Pro Thr Glu Gly Ala Pro Ser
            755                 760                 765
Val Phe Ser Ser Asp Val Pro Ser Thr Ala Leu Leu Leu Phe Pro Asn
        770                 775                 780
Gly Thr Val Ile His Leu Leu Ala Phe Asp Thr Gln Pro Val Ala Ala
785                 790                 795                 800
Ile Ala Pro Gly Phe Leu Ala Ser Ala Leu Gly Val Val Met Ile
                805                 810                 815
Thr Ala Ala Leu Ala Gly Ile Leu Lys Val Leu Arg Thr Ser Val Pro
                820                 825                 830
Phe Phe Trp Arg Arg Glu
            835

<210> SEQ ID NO 3
<211> LENGTH: 224
<212> TYPE: PRT
<213> ORGANISM: Human herpesvirus 1

<400> SEQUENCE: 3

Met Gly Ile Leu Gly Trp Val Gly Leu Ile Ala Val Gly Val Leu Cys
1               5                   10                  15
Val Arg Gly Gly Leu Pro Ser Thr Glu Tyr Val Ile Arg Ser Arg Val
                20                  25                  30
Ala Arg Glu Val Gly Asp Ile Leu Lys Val Pro Cys Val Pro Leu Pro
            35                  40                  45
Ser Asp Asp Leu Asp Trp Arg Tyr Glu Thr Pro Ser Ala Ile Asn Tyr
    50                  55                  60
Ala Leu Ile Asp Gly Ile Phe Leu Arg Tyr His Cys Pro Gly Leu Asp
65                  70                  75                  80
Thr Val Leu Trp Asp Arg His Ala Gln Lys Ala Tyr Trp Val Asn Pro
                85                  90                  95
Phe Leu Phe Val Ala Gly Phe Leu Glu Asp Leu Ser Tyr Pro Ala Phe
            100                 105                 110
Pro Ala Asn Thr Gln Glu Thr Glu Thr Arg Leu Ala Leu Tyr Lys Glu
        115                 120                 125
Ile Arg Gln Ala Leu Asp Ser Arg Lys Gln Ala Ala Ser His Thr Pro
130                 135                 140
Val Lys Ala Gly Cys Val Asn Phe Asp Tyr Ser Arg Thr Arg Arg Cys
145                 150                 155                 160
Val Gly Arg Gln Asp Leu Gly Pro Thr Asn Gly Thr Ser Gly Arg Thr
                165                 170                 175
Pro Val Leu Pro Pro Asp Asp Glu Ala Gly Leu Gln Pro Lys Pro Leu
            180                 185                 190
Thr Thr Pro Pro Pro Ile Ile Ala Thr Ser Asp Pro Thr Pro Arg Arg
        195                 200                 205
Asp Ala Ala Thr Lys Ser Arg Arg Arg Pro His Ser Arg Arg Leu
    210                 215                 220

<210> SEQ ID NO 4
<211> LENGTH: 1185
<212> TYPE: DNA
<213> ORGANISM: Human herpesvirus 1

<400> SEQUENCE: 4
```

```
atggggggggg ctgccgccag gttggggggcc gtgattttgt ttgtcgtcat agtgggcctc      60
catgggggtcc gcagcaaata tgccttggtg gatgcctctc tcaagatggc cgaccccaat     120
cgctttcgcg gcaaagacct tccggtcctg gaccagctga ccgaccctcc ggggggtccgg     180
cgcgtgtacc acatccaggc gggcctaccg gacccgttcc agcccccccag cctcccgatc     240
acggtttact acgccgtgtt ggagcgcgcc tgccgcagcg tgctcctaaa cgcaccgtcg     300
gaggcccccc agattgtccg cggggcctcc gaagacgtcc ggaaacaacc ctacaacctg     360
accatcgctt ggtttcggat gggaggcaac tgtgctatcc ccatcacggt catggagtac     420
accgaatgct cctacaacaa gtctctgggg gcctgtccca tccgaacgca gccccgctgg     480
aactactatg acagcttcag cgccgtcagc gaggataacc tggggttcct gatgcacgcc     540
cccgcgtttg agaccgccgg cacgtacctg cggctcgtga agataaacga ctggacggag     600
attacacagt ttatcctgga gcaccgagcc aagggctcct gtaagtacgc cctcccgctg     660
cgcatccccc cgtcagcctg cctctccccc caggcctacc agcaggggggt gacggtggac     720
agcatcggga tgctgccccg cttcatcccc gagaaccagc gcaccgtcgc cgtatacagc     780
ttgaagatcg ccgggtggca cgggcccaag gccccataca cgagcaccct gctgcccccg     840
gagctgtccg agacccccaa cgccacgcag ccagaactcg ccccggaaga ccccgaggat     900
tcggccctct ggaggacccc cgtggggacg gtggcgccgc aaatcccacc aaactggcac     960
ataccgtcga tccaggacgc cgcgacgcct accatccccc cggccacccc gaacaacatg    1020
ggcctgatcg ccggcgcggt gggcggcagt ctcctggcag ccctggtcat ttgcggaatt    1080
gtgtactgga tgcgccgcca cactcaaaaa gccccaaagc gcatacgcct cccccacatc    1140
cgggaagacg accagccgtc ctcgcaccag cccttgtttt actag                    1185
```

<210> SEQ ID NO 5  
<211> LENGTH: 2517  
<212> TYPE: DNA  
<213> ORGANISM: Human herpesvirus 1

<400> SEQUENCE: 5

```
ttattcgcgt ctccaaaaaa acgggacact tgtccggaga acctttagga tgccagccag      60
ggcggcggta atcataacca cgcccagcgc agaggcggcc agaaacccgg gcgcaattgc     120
ggccacgggc tgcgtgtcaa aggctagcaa atgaatgacg gttccgtttg gaaatagcaa     180
caaggccgtg gacggcacgt cgctcgaaaa cacgcttggg gcgccctccg tcggcccggc     240
ggcgatttgc tgctgtgtgt tgtccgtatc caccagcaac acagacatga cctccccggc     300
cggggtgtag cgcataaaca cggcccccac gagcccccagg tcgcgctggt tttgggtgcg     360
caccagccgc ttggactcga tatcccgggt ggagccttcg catgtcgcgg tgaggtaggt     420
taggaacagt gggcgtcgga cgtcgacgcc ggtgagcttg tagccgatcc cccggggcag     480
aggggagtgg gtgacgacgt agctggcgtt gtgggtgatg ggtaccagga tccgtggctc     540
gacgttggca gactgccccc cgcaccgatg tgaggcctca gggacgaagg cgcggatcag     600
ggcgttgtag tgtgcccaac gcgtcagggt cgaggcgagg ccgtgggtct gctgggccag     660
gacttcgacc ggggtctcgg atcggtggcc ttgagccagc gcgtccagga taaacacgct     720
ctcgtctaga tcaaagcgca gggaggccgc gcatggcgaa aagtggtccg gaagccaaaa     780
gagggttttc tggtggtcgg cccgggccag cgccggtccgg aggtcggcgt tggtcgctgc     840
ggcgacgtcg gacgtacaca gggccgaggc tatcagaagg ctccggcggg gcgcgttcccg     900
ctgcaccgcc gaggggacgc cagccaagaa cggctgccgg aggacagccg aggcgtaaaa     960
```

| | |
|---|---|
| tagcgcccgg tggacgaccg gggtggtcag cacgcggccc cctagaaact cggcatacag | 1020 |
| ggcgtcgatg agatgggctg cgctgggcgc cactgcgtcg tacgccgagg ggctatccag | 1080 |
| cacgaaggcc agctgatagc ccagcgcgtg taatgccaag ctctgttcgc gctccagaat | 1140 |
| ctcggccacc aggtgctgga gccgagcctc tagctgcagg cgggccgtgg gatccaagac | 1200 |
| tgacacatta aaaaacacag aatccgcggc acagcccgcg gccccgcggg cggccaaccc | 1260 |
| ggcaagcgcg cgcgagtggg ccaaaaagcc tagcaggtcg gagaggcaga ccgcgccgtt | 1320 |
| tgcgtgggcg gcgttcacga aagcaaaacc cgacgtcgcg agcagccccg ttaggcgcca | 1380 |
| gaagagaggg gggcgcgggc cctgctcggc gcccgcgtcc cccgagaaaa actccgcgta | 1440 |
| tgcccgcgac aggaactggg cgtagttcgt gccctcctcc gggtagccgc ccacgcggcg | 1500 |
| gagggcgtcc agcgcggagc cgttgtcggc ccgcgtcagg gaccctagga caaagacccg | 1560 |
| ataccggggg ccgcccgggg gcccgggaag agccccgggg gggttttcgt ccgcggggtc | 1620 |
| cccgacccga tctagcgtct ggccgcgggg gaccaccatc acttccaccg gagggctgtc | 1680 |
| gtgcatggat atcacgagcc ccatgaattc ccgcccgtag cgcgcgcgca ccagcgcggc | 1740 |
| atcgcacccg agcaccagct cccccgtcgt ccagatgccc acgggccacg tcgaggccga | 1800 |
| cggggagaaa tacacgtacc tacctgggga tctcaacagg ccccgggtgg ccaaccaggt | 1860 |
| cgtgacgcg ttgtgcaggt gcgtgatgtc cagctccgtc gtcgggtgcc gccgggcccc | 1920 |
| aaccggcggt cggggggggcg tgtatcacg cggcccgctc gggtggctcg ccgtcgccac | 1980 |
| gttgtctccc cgcggaacg tcagggcctc ggggtcaggg acggccgaaa acgttaccca | 2040 |
| ggcccgggaa cgcagcaaca cggaggcggc tggattgtgc aagagaccct taagggggc | 2100 |
| gaccgagggg ggaggctggg cggtcggctc gaccgtggtg ggggcgggca ggctcgcgtt | 2160 |
| cggggggccgg ccgagcaggt aggtcttcgg gatgtaaagc agctggccgg ggtcccgcgg | 2220 |
| aaactcggcc gtggtgacca atacaaaaca aaagcgctcc tcgtaccagc gaagaagggg | 2280 |
| cagagatgcc gtagtcaggt ttagttcgtc cggcggcgcc agaaatccgc gcggtggttt | 2340 |
| ttgggggtcg ggggtgttttg gcagccacag acgcccggtg ttcgtgtcgc gccagtacat | 2400 |
| gcggtccatg cccaggccat ccaaaaacca tgggtctgtc tgctcagtcc agtcgtggac | 2460 |
| ctgaccccac gcaacgccca aaataataac ccccacgaac cataaaccat tccccat | 2517 |

<210> SEQ ID NO 6
<211> LENGTH: 675
<212> TYPE: DNA
<213> ORGANISM: Human herpesvirus 1

<400> SEQUENCE: 6

| | |
|---|---|
| atggggattt tgggttgggt cgggcttatt gccgttgggg ttttgtgtgt gcggggggggc | 60 |
| ttgccttcaa ccgaatatgt tattcggagt cgggtggctc gagaggtggg ggatatatta | 120 |
| aaggtgcctt gtgtgccgct cccgtctgac gatcttgatt ggcgttacga gaccccctcg | 180 |
| gctataaact atgctttgat agacggtata tttttgcgtt atcactgtcc cggattggac | 240 |
| acggtcttgt gggataggca tgcccagaag gcatattggg ttaaccccctt tttatttgtg | 300 |
| gcgggttttt tggaggactt gagttacccc gcgtttcctg ccaacacca ggaaacagaa | 360 |
| acgcgcttgg ccctttataa agagatacgc caggcgctgg acagtcgcaa gcaggccgcc | 420 |
| agccacacac ctgtgaaggc tgggtgtgtg aactttgact attcgcgcac ccgccgctgt | 480 |
| gtagggcgac aggatttggg acctaccaac ggaacgtctg gacggacccc ggttctgccg | 540 |

```
ccggacgatg aagcgggcct gcagccgaag cccctcacca cgccgccgcc catcatcgcc    600
acgtcggacc ccaccccgcg acgggacgcc gccacaaaaa gcagacgccg acgacccac     660 tcccggcgcc tctaa                                                    675
```

```
<210> SEQ ID NO 7
<211> LENGTH: 99
<212> TYPE: DNA
<213> ORGANISM: Artificial sequence
<220> FEATURE:
<223> OTHER INFORMATION: Synthetic sequence: Primer ELsfifor

<400> SEQUENCE: 7
gaattcatgg gatggagctg tatcatcctc ttcttggtag caacagctac aggtgtccac    60
tccgcggccc agccggccga tgtgcaactg gtggagtct                          99
```

```
<210> SEQ ID NO 8
<211> LENGTH: 39
<212> TYPE: DNA
<213> ORGANISM: Artificial sequence
<220> FEATURE:
<223> OTHER INFORMATION: Synthetic sequence: Primer R24notrev

<400> SEQUENCE: 8
gagtcattct gcggccgccc gttttatctc cagcttggt                          39
```

```
<210> SEQ ID NO 9
<211> LENGTH: 35
<212> TYPE: DNA
<213> ORGANISM: Artificial sequence
<220> FEATURE:
<223> OTHER INFORMATION: Synthetic sequence: Forward primer

<400> SEQUENCE: 9
ggccgcggcc gcagtccacg actggactga gcaga                              35
```

```
<210> SEQ ID NO 10
<211> LENGTH: 66
<212> TYPE: DNA
<213> ORGANISM: Artificial sequence
<220> FEATURE:
<223> OTHER INFORMATION: Synthetic sequence: Reverse primer

<400> SEQUENCE: 10
gggcccctcg agttaggcgt agtccgggac atcatagggg tattcgcgtc tccaaaaaaa    60
cgggac                                                              66
```

```
<210> SEQ ID NO 11
<211> LENGTH: 26
<212> TYPE: DNA
<213> ORGANISM: Artificial sequence
<220> FEATURE:
<223> OTHER INFORMATION: Synthetic sequence: Primer gCforsac

<400> SEQUENCE: 11
gtgagctccc gaagaccgcc ggtgtg                                        26
```

```
<210> SEQ ID NO 12
<211> LENGTH: 25
<212> TYPE: DNA
<213> ORGANISM: Artificial sequence
<220> FEATURE:
<223> OTHER INFORMATION: Synthetic sequence: Primer gCrevkpn

<400> SEQUENCE: 12
```
agggtaccgg caaagcgaga ccggg                                         25

<210> SEQ ID NO 13
<211> LENGTH: 31
<212> TYPE: DNA
<213> ORGANISM: Artificial sequence
<220> FEATURE:
<223> OTHER INFORMATION: Synthetic sequence: Primer TKforsal

<400> SEQUENCE: 13
agaagtcgac tatgatgaca caaaccccgc c                                  31

<210> SEQ ID NO 14
<211> LENGTH: 28
<212> TYPE: DNA
<213> ORGANISM: Artificial sequence
<220> FEATURE:
<223> OTHER INFORMATION: Synthetic sequence: Primer TKrevpst

<400> SEQUENCE: 14
gactgcagtg cggcacgctg ttgacgct                                      28

<210> SEQ ID NO 15
<211> LENGTH: 64
<212> TYPE: DNA
<213> ORGANISM: Artificial sequence
<220> FEATURE:
<223> OTHER INFORMATION: Synthetic sequence: Reverse primer

<400> SEQUENCE: 15
ggccctcgag gcatgcgcac ccattaaggg ggggtatcta gtaaaacaag ggctggtgcg    60
agga                                                                64

<210> SEQ ID NO 16
<211> LENGTH: 24
<212> TYPE: DNA
<213> ORGANISM: Artificial sequence
<220> FEATURE:
<223> OTHER INFORMATION: Synthetic sequence: Primer F3

<400> SEQUENCE: 16
caggcacggc ccgatgaccg cctc                                          24

<210> SEQ ID NO 17
<211> LENGTH: 18
<212> TYPE: DNA
<213> ORGANISM: Artificial sequence
<220> FEATURE:
<223> OTHER INFORMATION: Synthetic sequence: Primer R13

<400> SEQUENCE: 17
ggccagacgc cgaaaacg                                                 18

<210> SEQ ID NO 18
<211> LENGTH: 42
<212> TYPE: DNA
<213> ORGANISM: Artificial sequence
<220> FEATURE:
<223> OTHER INFORMATION: Synthetic sequence: Primer

<400> SEQUENCE: 18
accttgcagc ggccgcaaga cccaaatctt gtgacaaaac tc                      42

<210> SEQ ID NO 19

```
<211> LENGTH: 51
<212> TYPE: DNA
<213> ORGANISM: Artificial sequence
<220> FEATURE:
<223> OTHER INFORMATION: Synthetic sequence: Primer

<400> SEQUENCE: 19
gatcacgtct cgagttatca tttacccgga gacagggaga ggctctttct g        51

<210> SEQ ID NO 20
<211> LENGTH: 39
<212> TYPE: DNA
<213> ORGANISM: Artificial sequence
<220> FEATURE:
<223> OTHER INFORMATION: Synthetic sequence: gD forward primer 108gD

<400> SEQUENCE: 20
ggatccgcgg ccgcagccga ccccaatcgc tttcgcggc                        39

<210> SEQ ID NO 21
<211> LENGTH: 39
<212> TYPE: DNA
<213> ORGANISM: Artificial sequence
<220> FEATURE:
<223> OTHER INFORMATION: Synthetic sequence: gD forward primer 171gD

<400> SEQUENCE: 21
ggatccgcgg ccgcaggggt ccggcgcgtg taccacatc                        39

<210> SEQ ID NO 22
<211> LENGTH: 39
<212> TYPE: DNA
<213> ORGANISM: Artificial sequence
<220> FEATURE:
<223> OTHER INFORMATION: Synthetic sequence: gD forward primer 231gD

<400> SEQUENCE: 22
ggatccgcgg ccgcactccc gatcacggtt tactacgcc                        39

<210> SEQ ID NO 23
<211> LENGTH: 39
<212> TYPE: DNA
<213> ORGANISM: Artificial sequence
<220> FEATURE:
<223> OTHER INFORMATION: Synthetic sequence: gD forward primer 273gD

<400> SEQUENCE: 23
ggatccgcgg ccgcacgcag cgtgctccta aacgcaccg                        39

<210> SEQ ID NO 24
<211> LENGTH: 39
<212> TYPE: DNA
<213> ORGANISM: Artificial sequence
<220> FEATURE:
<223> OTHER INFORMATION: Synthetic sequence: gD forward primer 312gD

<400> SEQUENCE: 24
ggatccgcgg ccgcaattgt ccgcggggcc tccgaagac                        39

<210> SEQ ID NO 25
<211> LENGTH: 39
<212> TYPE: DNA
<213> ORGANISM: Artificial sequence
<220> FEATURE:
<223> OTHER INFORMATION: Synthetic sequence: gD forward primer 381gD

<400> SEQUENCE: 25
```

-continued

```
ggatccgcgg ccgcaggagg caactgtgct atccccatc                    39
```

<210> SEQ ID NO 26
<211> LENGTH: 39
<212> TYPE: DNA
<213> ORGANISM: Artificial sequence
<220> FEATURE:
<223> OTHER INFORMATION: Synthetic sequence: gD forward primer 414gD

<400> SEQUENCE: 26

```
ggatccgcgg ccgcagagta caccgaatgc tcctacaac                    39
```

<210> SEQ ID NO 27
<211> LENGTH: 39
<212> TYPE: DNA
<213> ORGANISM: Artificial sequence
<220> FEATURE:
<223> OTHER INFORMATION: Synthetic sequence: gD forward primer 489gD

<400> SEQUENCE: 27

```
ggatccgcgg ccgcagacag cttcagcgcc gtcagcgag                    39
```

<210> SEQ ID NO 28
<211> LENGTH: 39
<212> TYPE: DNA
<213> ORGANISM: Artificial sequence
<220> FEATURE:
<223> OTHER INFORMATION: Synthetic sequence: gD forward primer 534gD

<400> SEQUENCE: 28

```
ggatccgcgg ccgcacacgc ccccgcgttt gagaccgcc                    39
```

<210> SEQ ID NO 29
<211> LENGTH: 39
<212> TYPE: DNA
<213> ORGANISM: Artificial sequence
<220> FEATURE:
<223> OTHER INFORMATION: Synthetic sequence: gD forward primer 570gD

<400> SEQUENCE: 29

```
ggatccgcgg ccgcacggct cgtgaagata aacgactgg                    39
```

<210> SEQ ID NO 30
<211> LENGTH: 39
<212> TYPE: DNA
<213> ORGANISM: Artificial sequence
<220> FEATURE:
<223> OTHER INFORMATION: Synthetic sequence: gD forward primer 618gD

<400> SEQUENCE: 30

```
ggatccgcgg ccgcagagca ccgagccaag ggctcctgt                    39
```

<210> SEQ ID NO 31
<211> LENGTH: 39
<212> TYPE: DNA
<213> ORGANISM: Artificial sequence
<220> FEATURE:
<223> OTHER INFORMATION: Synthetic sequence: gD forward primer 690gD

<400> SEQUENCE: 31

```
ggatccgcgg ccgcacaggc ctaccagcag ggggtgacg                    39
```

<210> SEQ ID NO 32
<211> LENGTH: 39
<212> TYPE: DNA

```
<213> ORGANISM: Artificial sequence
<220> FEATURE:
<223> OTHER INFORMATION: Synthetic sequence: gD forward primer 714gD

<400> SEQUENCE: 32
ggatccgcgg ccgcagtgga cagcatcggg atgctgccc                             39

<210> SEQ ID NO 33
<211> LENGTH: 39
<212> TYPE: DNA
<213> ORGANISM: Artificial sequence
<220> FEATURE:
<223> OTHER INFORMATION: Synthetic sequence: gD forward primer 777gD

<400> SEQUENCE: 33
ggatccgcgg ccgcaagctt gaagatcgcc gggtggcac                             39

<210> SEQ ID NO 34
<211> LENGTH: 39
<212> TYPE: DNA
<213> ORGANISM: Artificial sequence
<220> FEATURE:
<223> OTHER INFORMATION: Synthetic sequence: gD forward primer 819gD

<400> SEQUENCE: 34
ggatccgcgg ccgcaacgag caccctgctg ccccggag                              39

<210> SEQ ID NO 35
<211> LENGTH: 46
<212> TYPE: DNA
<213> ORGANISM: Artificial sequence
<220> FEATURE:
<223> OTHER INFORMATION: Synthetic sequence: gD reverse primer

<400> SEQUENCE: 35
ggccaagctt ctcgagtcta gagtaaaaca agggctggtg cgagga                     46

<210> SEQ ID NO 36
<211> LENGTH: 36
<212> TYPE: DNA
<213> ORGANISM: Artificial sequence
<220> FEATURE:
<223> OTHER INFORMATION: Synthetic sequence: gL forward primer gLfor0

<400> SEQUENCE: 36
ggccgcggcc gcattgtctt caaccgaata tgttat                                36

<210> SEQ ID NO 37
<211> LENGTH: 54
<212> TYPE: DNA
<213> ORGANISM: Artificial sequence
<220> FEATURE:
<223> OTHER INFORMATION: Synthetic sequence: gL forward primer gLfor1

<400> SEQUENCE: 37
ggatccgcgg ccgcaggtgg aggcggttca ttgtcttcaa ccgaatatgt tatt            54

<210> SEQ ID NO 38
<211> LENGTH: 69
<212> TYPE: DNA
<213> ORGANISM: Artificial sequence
<220> FEATURE:
<223> OTHER INFORMATION: Synthetic sequence: gL forward primer gLfor2
```

```
<400> SEQUENCE: 38
ggatccgcgg ccgcaggtgg aggcggttca ggtggaggcg gttcattgtc ttcaaccgaa    60
tatgttatt                                                            69

<210> SEQ ID NO 39
<211> LENGTH: 84
<212> TYPE: DNA
<213> ORGANISM: Artificial sequence
<220> FEATURE:
<223> OTHER INFORMATION: Synthetic sequence: gL forward primer gLfor3

<400> SEQUENCE: 39
ggatccgcgg ccgcaggtgg aggcggttca ggtggaggcg gttcaggtgg aggcggttca    60
ttgtcttcaa ccgaatatgt tatt                                           84

<210> SEQ ID NO 40
<211> LENGTH: 46
<212> TYPE: DNA
<213> ORGANISM: Artificial sequence
<220> FEATURE:
<223> OTHER INFORMATION: Synthetic sequence: gL reverse primer

<400> SEQUENCE: 40
ggccaagctt gggccctcta gagaggcgcc gggagtgggg tcgtcg                   46

<210> SEQ ID NO 41
<211> LENGTH: 5
<212> TYPE: PRT
<213> ORGANISM: Artificial sequence
<220> FEATURE:
<223> OTHER INFORMATION: Synthetic sequence: Spacer

<400> SEQUENCE: 41

Gly Gly Gly Gly Ser
1               5

<210> SEQ ID NO 42
<211> LENGTH: 10
<212> TYPE: PRT
<213> ORGANISM: Artificial sequence
<220> FEATURE:
<223> OTHER INFORMATION: Synthetic sequence: Spacer

<400> SEQUENCE: 42

Gly Gly Gly Gly Ser Gly Gly Gly Gly Ser
1               5                   10

<210> SEQ ID NO 43
<211> LENGTH: 15
<212> TYPE: PRT
<213> ORGANISM: Artificial sequence
<220> FEATURE:
<223> OTHER INFORMATION: Synthetic sequence: Spacer

<400> SEQUENCE: 43

Gly Gly Gly Gly Ser Gly Gly Gly Gly Ser Gly Gly Gly Gly Ser
1               5                   10                  15
```

VIRUSES

CROSS-REFERENCE TO RELATED APPLICATIONS

This application is a 35 USC 0371 of PCT Application Serial No. PCT/GB2008/001156, filed Apr. 2, 2008, currently pending, entitled "Viruses," which claims priority to Great Britain Patent Application No. 0714578.2, filed Jul. 26, 2007, entitled "Viruses," which are each incorporated herein in their entirety by reference.

FIELD OF THE INVENTION

The present invention relates to Herpes Simplex Viruses, glycoproteins, including mutated glycoproteins and glycoprotein fusion molecules, and to HSV encoding such glycoproteins. More particularly, the invention relates to Herpes Simplex Viruses that are able to target specific cell types.

Incorporated by reference herein in its entirety is the Sequence Listing co-submitted with the instant application, entitled "sequence listing txt.TXT", created Jan. 14, 2010, size of 27 kilobytes.

BACKGROUND

Harnessing the cytopathic effects of virus infection is rapidly becoming established as an anti-cancer treatment and replication-competent mutants of the alpha-herpesvirus, herpes simplex virus type 1 (HSV-1), are showing great potential as oncolytic therapeutic agents.[1, 2] The HSV-1 mutant 1716, lacking the ICP34.5 gene, has greatly reduced lethality in mice but replicates as efficiently as wild-type virus in actively dividing tissue culture cells.[3, 4] The ICP34.5 ORF is a neurovirulence gene and its protein product has been proposed to condition post-mitotic cells for viral replication, probably via an interaction with proliferating cell nuclear antigen.[5, 6] ICP34.5 deletion mutants cannot replicate in terminally differentiated cells but will lytically infect dividing cells and this has proved to be an effective tumour destruction strategy. In recent clinical trials, injection of HSV1716 has been shown to be safe in treating patients with recurrent glioma, metastatic melanoma and squamous cell carcinoma of the head and neck (Mace et al unpublished results) and proof of principle of selective replication within tumours has been obtained.[7-10]

Initiation of infection by HSV-1 requires cells to display the appropriate receptors to permit viral access, a process requiring the complex interplay of a number of cellular and viral membrane components.[37, 38] Four virus membrane glycoproteins, gB, gD and the heterodimer comprising gH and gL (gH/gL) have been shown to be necessary and sufficient for HSV-1 entry into cells. Initial contact is between gB and cellular heparan sulphate, gD then interacts specifically with the cellular receptors for HSV-1 entry which include herpesvirus entry mediator (HVEM), nectins-1 and -2 and 3-O-sulphated heparan sulphate. Membrane fusion requires the concerted activities of gB and gH/gL so that the nucleocapsid gains access to the cell and infection is initiated. Nectin-1 is probably the principal entry receptor for infection of central and peripheral nerve cells whereas HVEM expression is more restricted and limited to cells of lymphoid origin.[39-43]

An essential strategy for the improved effectiveness of oncolytic viral therapies depends upon systemic delivery of targeted viruses that seek out and destroy all cancerous cells.[2, 11, 12] However, wide bioavailability of HSV-1 entry mediators will hinder the ability of systemically administered oncolytic HSV1716 to efficiently target the cells of interest.

Reprogramming viral tropisms has thus received much attention, an approach requiring redirection of the natural tropism from native receptors to a receptor of choice. Targeted infection by vaccinia virus, retrovirus and measles virus, displaying single chain antibody binding sites incorporated into their structure by fusion with viral envelope proteins has been described.[13-21, 55] Bridging, bispecific targeting molecules comprising either an anti-adenovirus single chain antibody or the Coxsackievirus-adenovirus receptor linked to a targeting single chain antibody, have been used for targeting oncolytic adenoviruses.[22-28]

Results from a number of studies with HSV-1 have shown that it is possible to alter the tropism by incorporating ligands such as erythropoeitin, IL13, human hepatitis B virus preS1 peptide, the N-terminal fragment of urokinase-type plasminogen activator or 6-His into the viral envelope as glycoprotein fusion proteins.[29-34, 56, 57]

Targeting has also been achieved using a soluble adaptor molecule, in which the soluble adaptor molecule includes an EGFR scFv linked to the HSV-1 gD-binding domain of nectin-1. More recently, a scFv against HER2/neu, inserted within an N terminal region of gD, has been shown to redirect the tropism of HSV-1 to this mammary tumour receptor.[35,36] HSV capable of targeting cells and tissues is also described in WO 03/068809.

SUMMARY OF THE INVENTION

Systemic delivery of HSV oncolytic viral therapies requires that the oncolytic virus, once administered, is able to target tumour cells. If the systemically administered oncolytic virus shows only low specificity for the target tumour cells such treatment may not be optimally effective.

As far as the inventors are aware, studies to date have merely shown that the tropism of HSV may be redirected and have not provided any strategy for improving redirection. In view of the therapeutic potential of systemically delivered oncolytic viral therapies, there is a clear need for alternative oncolytic viral agents that are able to redirect tropism more efficiently towards tumour cells.

We have investigated the possibility of redesigning tropism of HSV by embedding single-chain antibodies (scFv) in the viral envelope via fusion with glycoprotein D and with glycoprotein H and L. We demonstrate here that scFv linked to the N-terminus of truncated glycoprotein D molecules is specifically able to influence the tropism of HSV towards cells displaying tumour markers. In particular, we have identified a short glycoprotein D truncate which efficiently redirected HSV infectivity, thereby providing a route for the development of effective tumour-targeted HSV for systemic delivery.

We investigated the ability of scFvs incorporated into the viral envelope to alter the tropism of herpes simplex virus HSV1716. Fusion proteins were created by N-terminally linking a scFv that recognises the ganglioside GD3 to 15 sequentially deleted gD polypeptides and to both gH and gL in the gH/gL heterodimer. Vero cell lines stably expressing the scFv/glycoprotein fusions were infected with an HSV1716 variant expressing gfp and the efficiencies of the resultant viruses displaying the fusion proteins to infect nonpermissive GD3-positive CHO cells were assessed by fluorescence microscopy and Western blotting. Viruses displaying scFv/gD or the scFv/gH/gL heterodimers were able to infect the normally non-permissive CHO cells. Further, our observations identified a gD fragment comprising amino acids 274-393 which was most efficient at redirecting viral tropism.

We subsequently created a number of HSV1716 variants that expressed different scFv targeting moieties linked to the gD fragments that were most efficient at redirecting viral tropism. Using non- or semi-permissive cell lines, we demonstrated that the tropism of these HSV1716 variants was modified such that infection was mediated via the cognate antigen.

We also performed in vivo experiments using mice in which subcutaneous tumours were established using the human epidermoid carcinoma cell line, A431. The mice were systemically injected with an HSV-1 variant which expressed anti-epidermal growth factor receptor (EGFR) scFv linked to the gD fragment comprising amino acids 274-393. We found that mice receiving this HSV-1 variant had more slowly growing tumours than those receiving HSV1716, indicating that the targeted HSV-1 variant had greater therapeutic benefit than the non-targeted HSV1716.

Thus, a redirection of HSV1716 tropism to specific cell types through the display of tumour targeting scFv moieties linked to particular glycoproteins and variants thereof identifies an efficient route for systemic delivery.

Accordingly, in a broad aspect, the invention provides a herpes simplex virus comprising an N-terminally truncated glycoprotein D, which truncated glycoprotein D is linked to a targeting agent.

The surprising discovery that N-terminally truncated glycoprotein D molecules linked to a targeting agent are able to efficiently redirect the tropism of HSV provides a new family of HSVs showing redirected tropism, and opens up a new route for the development of effective anti-tumour agents.

Structurally, HSV-1 glycoprotein D has an extracellular domain consisting of 315 amino acids, with binding to HVEM requiring residues 1 to 34 and binding to nectin-1 requiring residues 34 to 243.[48-51]

The inventors have demonstrated that a glycoprotein D lacking amino acids 1 to 36 and bound to a scFv is able to redirect HSV tropism. As binding to HVEM requires amino acids 1 to 34, this glycoprotein D will have an impaired ability to bind HVEM. The inventors have also demonstrated that a glycoprotein D lacking amino acids 1 to 259 and bound to a scFv is also able to redirect HSV tropism. As binding to nectin-1 requires amino acids 34 to 243, this glycoprotein D will have an impaired ability to bind nectin-1.

According to a first aspect of the invention, there is provided a HSV comprising an N-terminally truncated glycoprotein D linked to a targeting agent, wherein the N-terminally truncated glycoprotein D does not include a functional HVEM binding domain. Preferably, the glycoprotein D also does not include a functional nectin-1 binding domain.

In a further aspect of the invention, there is provided a HSV comprising nucleic acid encoding a fusion protein, which fusion protein comprises an N-terminally truncated glycoprotein D linked to a targeting agent, wherein the N-terminally truncated glycoprotein D does not include a functional HVEM binding domain. Preferably the glycoprotein D also does not include a functional nectin-1 binding domain. The nucleic acid is preferably arranged in the HSV genome such that the HSV is capable of expressing the nucleic acid encoding the fusion protein.

In lacking a functional HVEM binding domain and/or a nectin-1 binding domain, the truncated glycoprotein D has a reduced affinity, or no specific affinity, for HVEM and/or nectin-1. The affinity of the truncated glycoprotein D for HVEM and/or nectin-1 may be reduced such that the HSV comprising the truncated glycoprotein D is not capable of entering a cell by a mechanism which involves binding of glycoprotein D to HVEM and/or nectin-1. For example, the truncated glycoprotein D may not be able to mediate entry into cells expressing HVEM and/or nectin-1 as the sole receptor.

Binding of the truncated glycoprotein D to HVEM and/or nectin-1 may be measured, for example, by using ELISA. This may involve coating a surface with HVEM and/or nectin-1, adding the truncated glycoprotein D, and then detecting glycoprotein D bound to the surface. Preferably, the binding affinity of the truncated glycoprotein D for HVEM and/or nectin-1 is less than 50%, 40%, 30%, 20%, 10%, 5%, 3% or even less than 1% of the affinity of wild-type glycoprotein D, e.g. glycoprotein D having the sequence of SEQ ID NO: 1, for HVEM and/or nectin-1. Binding of the truncated glycoprotein D may be determined with or without the targeting agent linked to the truncated glycoprotein D. Preferably the truncated glycoprotein D has no specific affinity for HVEM and/or nectin-1.

The ability of the truncated glycoprotein D to mediate cell entry via binding to HVEM and/or nectin-1 may be determined by preparing a HSV comprising the truncated glycoprotein D, with or without the targeting agent linked to the glycoprotein D. The HSV may then be used to infect cells, e.g. CHO cells, that express only HVEM and/or nectin-1 as a receptor for the glycoprotein D. The level of infection may be measured by fluorescence microscopy. Assays for determining infection of cells by HSV by fluorescence microscopy are described below. Preferably the ability of the truncated glycoprotein D to mediate cell entry via binding to HVEM and/or nectin-1 is less than 50%, 40%, 30%, 20%, 10%, 5%, 3% or even less than 1% of the ability of wild-type glycoprotein D, e.g. glycoprotein D having the sequence of SEQ ID NO: 1. Preferably, the truncated glycoprotein D has no ability to mediate cell entry via binding to HVEM and/or nectin-1.

Structural studies of glycoprotein D binding to HVEM have identified critical regions at the binding interface. In particular, three glycoprotein D mutations were identified that each resulted in the complete loss of HVEM binding to glycoprotein D and the failure to mediate HSV entry into cells expressing HVEM. These mutations were Q27A, T29A and D30A. Preferably the truncated glycoprotein D has an inactivating mutation at each of these amino acid positions, i.e. 27, 29, and 30, or more preferably, these residues are absent from the truncated gD.

The normal route by which HSV-1 infects a cell requires a complex interplay of a number of cellular and viral membrane components, including the specific interaction of glycoprotein D with HVEM and nectin-1. Nectin-1 is thought to be the principal entry receptor for infection of central and peripheral nerve cells whereas HVEM expression is more restricted and limited to cells of lymphoid origin. Thus, truncating glycoprotein D such that it does not include a functional HVEM and/or nectin-1 binding domain will reduce the ability of HSV to infect its normal target. This will increase the specificity of the HSV away from its normal target and towards cells expressing the surface antigens for which the targeting agent linked to the truncated glycoprotein D is specific, e.g. tumour cells.

In a further aspect of the invention, there is provided a HSV comprising an N-terminally truncated glycoprotein D linked to a targeting agent, wherein the N-terminally truncated glycoprotein D does not include a portion of amino acids corresponding to amino acids 1 to 34 of the full-length HSV-1 glycoprotein D.

In a further aspect of the invention, there is provided a HSV comprising nucleic acid encoding a fusion protein, which fusion protein comprises an N-terminally truncated glycoprotein D linked to a targeting agent, wherein the N-terminally truncated glycoprotein D does not include a portion of amino acids corresponding to 1 to 34 of the full-length HSV-1 glycoprotein D. The nucleic acid is preferably arranged in the HSV genome such that the HSV is capable of expressing the nucleic acid encoding the fusion protein.

Preferably, the truncated glycoprotein D does not include amino acids 1 to 35, more preferably amino acids 1 to 36 of the full-length glycoprotein D.

Thus, the position of the truncation may be at least at a position corresponding to position 35 of the full-length HSV-1 glycoprotein D, for example at least at a position corresponding to position 36, or at least at a position corresponding to position 37. A truncation at least at a position corresponding to position 35, 36, or 37 means a truncation at a position corresponding to position 35, 36, 37, respectively, or at a position corresponding to a position in the full-length HSV-1 glycoprotein D that is closer to the C-terminus than position 35, 36, or 37, respectively. Preferably the position of the truncation is in the glycoprotein D extracellular domain.

An amino acid "position" refers to the position of the amino acid in the polypeptide chain, e.g. the polypeptide chain of glycoprotein D. Unless otherwise indicated, amino acids are numbered such that the N-terminal amino acid is at the first position. For example, an amino acid at position 10 refers to the 10th amino acid in the polypeptide chain counting from the N-terminus.

The "N-terminal" amino acid is the amino acid at the amino-terminal end of the polypeptide of interest. Likewise, the "C-terminal" amino acid is the amino acid at the carboxyl-terminal end of the polypeptide of interest. Thus, an amino acid on the C-terminal side of a position of interest refers to an amino acid that has a position that is closer to the C-terminus of the polypeptide. Likewise, an amino acid on the N-terminal side of a position of interest refers to an amino acid that has a position that is closer to the N-terminus of the polypeptide.

An amino acid in an N-terminally truncated glycoprotein D that corresponds to an amino acid at a position of interest in the full-length HSV-1 glycoprotein D is an amino acid that occupies an equivalent position in the truncated glycoprotein D polypeptide chain compared to the full-length HSV-1 glycoprotein D polypeptide chain. Such corresponding amino acids may be identified by standard amino acid sequence alignments. Preferably corresponding amino acids are identified by aligning the extracellular domain of the N-terminally truncated glycoprotein D with the full-length HSV-1 glycoprotein D.

Methods of performing alignments are well known in the art, e.g. BLAST. The amino acid in the truncated polypeptide that is paired by the alignment with the amino acid at the position of interest in the full-length HSV-1 glycoprotein D sequence is the amino acid in the truncated glycoprotein D that corresponds to the amino acid position of interest.

A truncation at a position corresponding to amino acid position "X" in the full length HSV-1 glycoprotein D means that the amino acid corresponding to position X has been retained in the truncated glycoprotein D, and that all the amino acids on the N-terminal side of this amino acid have been deleted. For example, if the position of the truncation corresponds to amino acid position 37 of the full-length HSV-1 glycoprotein D, then the amino acid corresponding to position 37 is retained in the truncated polypeptide, whereas all amino acids on the N-terminal side of this amino acid are deleted, i.e. the amino acids corresponding to 1-36. For example, the amino acids corresponding to position 37 through to the C-terminal amino acid, e.g. position 393, are retained in the truncate.

Nucleic acid encoding any fusion protein of the invention is preferably inserted in the HSV genome such that is it capable of being transcribed. The nucleic acid may be operably linked to a suitable regulatory sequence (e.g. a promoter), the activity of which may be constitutive or may be controlled by the availability of a signal molecule. The promoter may be, for example, an endogenous HSV promoter such as the gC promoter, or a non endogenous promoter such as the CMV-IE promoter.

As reported here, we have also discovered that a truncated glycoprotein D truncated at position 274 and linked to a targeting agent retains the ability to redirect the tropism of HSV. Moreover, we found that, of the truncates tested, targeting agents linked to glycoprotein D truncated at position 260 and 274 were most efficient at redirecting viral tropism. For example, HSV comprising R24 scFv linked to these truncates was able to infect 60% and 50%, respectively, of normally non-permissive CHO cells.

Thus, the truncated glycoprotein D may have an extracellular domain comprising at least 35 amino acids. The 35 amino acids are preferably the portion of amino acids in the extracellular domain of the full-length HSV-1 glycoprotein D that includes the C-terminal amino acid in the extracellular domain of the HSV-1 full-length glycoprotein D.

Preferably, the truncated glycoprotein D has an extracellular domain comprising at least 36, 37, 38, 39, 40 or 41 amino acids, most preferably at least 42 amino acids. The 36, 37, 38, 39, 40, 41, or 42 amino acids are preferably the portion of amino acids in the extracellular domain of the full-length HSV-1 glycoprotein D, which portion includes the C-terminal amino acid of the extracellular domain of the full-length HSV-1 glycoprotein D.

The HSV-1 glycoprotein D used in the experiments reported below has 315 amino acids in its extracellular domain. Thus, the glycoprotein D truncated at position 274 retained 42 amino acids in its extracellular domain.

Our discovery that a glycoprotein D truncated at position 274 was capable of efficiently redirecting tropism was particularly surprising. Previous studies have suggested that amino acids 261-305 form a distinct domain, the "profusion domain", which is necessary for mediating the membrane fusion event required for penetration of the HSV-1 nucleo-capsid into the cell[12]. The 274 truncate lacks a portion of the profusion domain, yet is still capable of mediating cell entry when linked to a targeting agent.

The truncated glycoprotein D may have an extracellular domain comprising a portion of amino acids corresponding to amino acids 280-315 of the full-length HSV-1 glycoprotein D. For example, the truncated glycoprotein D may have an extracellular domain comprising a portion of amino acids corresponding to amino acids 279-315, 278-315, 277-315, 276-315, or 275-315, preferably 274-315 of the full-length HSV-1 glycoprotein D. Preferably said portion of amino acids of the truncated glycoprotein D includes an amino acid corresponding to the C-terminal amino acid of the extracellular domain of the full-length HSV-1 glycoprotein D.

The position of truncation may correspond to an amino acid position from 240-280 of the full-length HSV-1 glycoprotein D. For example, the position of truncation may correspond to amino acid position 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, or 280 of the full-length HSV-1 glycoprotein D. The position of the truncation may correspond to an amino acid position from 244-280, 244-279, 244-278, 244-277, 244-276, 244-275, or 244-274 of the full-length glycoprotein D. A glycoprotein D truncated at least at a position corresponding to position 244 will lack the entire HVEM and nectin-1 binding domains.

The position of the truncation may correspond to an amino acid position from 260-280, 260-279, 260-278, 260-277, 260-276, or 260-275 of the full-length HSV-1 glycoprotein D, for example from 250-274, 251-274, 252-274, 253-274, 254-274, 255-274, 256-274, 257-274, 258-274, or 259-274 of the full-length HSV-1 glycoprotein D, for example from 250-280, 253-279, 255-278, 257-277, 258-276, or 259-275 of the full-length HSV-1 glycoprotein D.

The position of the truncation may correspond to an amino acid position from 260-274 of the full-length HSV-1 glycoprotein D. Thus, the truncated glycoprotein D may not include amino acids corresponding to the amino acids at positions 1-259 of the full-length HSV-1 glycoprotein D. In particular, the position of the truncation may correspond to the amino acid at position 260 or 274 of the full-length HSV-1 glycoprotein D.

We also report here that truncating the glycoprotein D at position 37, 78, 92, and 128 also leads to redirected viral tropism.

Thus, the position of truncation may correspond to an amino acid position from 35-138 of the full-length HSV-1 glycoprotein D. For example, the position of truncation may correspond to amino acid position 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, or 138 of the full-length HSV-1 glycoprotein D. However, preferably the position of truncation does not correspond to position 58 or 105 of the full-length HSV-1 glycoprotein D.

The position of truncation may correspond to an amino acid position from 35-138, 35-137, 35-136, 35-135, 35-134, 35-133, 35-132, 35-131, 35-130, 35-129 or 35-128 of the full-length glycoprotein D; for example from 36-138, 36-137, 36-136, 36-135, 36-134, 36-133, 36-132, 36-131, 36-130, 36-129, or 36-128, of the full-length glycoprotein D; for example from 37-138, 37-137, 37-136, 37-135, 37-134, 37-133, 37-132, 37-131, 37-130, or 37-129 of the full-length HSV-1 glycoprotein D.

The position of the truncation may correspond to an amino acid position from 37 to 128 of the full-length polypeptide. In particular, the position of the truncation may correspond to the amino acid at position 37, 78, 92, or 128 of the full-length HSV-1 glycoprotein D.

The position of the N-terminal truncation is preferably not at an amino acid position corresponding to position 139, 164, 179, 191, 207, 231 and/or 239 of the full-length HSV-1 glycoprotein D. More preferably, the N-terminal truncation is not at an amino acid position corresponding to a position from 139-239 of the full-length HSV-1 glycoprotein D.

In addition, the position of the truncation may not correspond to an amino acid position from 129-138 and/or from 240-259 of the full-length HSV-1 glycoprotein D. For example, the position of truncation may not be at an amino acid position corresponding to position 138, 137, 136, 135, 134, 133, 132, 131, 130, or 129 of the full-length HSV-1 glycoprotein D. Likewise, the position of the truncation may not be at an amino acid position corresponding to position 240, 241, 242, 243, 244, 245, 246, 247, 248, 249, 250, 251, 252, 253, 254, 255, 256, 257, 258, or 259 of the full-length HSV-1 glycoprotein D. For example, the position of the truncation may not be at an amino acid position corresponding to a position from 137-243, 135-247, 133-251, 131-255, or 129-259 of the full-length HSV-1 glycoprotein D.

In all aspects and embodiments of the invention, the term "full-length HSV-1 glycoprotein D" refers to the polypeptide sequence of an endogenous HSV-1 glycoprotein D in the form in which it is presented in the viral envelope, e.g. without any N-terminal signal sequence or N-terminal methionine that is normally removed during post-translational modification. Preferably the term refers to the sequence of the HSV-1 strain 17 glycoprotein D, i.e. the glycoprotein D sequence having accession no. X14112.1 (GI:1944536), which is SEQ ID NO: 1.

However, the N-terminally truncated glycoprotein D molecules defined above are not limited to truncates of any particular glycoprotein D. Rather, the invention covers N-terminally truncated glycoprotein D molecules derived from any glycoprotein D of any strain of HSV. For example, the truncated glycoprotein may be derived from any of the following glycoprotein D NCBI database entries:

Human HSV-1: NC_001806.1 GI:9629378; AF487902.1 GI:19548970; U03045.1 GI:436475; K02372.1 GI:330102; J02217.1 GI:330100; AAL90884.1 GI:19548971, P36318 GI:549371; AAA45785.1 GI:330101; AF487902.1 GI:19548970; AF487901.1 GI:19548968; AF487901.1 GI:19548968; J02217.1 GI:330100; AAL90883.1 GI:19548969; CAA38245.1 GI:60415; NP_044668.1 GI:9629447.

Human HSV-2: Z86099.2 GI:6572414, D00026.1 GI:221778; NC_001798.1 GI:9629267; AY779754.1 GI:56698871; AY779753.1 GI:56698869; AY779752.1 GI:56698867; AY779751.1 GI:56698865; AY779750.1 GI:56698863; E00394.1 GI:2168679; AAA98962.1 GI:409565; AAW23134.1 GI:56698872; AAW23133.1 GI:56698870; AAW23132.1 GI:56698868; NP_044536.1 GI:9629336; NP_044537.1 GI:9629337

Equine HSV-1: AAS45960.1 GI:42795203; AY464052.1 GI:42795127.

Gallid HSV-2: DQ530348.1 GI:104303917.

Felid HSV-1: D42113.1 GI:893368.

Other glycoprotein D may be identified using the hybridisation and probe techniques as described below. However, it is preferred that the N-terminally truncated glycoprotein D molecules of the invention are truncates of any of the above glycoprotein D molecules for which a database accession number is provided. More preferably, the N-terminally truncated glycoprotein D molecules of the invention are truncates of glycoprotein D from human strains of HSV, in particular HSV-1 or HSV-2 glycoprotein D, more preferably HSV-1. Most preferably the truncate is derived from the glycoprotein D of HSV-1 strain 17 or F. The N-terminally truncated glycoprotein D is preferably an N-terminal truncate of a glycoprotein D having the amino acid sequence of SEQ ID NO: 1. Accordingly, the N-terminally truncated glycoprotein D may be derived from the glycoprotein D encoded by the nucleic acid of SEQ ID NO: 4. In this case, nucleic acid encoding the truncated glycoprotein D may comprise the portion of the nucleic acid sequence of SEQ ID NO: 4 that encodes the truncated glycoprotein D.

Where, for example, the truncated glycoprotein D is derived from a glycoprotein D that has a different number of amino acids to the HSV-1 glycoprotein D, or a different amino acid sequence, corresponding amino acids may be identified by aligning the sequence with the full length HSV-1 glycoprotein D sequence using an alignment program, such as BLAST.

The N-terminally truncated glycoprotein D of the invention may also include amino acids corresponding to those of the transmembrane domain and/or the intracellular domain of the full-length HSV-1 glycoprotein D, i.e. amino acids corresponding to amino acids 316-393 of the full-length HSV-1 glycoprotein D. Preferably the truncated glycoprotein D comprises the transmembrane domain and intracellular domain of SEQ ID NO: 1, i.e. amino acids 316-393 of SEQ ID NO: 1.

In addition to the truncated glycoprotein D molecules of the invention, the HSV may, or may not, also comprise wild-type glycoprotein D, i.e. the full-length glycoprotein D without being linked to a targeting agent. In both cases the HSV will have a reduced affinity for its natural targets, e.g. HVEM and nectin-1. HSV that does not comprise wild-type glycoprotein D will have a restricted tropism, i.e. the absence of wild-type glycoprotein D means that the virus will have a reduced affinity, or no specific affinity, for the HVEM or nectin-1 binding receptors. The HSV would be dependent solely upon the truncated glycoprotein D linked to a targeting agent for infection. HSV comprising the truncated glycoprotein D molecules of the invention in addition to wild-type glycoprotein D will have an expanded tropism, i.e. an expanded repertoire of receptor binding capacity, due to the presence of the targeting agent linked to the truncated glycoprotein D. Any affinity of the HSV for HVEM and/or nectin-1 due to the presence of wild-type glycoprotein D will be diluted by additional affinity for the ligand of the targeting agent. Also, assimilation of the truncated glycoprotein D into the viral envelope will compete with wild-type glycoprotein D incorporation leading to a reduction in the amount of wild-type glycoprotein D and reduced HVEM/nectin-1 binding capacity. This will reduce the affinity of the HSV for its natural target when the ligand of the targeting agent is present. The advantage of retaining the wild-type glycoprotein D in the HSV is that such a virus would be propagated readily in tissue culture whilst at the same time it would have greater specificity for a specific tumour type.

In a further aspect of the invention, there is provided a fusion protein comprising an N-terminally truncated glycoprotein D linked to a targeting agent, wherein the N-terminally truncated glycoprotein D does not include a functional HVEM binding domain and may not include a functional nectin-1 binding domain.

In a further aspect of the invention, there is provided a fusion protein comprising an N-terminally truncated glycoprotein D linked to a targeting agent, wherein the N-terminally truncated glycoprotein D does not include amino acids 1 to 34 of the full-length HSV-1 glycoprotein D. Alternatively, the fusion protein may comprise any truncated glycoprotein D described above.

In a further aspect of the invention, there is provided a nucleic acid molecule comprising nucleic acid encoding a fusion protein, which fusion protein comprises an N-terminally truncated glycoprotein D linked to a targeting agent, wherein the N-terminally truncated glycoprotein D does not include a functional HVEM binding domain and may not include a functional nectin-1 binding domain.

In a further aspect of the invention, there is provided a nucleic acid molecule comprising nucleic acid encoding a fusion protein, which fusion protein comprises an N-terminally truncated glycoprotein D linked to a targeting agent, wherein the N-terminally truncated glycoprotein D does not include amino acids 1 to 34 of the full-length HSV-1 glycoprotein D. Alternatively, the fusion protein may comprise any truncated glycoprotein D described above.

Nucleic acid encoding a fusion protein may be arranged in the nucleic acid molecule such that it is operably linked to a suitable regulatory sequence (e.g. a promoter). A promoter may be constitutive or may be controlled by the availability of a signal molecule. The promoter may be, for example, an endogenous HSV promoter such as the gC promoter, or a non endogenous promoter such as the CMV-IE promoter. The nucleic acid molecule may also include nucleic acid for facilitating insertion of the nucleic acid encoding the fusion protein into the genome of a HSV. Said insertion may be, for example, by homologous recombination, or by using a site specific recombination system, such as the Gateway® Vector Conversion System (Invitrogen, Paisley, UK).

In a further aspect of the invention, there is provided a HSV comprising an N-terminally truncated glycoprotein D linked to a targeting agent, wherein the N-terminally truncated glycoprotein D does not include a functional HVEM binding domain and may not include a functional nectin-1 binding domain, for use in a therapeutic method of treatment.

In a further aspect of the invention, there is provided a HSV comprising an N-terminally truncated glycoprotein D linked to a targeting agent, wherein the N-terminally truncated glycoprotein D does not include amino acids 1 to 34 of the full-length HSV-1 glycoprotein D, for use in a therapeutic method of treatment. Alternatively, the truncated glycoprotein D may be any truncated glycoprotein D described above.

In a further aspect of the invention, there is provided a HSV comprising nucleic acid encoding a fusion protein, which fusion protein comprises an N-terminally truncated glycoprotein D linked to a targeting agent, wherein the N-terminally truncated glycoprotein D does not include a functional HVEM binding domain and may not include a functional nectin-1 binding domain, for use in a therapeutic method of treatment. The nucleic acid is preferably arranged in the HSV genome such that the HSV is capable of expressing the nucleic acid encoding the fusion protein.

In a further aspect of the invention, there is provided a HSV comprising nucleic acid encoding a fusion protein, which fusion protein comprises an N-terminally truncated glycoprotein D linked to a targeting agent, wherein the N-terminally truncated glycoprotein D does not include amino acids 1 to 34 of the full-length HSV-1 glycoprotein D, for use in a therapeutic method of treatment. Alternatively, the truncated glycoprotein D may be any truncated glycoprotein D described above. The nucleic acid is preferably arranged in the HSV genome such that the HSV is capable of expressing the nucleic acid encoding the fusion protein.

Preferably the therapeutic method of treatment is a method for the treatment of a disease associated with the proliferation of cells, e.g. for treatment of tumour.

In a further aspect of the invention, there is provided use of a HSV in the manufacture of medicament for the treatment of a disease associated with the proliferation of cells, wherein the HSV comprises an N-terminally truncated glycoprotein D linked to a targeting agent, wherein the N-terminally truncated glycoprotein D does not include a functional HVEM binding domain and may not include a functional nectin-1 binding domain, In a further aspect of the invention, there is provided use of a HSV in the manufacture of a medicament for the treatment of a disease associated with the proliferation of cells, wherein the HSV comprises an N-terminally truncated glycoprotein D linked to a targeting agent, wherein the N-terminally truncated glycoprotein D does not include amino acids 1 to 34 of the full-length HSV-1 glycoprotein D. Alternatively, the truncated glycoprotein D may be any truncated glycoprotein D described above.

In a further aspect of the invention, there is provided use of a HSV in the manufacture of a medicament for the treatment of a disease associated with the proliferation of cells, wherein the HSV comprises nucleic acid encoding a fusion protein, which fusion protein comprises an N-terminally truncated glycoprotein D linked to a targeting agent, wherein the N-terminally truncated glycoprotein D does not include a functional HVEM binding domain and may not include a functional nectin-1 binding domain. The nucleic acid is preferably arranged in the HSV genome such that the HSV is capable of expressing the nucleic acid encoding the fusion protein.

In a further aspect of the invention, there is provided use of a HSV, in the manufacture of a medicament for the treatment of a disease associated with the proliferation of cells, wherein the HSV comprises a nucleic acid encoding a fusion protein, which fusion protein comprises an N-terminally truncated glycoprotein D linked to a targeting agent, wherein the N-terminally truncated glycoprotein D does not include amino acids 1 to 34 of the full-length HSV-1 glycoprotein D. Alternatively, the truncated glycoprotein D may be any truncated glycoprotein D described above. The nucleic acid is preferably arranged in the HSV genome such that the HSV is capable of expressing the nucleic acid encoding the fusion protein.

In a further aspect of the invention, there is provided a method of treating a disease associated with the proliferation of cells, comprising administering a HSV, which HSV comprises an N-terminally truncated glycoprotein D linked to a targeting agent, wherein the N-terminally truncated glycoprotein D does not include a functional HVEM binding domain and may not include a functional nectin-1 binding domain.

In a further aspect of the invention, there is provided a method of treating a disease associated with the proliferation of cells, comprising administering a HSV, which comprises an N-terminally truncated glycoprotein D linked to a targeting agent, wherein the N-terminally truncated glycoprotein D does not include amino acids 1 to 34 of the full-length HSV-1 glycoprotein D. Alternatively, the truncated glycoprotein D may be any truncated glycoprotein D described above.

In a further aspect of the invention, there is provided a method of treating a disease associated with the proliferation of cells, comprising administering a HSV, which HSV comprises nucleic acid encoding a fusion protein, which fusion protein comprises an N-terminally truncated glycoprotein D linked to a targeting agent, wherein the N-terminally truncated glycoprotein D does not include a functional HVEM binding domain and may not include a functional nectin-1 binding domain. The nucleic acid is preferably arranged in the HSV genome such that the HSV is capable of expressing the nucleic acid encoding the fusion protein.

In a further aspect of the invention, there is provided a method of treating a disease associated with the proliferation of cells, comprising administering a HSV, which HSV comprises nucleic acid encoding a fusion protein, which fusion protein comprises an N-terminally truncated glycoprotein D linked to a targeting agent, wherein the N-terminally truncated glycoprotein D does not include amino acids 1 to 34 of the full-length HSV-1 glycoprotein D. Alternatively, the truncated glycoprotein D may be any truncated glycoprotein D described above. The nucleic acid is preferably arranged in the HSV genome such that the HSV is capable of expressing the nucleic acid encoding the fusion protein.

In a further aspect of the invention, there is provided a method of producing a HSV, which HSV comprises a N-terminally truncated glycoprotein D linked to a targeting agent, wherein the targeting agent is linked to the N-terminally truncated glycoprotein D as a fusion protein, said method comprising infecting a cell line with said HSV that expresses the fusion protein. The truncated glycoprotein D may be any truncated glycoprotein D described above.

In a further aspect of the invention, there is provided a method of producing an HSV comprising an N-terminally truncated glycoprotein D linked to a targeting agent, wherein the targeting agent is linked to the N-terminally truncated glycoprotein D as a fusion protein, said method comprising incorporating nucleic acid encoding said fusion protein into the viral genome of the modified HSV. The truncated glycoprotein D may be any truncated glycoprotein D described above.

In a further aspect of the invention, there is provided an HSV comprising an N-terminally truncated glycoprotein D linked to a targeting agent,
wherein the position of the truncation is at least at a position corresponding to position 37 of the full-length HSV-1 glycoprotein D,
wherein the extracellular domain of the N-terminally truncated glycoprotein D comprises a portion of amino acids corresponding to amino acids 274-315 of the full-length HSV-1 glycoprotein D,
and wherein the position of the truncation is not at an amino acid position corresponding to a position from 139-239 of the full-length HSV-1 glycoprotein D.

In a further aspect of the invention, there is provided a HSV comprising an N-terminally truncated glycoprotein D linked to a targeting agent,
wherein the position of truncation is at an amino acid position corresponding to a position from 37-128 or from 260-274 of the full-length HSV-1 glycoprotein D.

In all aspects of the invention, the term "N-terminally truncated glycoprotein D" refers to a glycoprotein D that does not include an amino acid corresponding to the N-terminal residue of the full-length HSV-1 glycoprotein D. For example, the N-terminally truncated glycoprotein D is derived from a non-N-terminally truncated glycoprotein D, e.g. the full-length HSV-1 glycoprotein D, by the deletion of at least the N-terminal amino acid. Usually a portion of amino acids will have been deleted, such that an N-terminal region of amino acids is missing compared to the parent glycoprotein D.

As discussed above, we also investigated the possibility of redesigning tropism of HSV by embedding single-chain antibodies (scFv) in the viral envelope via fusion with glycoproteins H and L. Glycoproteins H and L form a heterodimer with both proteins required for its correct folding and membrane presentation. We demonstrate here that linking an scFv to the N terminus of glycoprotein H and another scFv to the N-terminus of glycoprotein L redirects the tropism of HSV.

To the best of our knowledge, this is the first description of the construction of receptor-binding fusion proteins based on the glycoprotein H/glycoprotein L heterodimer. This discovery thus opens up an unexpected route for redirecting the tropism of HSV.

Accordingly, in a further aspect of the invention, there is provided a herpes simplex virus (HSV) comprising:
a. a glycoprotein H linked to a first targeting agent, and
b. a glycoprotein L linked to a second targeting agent,
wherein the first targeting agent and the second targeting agent are specific for the same target.

In a further aspect of the invention, there is provided a HSV comprising:
a. nucleic acid encoding a first fusion protein, which first fusion protein comprises a glycoprotein H linked to a first targeting agent, and b. nucleic acid encoding a second fusion protein, which second fusion protein comprises a glycoprotein L linked to a second targeting agent, wherein the first targeting agent and the second targeting agent are specific for the same target. The nucleic acid encoding the first fusion protein and/or the nucleic acid encoding the second fusion protein is preferably arranged in the HSV genome such that the HSV is capable of expressing the nucleic acid encoding the fusion protein.

The first targeting agent is preferably linked to the N-terminus of the glycoprotein H polypeptide, optionally with one or more spacer molecules between the N-terminus and the first targeting agent. Likewise, the second targeting agent is preferably linked to the N-terminus of the glycoprotein L, optionally with one or more spacer molecules between the N-terminus and the second targeting agent. However, it is preferred that the there is no spacer molecule between the glycoprotein H and the targeting agent. Without being bound by theory, it was thought that a spacer between the glycoprotein L and the scFv might provide a flexible arm allowing the scFv at the N terminus of glycoprotein L to interact and dimerise with the scFv at the N terminus of glycoprotein H.

The spacer molecule may be any molecule that includes appropriate chemical functional groups to allow its attachment to both the glycoprotein and a targeting agent. For example, a spacer molecule may be a peptide. A suitable peptide may be Gly-Gly-Gly-Gly-Ser. One or more of these molecules may be inserted between the glycoprotein N-terminus and a targeting agent.

Preferably a spacer molecule is between the N-terminus of the glycoprotein L polypeptide and the second targeting agent. The spacer molecule may be a 1-20 amino acid polypeptide, a 1-15 amino acid polypeptide, a 1-10 amino acid polypeptide, or even a 1-5 amino acid polypeptide. For example, the spacer molecule may be a 3-18 amino acid polypeptide, a 5-15 amino acid polypeptide, or a 5-10 amino acid polypeptide. The spacer molecule may be a polypeptide comprising or consisting of 1 or more units of the polypeptide Gly-Gly-Gly-Gly-Ser, for example, 1, 2, 3, or 4 units. Preferably the spacer molecule comprises or consists of 1 or 2 units of Gly-Gly-Gly-Gly-Ser, most preferably 1 unit.

Nucleic acid encoding any fusion protein of the invention may be inserted in the HSV genome such that is it capable of being transcribed. The nucleic acid may be operably linked to a suitable regulatory sequence (e.g. a promoter), the activity of which may be constitutive or may be controlled by the availability of a signal molecule. The promoter may be, for example, an endogenous HSV promoter such as the gC promoter, or a non endogenous promoter such as the CMV-IE promoter.

The glycoprotein H and glycoprotein L molecules are not limited to any particular glycoprotein H and glycoprotein L, although preferably they are capable of forming a heterodimer, e.g. they are derived from the same species of HSV. Rather, the invention covers any glycoprotein H and glycoprotein L, such as the following list of glycoprotein NCBI database entries:

Glycoprotein H:
Human HSV-1: NC_001806.1 GI:9629378; AAG17895.1 GI:10444402
Human HSV-2: NC_001798.1 GI:9629267; 286099.2 GI:6572414
Human HSV-5: YP_081523.1 GI:52139248
Human HSV-6: X83413.1 GI:853961; X64320.1 GI:296190; AB021506.1 GI:4995977
Ovine HSV-2: NC_007646.1 GI:83642839; AY839756.1 GI:61970953
Gallid HSV-2: DQ530348.1 GI:104303917
Bovine HSV-1: Z78205.1 GI:1491620
Equine HSV-1: AY464052.1 GI:42795127
Murid HSV-1: NC_004065.1 GI:21716071
Alcelaphine HSV-1: NC_002531.1 GI:10140926
Suid HSV-1: DQ993360.1 GI:116272035
Saimiriine HSV-2: D00400.1 GI:221845
Cercopithecine HSV-9: AAB04139.1 GI:833831
Glycoprotein L:
Human HSV-1: NP_044602.1 GI:9629381;
Human HSV-2: NP_044470.1 GI:9629270
Human HSV-5: YP_081555.1 GI:52139280; AAR31659.1 GI:39842115
Human HSV-6: NC_001664.1 GI:9628290
Murid HSV-1: NC_004065.1 GI:21716071

Other glycoprotein H and L may be identified using the hybridisation and probe techniques as described below. However, it is preferred that the glycoprotein H and L of the invention are glycoprotein H and L for which a database accession number is provided. More preferably, the glycoprotein H and L of the invention are from a human strain of HSV, in particular HSV-1 or HSV-2, even more preferably HSV-1. Most preferably the glycoprotein H and L is derived from HSV-1 strain 17 or F, e.g. the strain F glycoprotein H and L under NCBI database accession number X14112.1 (GI: 1944536), which are SEQ ID NO: 2 and SEQ ID NO: 3 respectively. Accordingly, nucleic acid encoding the glycoprotein H may comprise the nucleic acid sequence of SEQ ID NO: 5, and nucleic acid encoding the glycoprotein L may comprise the nucleic acid sequence of SEQ ID NO: 6.

In a further aspect of the invention, there is provided a first fusion protein, which fusion protein comprises a glycoprotein H linked to a targeting agent. In a further aspect of the invention, there is provided a second fusion protein, which second fusion protein comprises a glycoprotein L linked to a targeting agent. The first fusion protein and the second fusion protein may have specific affinity for each other, for example they may form a heterodimer.

In a further aspect of the invention, there is provided a nucleic acid molecule encoding a fusion protein, which fusion protein comprises a glycoprotein H linked to a targeting agent. In a further aspect of the invention, there is provided a nucleic acid molecule comprising nucleic acid encoding a fusion protein, which fusion protein comprises a glycoprotein L linked to a targeting agent.

A single nucleic acid molecule may include a nucleic acid region encoding the first fusion protein and nucleic acid region encoding the second fusion protein. Alternatively the first fusion protein and second fusion protein may be encoded by separate nucleic acid molecules. The nucleic acid encoding the first fusion protein and/or the nucleic acid encoding the second fusion protein may be arranged in the nucleic acid molecule such that it is operably linked to a suitable regulatory sequence (e.g. a promoter). A promoter may be constitutive or may be controlled by the availability of a signal molecule. The promoter may be, for example, an endogenous HSV promoter such as the gC promoter, or a non endogenous promoter such as the CMV-IE promoter. The nucleic acid molecule may also include nucleic acid for facilitating insertion of the nucleic acid encoding the fusion protein into the genome of a HSV. Said insertion may be, for example, by homologous recombination, or by using a site specific recombination system, such as the Gateway® Vector Conversion System (Invitrogen, Paisley, UK).

In a further aspect of the invention, there is provided a HSV comprising:
a. a glycoprotein H linked to a first targeting agent, and
b. a glycoprotein L linked to a second targeting agent,
wherein the first targeting agent and the second targeting agent are specific for the same target,
and wherein the HSV is for use in a therapeutic method of medical treatment.

In a further aspect of the invention, there is provided a HSV comprising:
a. nucleic acid encoding a first fusion protein, which first fusion protein comprises a glycoprotein H linked to a first targeting agent, and
b. nucleic acid encoding a second fusion protein, which second fusion protein comprises a glycoprotein L linked to a second targeting agent,
wherein the first targeting agent and the second targeting agent are specific for the same target,
and wherein the HSV is for use in a therapeutic method of medical treatment. The nucleic acid encoding the first fusion protein and/or the nucleic acid encoding the second fusion protein is preferably arranged in the HSV genome such that the HSV is capable of expressing the nucleic acid encoding the fusion protein.

Preferably the therapeutic method of treatment is a method for the treatment of a disease associated with the proliferation of cells, e.g. for treatment of tumour.

In a further aspect of the invention, there is provided use of a herpes simplex virus in the manufacture of medicament for the treatment of a disease associated with the proliferation of cells, wherein the HSV comprises:
a. a glycoprotein H linked to a first targeting agent, and
b. a glycoprotein L linked to a second targeting agent,
wherein the first targeting agent and the second targeting agent are specific for the same target.

In a further aspect of the invention, there is provided use of a HSV in the manufacture of medicament for the treatment of a disease associated with the proliferation of cells, wherein the HSV comprises:
a. nucleic acid encoding a first fusion protein, which first fusion protein comprises a glycoprotein H linked to a first targeting agent, and
b. nucleic acid encoding a second fusion protein, which second fusion protein comprises a glycoprotein L linked to a second targeting agent,
and wherein the first targeting agent and the second targeting agent are specific for the same target. The nucleic acid encoding the first fusion protein and/or the nucleic acid encoding the second fusion protein is preferably arranged in the HSV genome such that the HSV is capable of expressing the nucleic acid encoding the fusion protein.

In a further aspect of the invention, there is provided a method of treating a disease associated with the proliferation of cells, comprising administering a HSV, wherein the HSV comprises:
a. a glycoprotein H linked to a first targeting agent, and
b. a glycoprotein L linked to a second targeting agent,
wherein the first targeting agent and the second targeting agent are specific for the same target.

In a further aspect of the invention, there is provided a method of treating a disease associated with the proliferation of cells, comprising administering a HSV, wherein the HSV comprises:
a. nucleic acid encoding a first fusion protein, which first fusion protein comprises a glycoprotein H linked to a first targeting agent, and
b. nucleic acid encoding a second fusion protein, which second fusion protein comprises a glycoprotein L linked to a second targeting agent,
and wherein the first targeting agent and the second targeting agent are specific for the same target. The nucleic acid encoding the first fusion protein and/or the nucleic acid encoding the second fusion protein is preferably arranged in the HSV genome such that the HSV is capable of expressing the nucleic acid encoding the fusion protein.

In a further aspect of the invention, there is provided a method of producing a HSV comprising:
a. a glycoprotein H linked to a first targeting agent, and
b. a glycoprotein L linked to a second targeting agent,
wherein the first targeting agent and the second targeting agent are specific for the same target,
said method comprising infecting a cell line with said HSV that expresses the fusion protein.

In a further aspect of the invention, there is provided a method of producing an HSV comprising:
a. a glycoprotein H linked to a first targeting agent, and
b. a glycoprotein L linked to a second targeting agent,
wherein the first targeting agent and the second targeting agent are specific for the same target,
said method comprising incorporating nucleic acid encoding said fusion protein into the viral genome of the modified HSV.

Truncated Glycoprotein D Variants

The N-terminally truncated glycoprotein D molecules of the invention may or may not also include one or more further amino acid deletions, and/or may or may not include one or more amino acid substitutions or insertions compared to the non-truncated glycoprotein D molecule from which it is derived. Thus, although the truncated glycoprotein D will usually contain fewer amino acids than the non-truncated glycoprotein D, in some cases it may contain the same number or more amino acids compared to the non-truncated glycoprotein D molecule. Preferably, such amino acid deletions, substitutions, or insertions do not result in any adverse functional dissimilarity compared to the glycoprotein D having the same N-terminal truncation and which does not contain the one or more deletions, substitutions or insertions.

Preferably, the identity of the amino acid sequence of the extracellular domain of the truncated glycoprotein D is substantially equivalent to the amino acid sequence of the non-truncated glycoprotein D from which the truncated glycoprotein D is derived. Preferably the truncated glycoprotein is derived from the glycoprotein D sequence under NCBI database accession number X14112.1 (GI:1944536), which is SEQ ID NO: 1. The truncated glycoprotein D may be derived from a glycoprotein D encoded by the nucleic acid sequence of SEQ ID NO: 4.

For example, the extracellular domain of the truncated glycoprotein D sequence may display a sequence identity of at least 70%. Alternatively, this identity may be any of 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% sequence identity. The region of the extracellular domain of the non-truncated glycoprotein D that has been deleted in the truncated glycoprotein D is not taken into account when determining sequence identity.

Alternatively, identity may be determined over the whole glycoprotein D sequence, i.e. not just the extracellular domain.

Thus, where the sequence identity of the glycoprotein D truncate is 100% compared to SEQ ID NO: 1 and the full-length glycoprotein D is SEQ ID NO: 1, as is preferred, the amino acid corresponding to a position of interest in the HSV-1 glycoprotein D full-length sequence will be identical to the corresponding amino acid in the full-length sequence. Likewise, amino acids in the truncate that correspond to a portion of amino acids in the full-length sequence will be identical to the portion of corresponding amino acids in the full-length sequence.

In case of doubt, the non-truncated glycoprotein D from which the truncated glycoprotein D is derived is the glycoprotein D listed above that has the closest sequence identity with the truncated glycoprotein D, not taking into account th'e truncated region.

Glycoprotein H and Glycoprotein L Variants

Likewise, the glycoprotein H and/or L of the invention may or may not include one or more amino acid deletions, substitutions or insertions compared to the wild-type glycoprotein H and/or L from which each is derived. Preferably, such amino acid deletions, substitutions or insertions do not result in any adverse functional dissimilarity compared to the glycoprotein H and/or L from which each is derived.

Preferably, the identity of the amino acid sequence of the glycoprotein H and/or L is substantially equivalent to the amino acid sequence of the glycoprotein H and/or L from which each is derived. For example, the glycoprotein H and/or L sequence may display a sequence identity of at least 70%. Alternatively, this identity may be any of 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% sequence identity.

Targeting Agents

The targeting agent is conveniently an antibody or component of an antibody, e.g. an antibody binding domain such as a single chain variable fragment (scFv). The targeting agent is preferably capable of specifically binding to a cell surface protein present of the cell type targeted. This is discussed below. The targeting agent is preferably bound to the glycoprotein D, H, or L such that it forms a fusion protein with the glycoprotein. Alternatively, the targeting agent may be bound to the viral particle by chemical means, e.g. covalently, or by a binding agent. For example, the binding agent may bind directly to the glycoprotein D, H, or L of the invention. Alternatively, the binding agent may bind to a cognate ligand linked to the glycoprotein, e.g. avidin/strepavidin and biotin. Preferably the targeting agent is linked to the N-terminus of the glycoprotein, i.e. the N-terminally truncated glycoprotein D, glycoprotein H and/or glycoprotein L.

As an antibody binding domain forms a preferred embodiment of the invention, the following description will concentrate on the use of antibodies. However, it will be apparent to the skilled person that other targeting agents may be used, e.g. aptamers, or members of a specific binding pair such as a receptor and its ligand.

The antibody or antibody component incorporated into the viral envelope influences the selectivity of the virus by enhancing the efficiency of viral infection of a certain cell type or cell types. In other words, by displaying a targeting agent that is specific for a particular cell surface protein, the virus preferentially infects cells displaying that cell surface protein. The HSV is thereby targeted to that cell type, in as much as it has increased binding affinity for the cell type, resulting in increased levels of infection of that cell type. Other cell types may still be infected by the HSV. The HSV infection process is initiated through contact between glycoproteins of the viral envelope and glycoproteins of the target cell membrane. In the present invention, antibodies with specific affinity for membrane proteins of the chosen cell type are attached to a truncated glycoprotein D, and/or a glycoprotein H and a glycoprotein L, and are thereby incorporated into the HSV viral envelope. This increases the affinity of the HSV for the surface of the chosen target cell through the additional interaction between the antibody and the cell surface protein. The binding of the antibody binding domain to its target antigen on the cell surface will bring both virion and cellular membranes into closer proximity and allow the viral envelope glycoproteins to initiate fusion of the membranes, leading to penetration of the cell.

Preferably, the antibody or antibody component is specific for a tumour cell surface antigen, i.e. an antigen found on the surface of a tumour cell and associated with that cell, being either unique to tumour cells or being more abundant on tumour cells than on most if not all non-tumour cells. Many novel or atypical forms of normal proteins are expressed by tumour cells, and antibodies directed against these provide tumour targeting strategies. For example, carcinoembryoinic antigen (CEA) is an important marker on many tumour cells and engineered antibodies directed against CEA have undergone clinical trials (Mayer, A. et al., *J. Immunol. Methods* 231 261-273 (1999)). Engineered antibodies directed against the Her2/neu growth factor (Trastuzamab) and against CD20 (rituximab) have been licensed for the treatment of breast cancer and Non-Hodgkin's lymphoma respectively Holliger, P. and Hoogenboom, H. (1998), Nature Biotechnology 16, 1015. CD55 (decay accelerating factor) is over-expressed by tumour cells to block complement activation and antibodies directed against CD55 may have therapeutic potential (Li, L. et al. *B. J. Cancer* 84 (1) 80-86 (2001)). CD38 is well represented on the cell surfaces of a variety of lymphoid tumours and is considered to be a promising target for antibody therapy (Stevenson, Mol. Med. (12) 345-346 (2006). EGFR is also considered to be a valid target in the treatment of solid tumours and is overexpressed in many tumour types (Wujcik, Seminars in Oncology Nursing, (22) 5-9 (2006)). Thus, the antibody or antibody component may be specific for a target selected from the group consisting of GD3, CD38, CD55, CD20, EGRF, HER2/neu, CEA, squamous cell carcinoma antigens 1 and 2, ovarian carcinoma antigen CA125, Mucin 1, prostate-specific membrane antigen, melanoma-associated tumour antigen p97, 5T4 oncofoetal trophoblast glycoprotein, PLAC1, CA19-9, CA72-4 and CA195.

The antibody binding domain may have specific affinity for a cell surface protein found on the cell type from which the tumour originated, e.g. in the case of a breast cancer, the antibody or antibody component incorporated into the HSV viral envelope would be specific for an antigen commonly associated with breast cancer cells, e.g. Her2/Neu. The specificity of the avirulent HSV strain for infecting dividing cells would therefore be further modified so that breast cancer cells were preferentially infected by the virus more than other types of dividing cells. By targeting dividing breast cancer cells, the HSV should infect and lyse breast cancer cells more efficiently than any other cells. The use of antibodies or antibody components against particular cell types can also be used to extend the tropism of HSV to cell types that are not otherwise efficiently infected by HSV, e.g. the use of antibodies or antibody components specific for antigen found on B cells would be expected to extend the tropism of HSV to B cells. Antibodies or antibody components of different specificities may be included together in one HSV viral envelope. In view of the results reported here, the combination of these specificities would be expected to give greater specificity of targeting to the desired cell type.

HSV Strains

Preferably the HSV is non-neurovirulent. The HSV is also preferably oncolytic. More preferably the HSV is modified in at least one of the long repeat regions ($R_L$) of the HSV genome, relative to the genome of the corresponding wild-type strain, such that the HSV lacks neurovirulence. The modification may be within the BamHI s restriction fragment of one or each $R_L$ repeat. As such, the HSV genome may be modified within the Bam HI s region of the internal repeat $R_L$ (0.81-0.83 mu) and within the counterpart region of the terminal $R_L$ (0-0.02 mu) such that the variant lacks neurovirulence.

Such modification may take the form of at least one addition, deletion, substitution or insertion of one or more nucleotides.

In one arrangement the genome is modified in each said region, e.g. by a deletion of one or more nucleotides. The deletion may be of at least 50 or at least 100 nucleotides or from 0.5 Kb to 3 Kb or from 0.7 Kb to 2.5 Kb. In one arrangement the deletion is 759 bp in length and is located between nucleotide positions 125213 and 125972 of the internal long repeat ($IR_L$) and in the counterpart region of the terminal long repeat ($TR_L$) of HSV-1 strain 17.

Suitable modifications may also include the insertion of an exogenous nucleic acid sequence or exogenous/heterologous cassette comprising said sequence into the herpes simplex virus genomic DNA. The insertion may be performed by homologous recombination, or by site-specific recombination using an HSV genome with appropriate recombination sites, of the exogenous nucleic acid sequence into the genome of the selected herpes simplex virus. For example, the modification may take the form of insertion of a sequence of nucleotides encoding a gene product, such as a fusion protein of the invention, which may be operably linked to one or more control sequences enabling expression of the gene product from the HSV vector.

Where a plurality of nucleotides are inserted, e.g. in the case of insertion of a gene sequence, the inserted nucleotides may be located entirely within, or may overlap, at least one of the ICP34.5 protein coding sequences of the HSV genome. The inserted nucleic acid may be located in both (this will usually be all) copies of the RL1 locus or ICP34.5 protein coding sequence.

The HSV may, therefore, have an inactivating mutation in the RL1 locus of the HSV genome, more specifically a mutation which inactivates the function of the ICP34.5 gene product, such that the herpes simplex virus does not produce a functional ICP34.5 gene product and is non-neurovirulent.

Accordingly, an inactivating mutation may be present in one or each ICP34.5 locus, disrupting the ICP34.5 protein coding sequence such that the ICP34.5 gene is non-functional and cannot express a functional ICP34.5 gene product.

Preferably, both copies of the ICP34.5 gene sequence contain inactivating mutations, which may be the result of one or more modifications of the HSV genome, as described above.

Preferably, the HSV is a null mutant and as such is not capable of producing a functional ICP34.5 protein. Such null mutants may contain modifications in both copies of the ICP34.5 gene present in the viral genome such that the virus is unable to express functional ICP34.5 protein. Preferably, the HSV does not comprise nucleic acid, e.g. an ICP34.5 gene, that encodes a functional ICP34.5 gene product.

The HSV may be a mutant of HSV-1 or HSV-2, more preferably of one of HSV-1 strains 17, F or HSV-2 strain HG52 and most preferably of HSV-1 strain 17. Non-neurovirulent ICP34.5 null mutants of HSV-1 strain 17 are particularly preferred and suitable examples include:
(a) HSV 1716 (ECACC accession number V92012803); and
(b) HSV 1790 (ECACC accession number 03110501).

The HSV may be a further mutant of HSV 1716 or HSV 1790.

Suitable HSV may therefore be described as mutants or variants of the parent HSV strain from which they are derived or to which they correspond. For example, HSV 1716 and HSV 1790 are mutants of HSV-1 strain 17 and may be obtained by modification of the strain 17 genomic DNA. Suitable mutant HSV may be non-wild type and may be recombinant. Mutant herpes simplex viruses may comprise a genome containing modifications relative to the wild type, as described above.

In this specification, non-neurovirulence is defined by the ability to introduce a high titre of virus (approx $10^6$ plaque forming units (pfu)) to an animal or patient without causing a lethal encephalitis such that the $LD_{50}$ in animals, e.g. mice, or human patients is in the approximate range of $\geq 10^6$ pfu.

Where the HSV comprises a truncated glycoprotein D linked to a targeting agent as described above, the HSV may be engineered, e.g. by mutation, such that it does not express a non-truncated glycoprotein D, e.g. the endogenous glycoprotein D. Likewise, where the HSV comprises a glycoprotein H and/or L linked to a targeting agent as described above, the HSV may be engineered, e.g. by mutation, such that it does not express the endogenous glycoprotein H and/or L.

Nucleic Acid

In further aspects of the present invention a nucleic acid vector is provided which comprises, or encodes, a nucleic acid of the invention. The vector may preferably be a transcription vector from which a nucleic acid of the invention may be expressed. In preferred embodiments the vector may be a Herpes Simplex Virus (HSV). The HSV genome may be modified to encode a nucleic acid of the invention which may be transcribed and expressed when the HSV infects a cell, preferably a mammalian cell. The HSV genome may further encode a polypeptide of interest capable of expression upon infection of a cell by the HSV. Alternatively the vector may be a vector for propagating the nucleic acid, e.g. in E. coli.

In this specification the term "operably linked" may include the situation where a nucleic acid and regulatory nucleotide sequence are covalently linked in such a way as to place the expression of the nucleic acid under the influence or control of the regulatory sequence. Thus a regulatory sequence is operably linked to a nucleic acid if the regulatory sequence is capable of effecting transcription of the nucleic acid of the invention. The regulatory sequence may, for example, be a component of a promoter system.

Where HSV is specified as comprising nucleic acid, the nucleic acid is preferably part of the HSV genome. The nucleic acid may be arranged in the HSV genome such that the HSV is capable of expressing the nucleic acid. Nucleic acid encoding a glycoprotein, truncate thereof, and/or targeting agent, preferably refers to an open reading frame, e.g. a gene, that encodes said glycoprotein, truncate thereof, or targeting agent. The nucleic acid is preferably DNA.

Fusion Proteins

A fusion protein comprising a glycoprotein, or N-terminally truncated glycoprotein, and targeting agent of the invention comprises a polypeptide chain that incorporates the polypeptide chain of the glycoprotein, or truncate thereof, and the polypeptide chain of the targeting agent, e.g. they are contiguous. Normally the glycoprotein, or truncate thereof, and the targeting agent will be arranged in the fusion protein such that the glycoprotein, or truncate thereof, is on the C-terminal side of the targeting agent.

The fusion protein may or may not comprise one or more amino acids between the last amino acid (N-terminal amino acid) of the glycoprotein, or truncate thereof, and the first amino acid (C-terminal amino acid) of the targeting agent. For example, the N-terminal amino acid of the glycoprotein, or truncate thereof, may abut the C-terminal amino acid of the targeting agent, e.g. they are immediately adjacent. Alternatively the glycoprotein, or truncate thereof, may be separated by a spacer peptide or spacer polypeptide.

The nucleic acid encoding the fusion protein may be a single open reading frame, e.g. a single gene. Thus, the glycoprotein or truncate and the targeting agent may be transcribed and translated together, e.g. they may be transcribed onto the same mRNA molecule and translated such that they are provided on the same polypeptide chain.

In general, a fusion protein may be created via genetic engineering from two or more proteins/peptides. This may be achieved by creating a fusion gene, e.g. by removing the stop codon from a first gene encoding a first protein and appending it to a second gene encoding a second protein in frame. A linker region, e.g. nucleic acid encoding one or more additional peptides, may be inserted between the two genes to facilitate correct folding of the fusion protein.

The term "fusion protein" is herein used interchangeably with the term "fusion polypeptide".

Sequence Identity

Percentage (%) sequence identity is defined as the percentage of amino acid residues in a candidate sequence that are identical with residues in the given listed sequence (referred to by the SEQ ID No.) after aligning the sequences and introducing gaps if necessary, to achieve the maximum sequence identity, and not considering any conservative substitutions as part of the sequence identity. Unless otherwise indicated, sequence identity is preferably calculated over the entire length of the respective sequences.

Unless otherwise indicated, where the aligned sequences are of different length, sequence identity of the shorter comparison sequence may be determined over the entire length of the longer given sequence or, where the comparison sequence is longer than the given sequence, sequence identity of the comparison sequence may be determined over the entire length of the shorter given sequence.

For example, where a given sequence comprises 100 amino acids and the candidate sequence comprises 10 amino acids, the candidate sequence can only have a maximum identity of 10% to the entire length of the given sequence. This is further illustrated in the following example:

```
(A)
Given seq:         XXXXXXXXXXXXXXX   (15 amino acids)

Comparison seq:    XXXXXYYYYYYY      (12 amino acids)
```

% sequence identity=the number of identically matching amino acid residues after alignment divided by the total number of amino acid residues in the longer given sequence, i.e. (5 divided by 15)×100=33.3%

Where the comparison sequence is longer than the given sequence, sequence identity may be determined over the entire length of the given sequence. For example:

```
(B)
Given seq:         XXXXXXXXXX                (10 amino acids)

Comparison seq: XXXXXYYYYYYZZYZZZZZZ (20 amino acids)
```

% sequence identity=number of identical amino acids after alignment divided by total number of amino acid residues in the given sequence, i.e. (5 divided by 10)×100=50%.

Alignment for purposes of determining percent amino acid sequence identity can be achieved in various ways known to a person of skill in the art, for instance, using publicly available computer software such as BLAST, BLAST-2, ALIGN or Megalign (DNASTAR) software.

Hybridisation

In accordance with the present invention, glycoprotein D, H and L nucleic acid sequences may be identified by using hybridization and washing conditions of appropriate stringency.

Complementary nucleic acid sequences will hybridise to one another through Watson-Crick binding interactions. Sequences which are not 100% complementary may also hybridise but the strength of the hybridisation usually decreases with the decrease in complementarity. The strength of hybridisation can therefore be used to distinguish the degree of complementarity of sequences capable of binding to each other.

The "stringency" of a hybridization reaction can be readily determined by a person skilled in the art.

The stringency of a given reaction may depend upon factors such as probe length, washing temperature, and salt concentration. Higher temperatures are generally required for proper annealing of long probes, while shorter probes may be annealed at lower temperatures. The higher the degree of desired complementarity between the probe and hybridisable sequence, the higher the relative temperature which can be used. As a result, it follows that higher relative temperatures would tend to make the reaction conditions more stringent, while lower temperatures less so.

For example, hybridizations may be performed, according to the method of Sambrook et al., ("Molecular Cloning, A Laboratory Manual, Cold Spring Harbor Laboratory Press, 1989) using a hybridization solution comprising: 5×SSC, 5×Denhardt's reagent, 0.5-1.0% SDS, 100 μg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 1×SSC and 1% SDS; (4) 2 hours at 42-65° C. in 1×SSC and 1% SDS, changing the solution every 30 minutes.

One common formula for calculating the stringency conditions required to achieve hybridization between nucleic acid molecules is to calculate the melting temperature $T_m$ (Sambrook et al., 1989):

$$T_m = 81.5° C. + 16.6 \log[Na+] + 0.41(\% G+C) - 0.63(\% \text{formamide}) - 600/n$$

where n is the number of bases in the oligonucleotide.

As an illustration of the above formula, using [Na+]=[0.368] and 50% formamide, with GC content of 42% and an average probe size of 200 bases, the $T_m$ is 57° C. The $T_m$ of a DNA duplex decreases by 1-1.5° C. with every 1% decrease in sequence complementarity.

Accordingly, nucleotide sequences can be categorised by an ability to hybridise to a target sequence under different hybridisation and washing stringency conditions which can be selected by using the above equation. The $T_m$ may be used to provide an indicator of the strength of the hybridisation.

The concept of distinguishing sequences based on the stringency of the conditions is well understood by the person skilled in the art and may be readily applied.

Treatment

The present invention provides HSV for use in a method of medical treatment. Preferably they are provided for use in the treatment of a disease associated with the proliferation of cells, such as a cancerous condition, i.e. in oncotherapy. This treatment may comprise the oncolytic treatment of the cancer, which may take the form of a tumour. Accordingly, the method of treatment may involve the killing of tumour cells by the HSV. Treatment may involve the selective infection and/or lysis of dividing cells. The use of HSV in the manufacture of a medicament, pharmaceutical composition or vaccine for the treatment of cancer is also provided. Such medicaments, pharmaceutical compositions or vaccines may comprise suitable HSV together with a pharmaceutically acceptable carrier, adjuvant or diluent.

In this specification a cancerous condition may be any unwanted cell proliferation (or any disease manifesting itself by unwanted cell proliferation), neoplasm or tumour. The cancerous condition may be a cancer and may be a benign or malignant cancer and may be primary or secondary (metastatic). A neoplasm or tumour may be any abnormal growth or proliferation of cells and may be located in any tissue. Examples of tissues include the colon, pancreas, lung, breast, uterus, stomach, kidney, testis, central nervous system (including the brain), peripheral nervous system, skin, blood or lymph.

Tumours to be treated may be nervous system tumours originating in the central or peripheral nervous system, e.g. glioma, medulloblastoma, meningioma, neurofibroma, ependymoma, Schwannoma, neurofibrosarcoma, astrocytoma and oligodendroglioma, or may be non-nervous system tumours originating in non-nervous system tissue e.g. melanoma, mesothelioma, lymphoma, hepatoma, epidermoid carcinoma, prostate carcinoma, breast cancer cells, lung cancer cells or colon cancer cells. HSV of the present invention may be used to treat metastatic tumours occurring in the central or peripheral nervous system which originated in a non-nervous system tissue or metastatic tumours occurring outside the central or peripheral nervous system which originated in a central or peripheral nervous system tissue.

Formulation and Administration

Medicaments and pharmaceutical compositions according to aspects of the present invention may be formulated for administration by a number of routes, including but not limited to, systemic, parenteral, intravenous, intra-arterial, intramuscular, intraperitoneal. The medicaments and compositions may be formulated in fluid or solid form. Fluid formulations may be formulated for administration by injection to a selected region of the human or animal body.

The HSV may be administered systemically, parenterally, intravenously, intra-arterially, intramuscularly, intrathecally, subcutaneously. Any one of these routes of administration may involve injection of the HSV. Injectable formulations may comprise the HSV in a sterile and/or isotonic medium.

The route of administration may be selected by the ability of that route to expose substantially the entire body to the HSV. This may be determined by the ability of the HSV to circulate throughout substantially all parts of the body via the selected route. Circulation throughout substantially all of the body may exclude exposure of the HSV to one or a small number of tissues. For example, where the HSV is circulated in the blood it may be excluded from the brain by the blood brain barrier.

In preferred embodiments of the invention the HSV is administered by injection to the circulating blood, e.g. by intravenous or intra-arterial injection.

The delivery of suitable HSV to cancerous cells that are to be treated may be performed using naked virus or by encapsulation of the virus in a carrier, e.g. in nanoparticles, liposomes or other vesicles.

Administration is preferably in a "therapeutically effective amount", this being sufficient to show benefit to the individual. The actual amount administered, and rate and time-course of administration, will depend on the nature and severity of the tumour being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

The HSV may be administered at any therapeutically effective dosage amount. Therapeutically effective dosages may comprise less than or equal to one of $10^3$, $10^4$, $10^5$, $10^6$, $10^7$, $10^8$ or $10^9$ plaque forming units (pfu).

The patient to be treated may be any animal or human. The patient may be a non-human mammal, but is more preferably a human patient. The patient may be male or female.

The invention includes the combination of the aspects and preferred features described, except where such a combination is clearly impermissible or expressly avoided. In particular, all aspects relating to glycoprotein D may be combined with each other, and all aspects relating to glycoprotein H and L may be combined with each other.

Aspects and embodiments of the present invention will now be illustrated, by way of example, with reference to the accompanying Figures. Further aspects and embodiments will be apparent to those skilled in the art. All documents mentioned in this text are incorporated herein by reference.

BRIEF DESCRIPTION OF THE FIGURES

Embodiments and experiments illustrating the principles of the invention will now be discussed with reference to the accompanying Figures in which.

(a) shows plasmid sp73 with PGK-gfp and gCp-scFv/gD expression cassettes. (b) shows plasmid RL1-del used for homologous recombination reactions with flanking RL1 sequences and PGK-gfp and gCp-scFv/gD expression cassettes inserted within the ICP34.5 deleted region. Viruses derived from this plasmid by homologous recombination will have the same structure at RL1. (c) shows plasmid sp73 with PGK-gfp, gCp-scFv/gL and TKp-scFv/gH expression cassettes. (d) shows plasmid RL1-del used for homologous recombination reactions with flanking RL1 sequences and PGK-gfp, gCp-scFv/gL and TKp-scFv/gH expression cassettes inserted within the ICP34.5 deleted region. Viruses derived from this plasmid by homologous recombination will have the same structure at RL1. (e) shows structure at the RL1 loci of HSV1716GateRed with attR site-specific recombination sequences flanking a CMV-DsRed expression cassette. (f) shows plasmid pENTR1A-gfp with attL site-specific recombination sequences flanking PGK-gfp and CMV-scFv/gD expression cassettes. (g) shows product from site-specific recombination between (e) and (f) generates PGK-gfp and CMV-scFv/gD expression cassettes in the RL1 loci of the HSV1716 recombinant.

Figure 7:
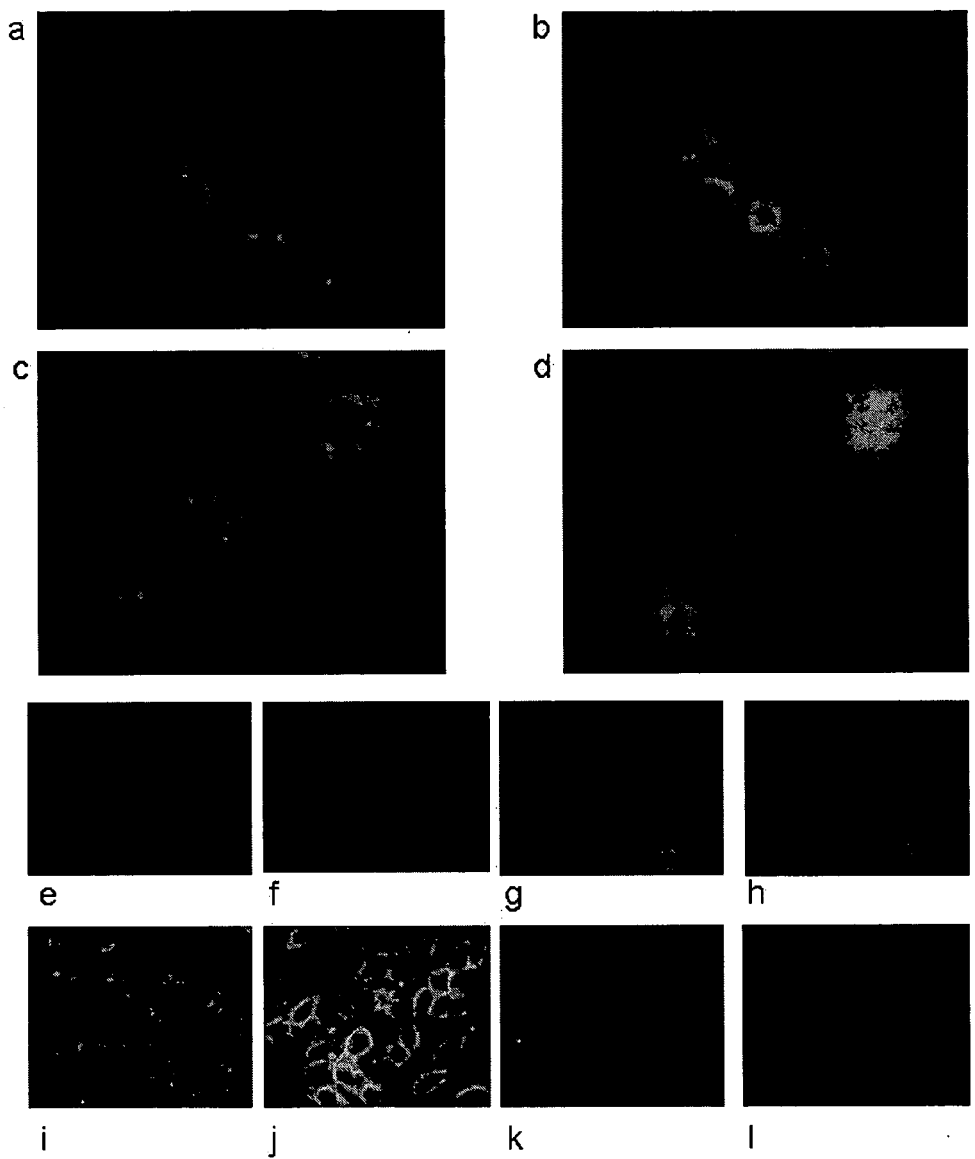

FIG. 7 shows the results of immunofluorescence experiments, demonstrating localisation of scFv/gH fusion proteins (a-d) during infection of BHK cells with HSV1716 variants expressing scFvT (a and c) or scFv5 (c and d). HA-tag staining is shown in a and c and gfp fluorescence in d and e. Immunofluorescence with MabT (e and g) or Mab5 (f and h) demonstrating expression of CD38 but not CD20 by SupT cells (e and f) and CD38 and weak CD20 expression by TolB cells (g and h). Immunofluorescence with MabB (i and k) and a recombinant minibody version of MabB (j and l) demonstrating expression of DAF by CHO/DAF (i and j) but not by normal CHO (k and l) cells.

Figure 8:
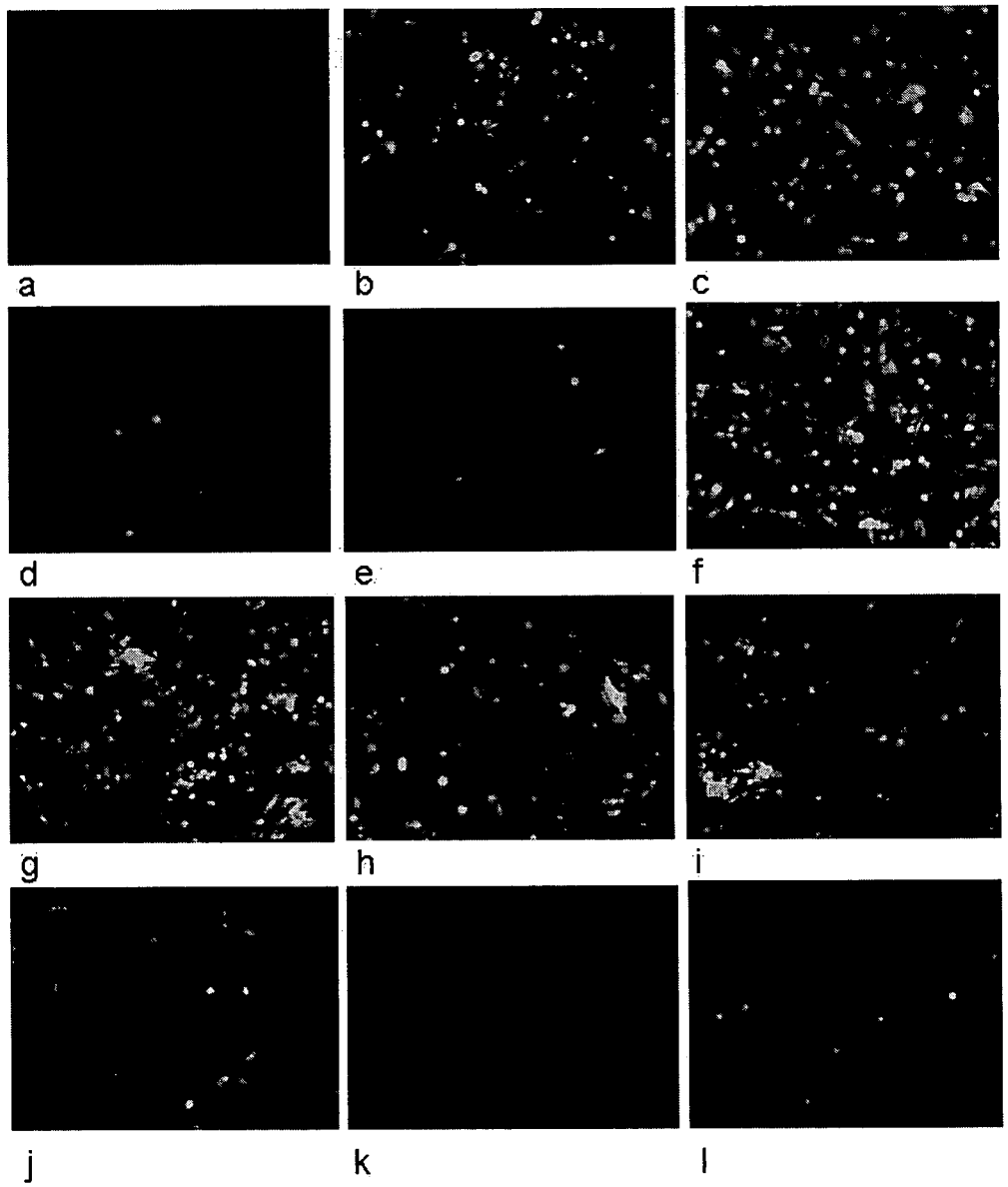

FIG. 8 shows the results of fluorescence microscopy experiments, demonstrating levels of CHO (j) or CHO/DAF (a-i, k,l) cell infection by HSV1716gfp propagated on Vero (a) or BHK cells (b, h, i) or by Vero cell propagated HSV1716 variants expressing B/274gD (c-g, j), 5/260gD (k) or 5/274gD (l). CHO/DAF cells were preincubated in MabB (d), recombinant MabB (e, i), Mab5 (f, h) or MabT (g).

Figure 9:
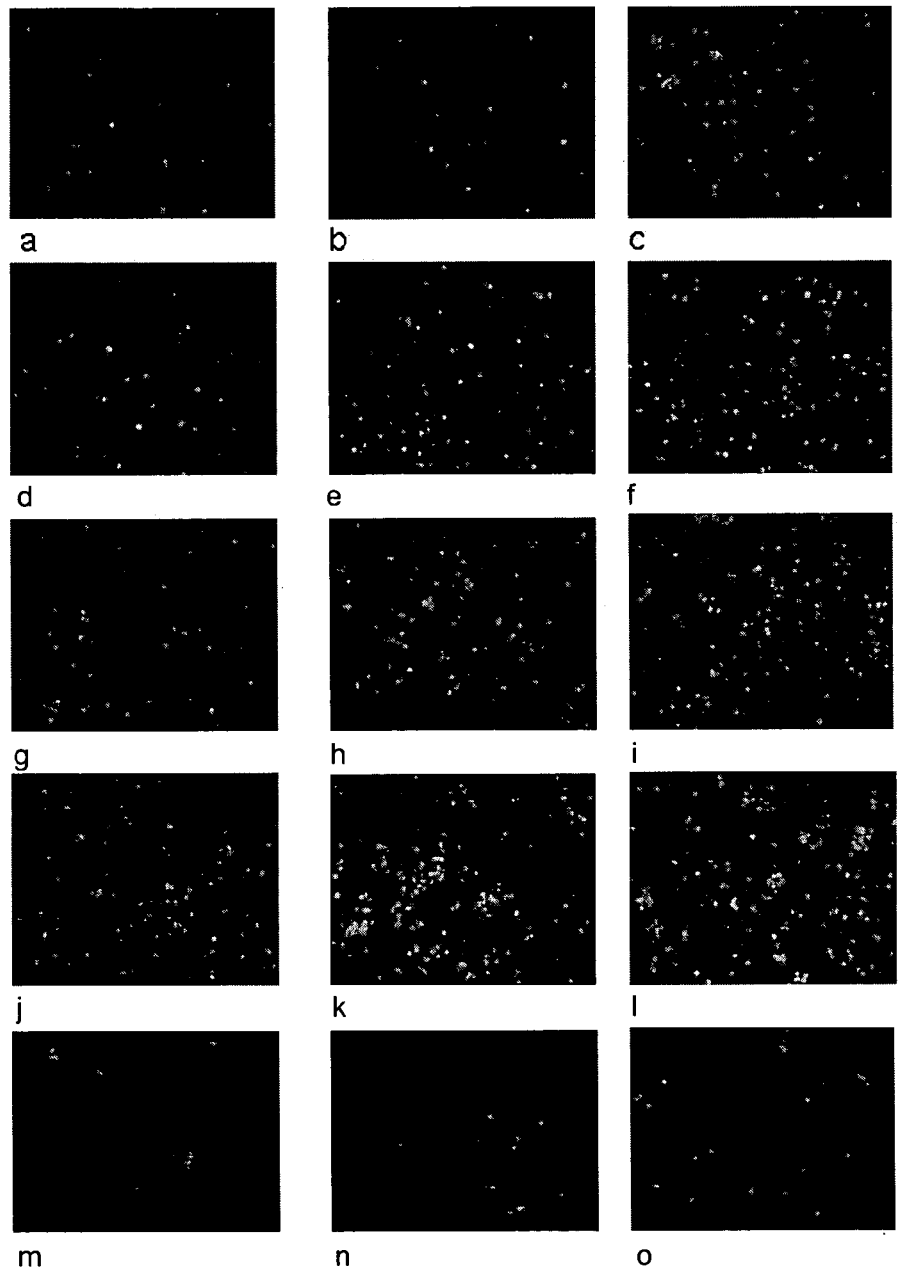

FIG. 9 shows the results of fluorescence microscopy experiments, demonstrating levels of SupT (a, d, g, j, m), THP-1 (b, e, h, k, n) or TolB (c, f, i, l, o) cell infection by HSV1716gfp propagated on Vero (a-c) or BHK (d-f) or Vero propagated HSV1716 variants expressing T/260gD (g-i), T/274gD (j-l) or 5/260gD (m-o).

Figure 10:
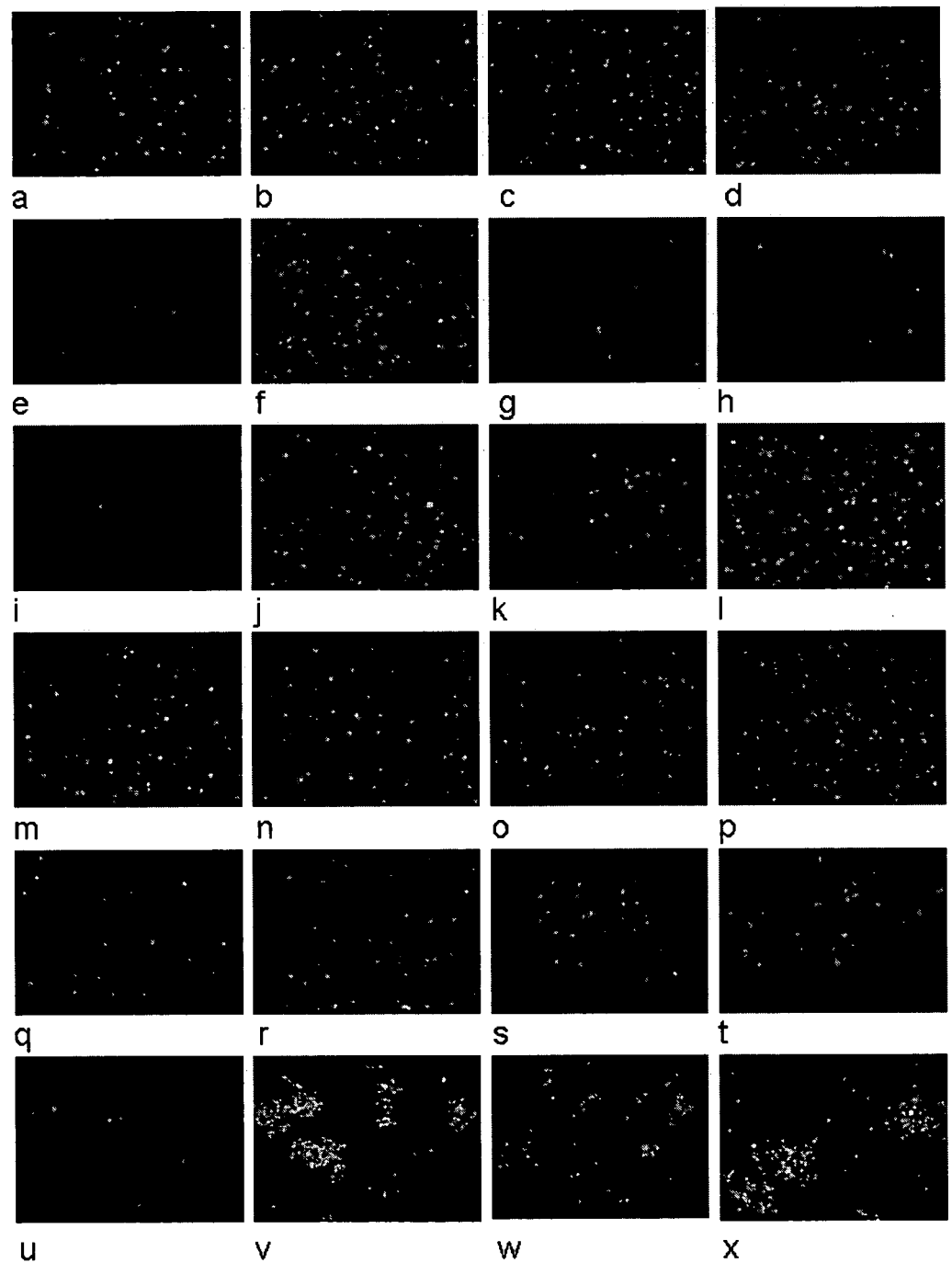

FIG. 10 shows the results of fluorescence microscopy experiments, demonstrating levels of SupT (a-f), THP-1 (g-l) or TolB (m-x) cell infection by Vero propagated HSV1716 variants expressing 5/260gD (a-c, g-o, m-o), T/260gD (d-f, j-l, p-r), 5/274gD (s-u) or T/274gD (v-x). Cells were preincubated in Mab5 (a, d, g, j, m, p, s, v), MabT (b, e, h, k, n, q, t, w) or MabB (c, f, i, l, o, r, u, x).

Figure 11:
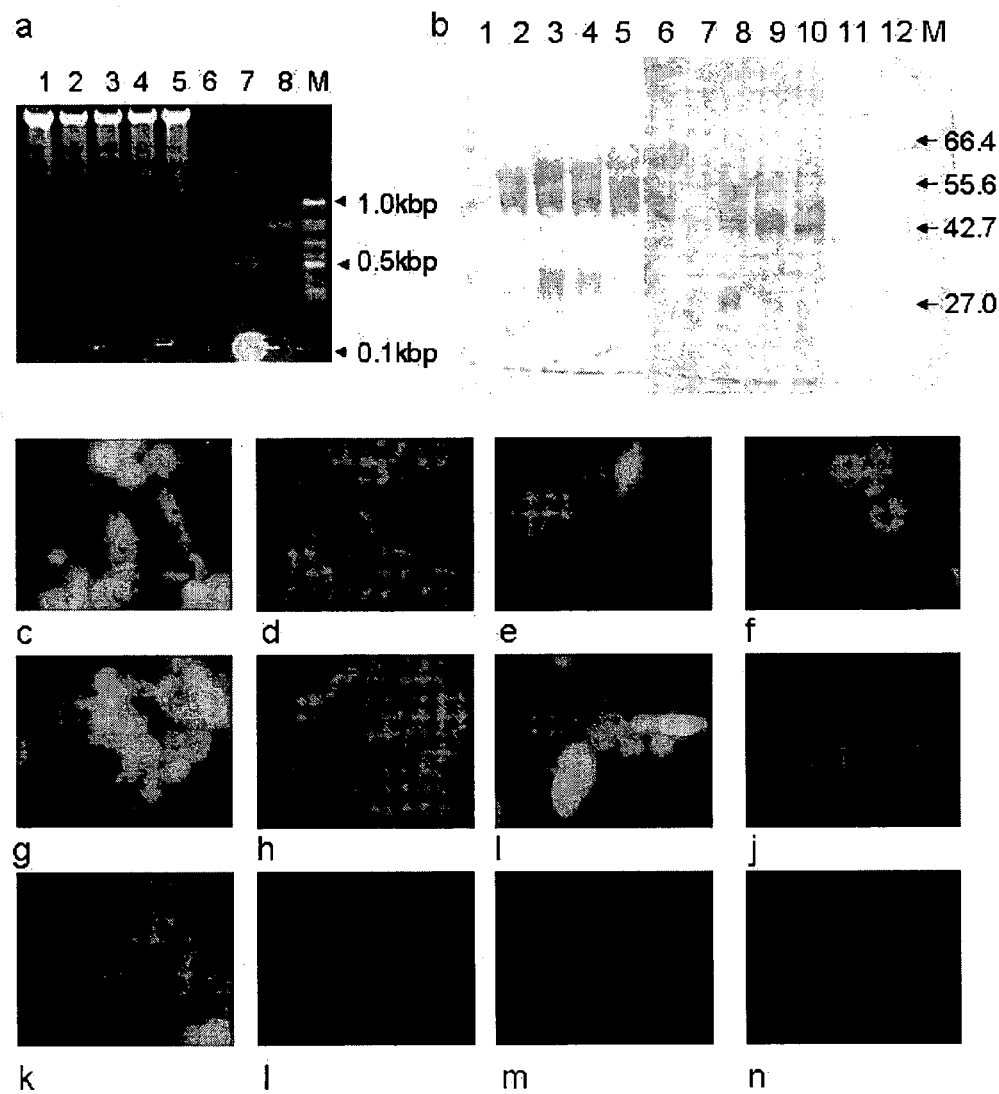

FIG. 11(a) shows RL1 PCR using DNA extracted from BHK cells infected with HSV1716 variants expressing 5/274gD (lane 1), 5/274gDopp (lane 2), T/274gD (lane 3), 8/274gD (lane 4), B/274gD (lane 5), HSV1716 (lane 7) and HSV-1 strain 17+ (lane 8). DNA extracted from uninfected BHK cells is shown in lane 6 and lane M is the 2-log DNA ladder. FIG. 11(b) shows Western blotting using anti-myc-tag monoclonal antibody to probe infected whole cell extracts (lanes 1-5, 11, 12) or purified virions (lanes 6-10) from HSV1716 variants expressing 5/274gDopp (lanes 1 and 7), 5/274gD (lanes 2 and 6), B/274gD (lanes 3 and 8), T/274gD (lanes 4 and 9) and 8/274gD (lanes 5 and 10). Mock- and HSV1716 infected cell extracts are shown in lanes 11 and 12 respectively and lane M is the molecular size markers. Immunofluorescence/fluorescence microscopy of BHK cells infected with HSV1716 variants expressing 5/274gD (c, d), B/274gD (e, f), T/274gD (g, h), 8/274gD (i, j) or 5/274gDopp (k, l). Mock infected BHK cells are shown in m and n. Staining with the anti-myc monoclonal antibody is shown in c, e, g, i, k and m and gfp is shown in d, f, h, j, l and n.

Figure 12:
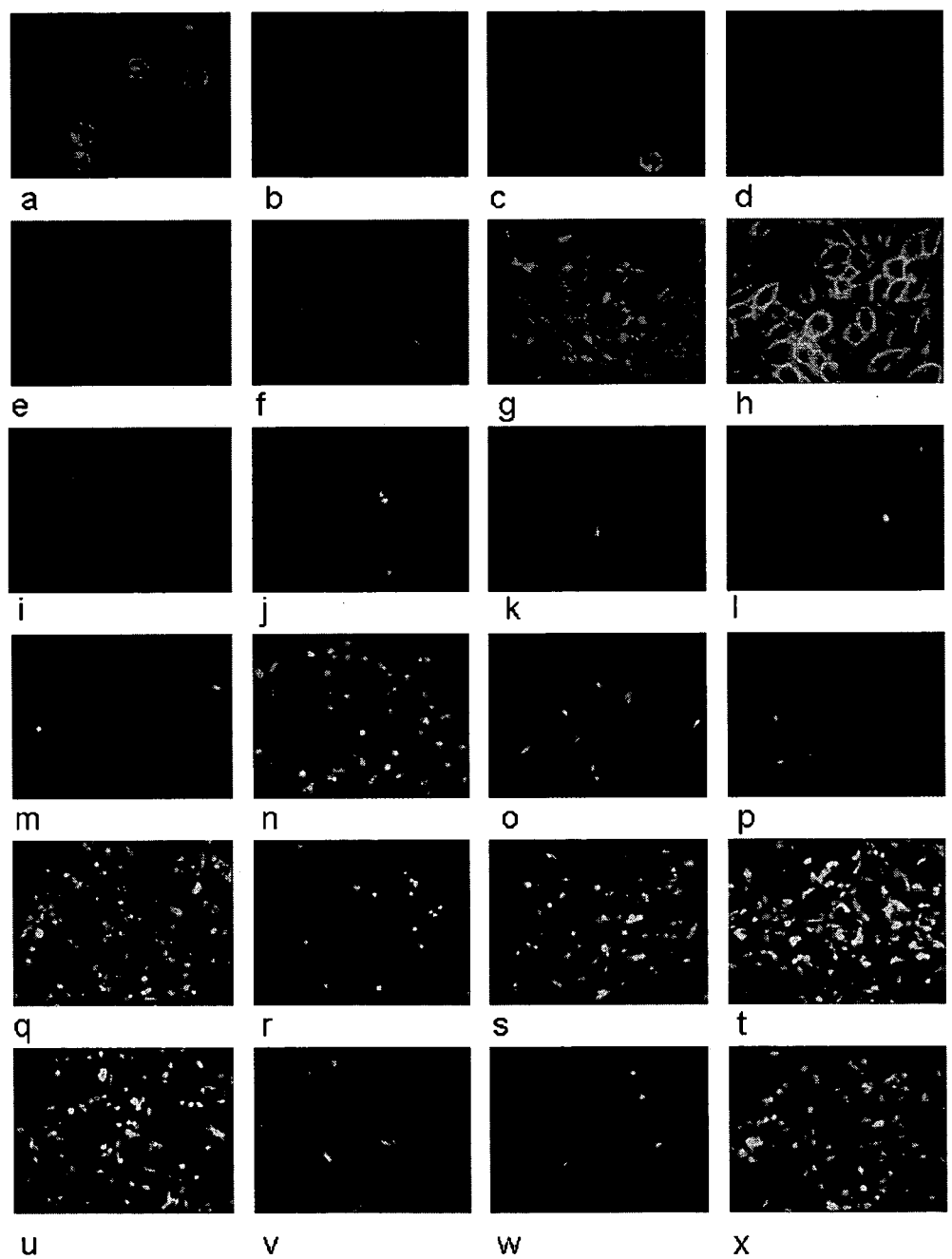

FIG. 12 shows the results of immunofluorescence experiments with MabT (a-c) or Mab5 (d-f), demonstrating expression of CD38 but not CD20 by THP-1 (a, d) SupT cells (b, e) and CD38 and weak CD20 expression by TolB cells (c, f). The immunofluorescence with MabB (g, i) and a recombinant minibody version of MabB (h) demonstrates expression of DAF by CHO/DAF (g, h) but not by normal CHO (i) cells. The fluorescence microscopy also demonstrates levels of CHO (j-n) or CHO/DAF (o-x) cell infection by HSV1716gfp propagated on BHK cells (n, s, x) or by Vero cell propagated HSV1716 variants expressing 5/274gD (j, o), T/274gD (k, p), B/274gD (l, q, t-w) or 8/274gD (m, r). CHO/DAF cells were preincubated in MabB (v, x), recombinant MabB (w), Mab5 (t) or MabT (u).

Figure 13:
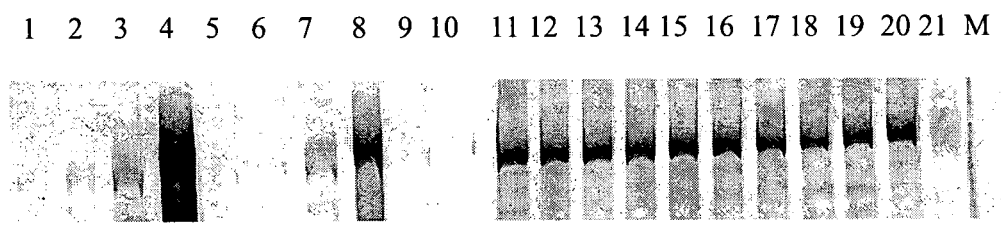

FIG. 13 shows a Western blot using an anti-HSV-1 R1 antiserum to probe whole CHO/DAF (lanes 1-10) or Vero (lanes 11-21) cell extracts after infection with either 1 (lanes 1, 3, 5, 7, 9, 11, 13, 15, 17, 19) or 5 (lanes 2, 4, 6, 8, 10, 12, 14, 16, 18, 20) pfu/cell of HSV1716 variants expressing 8/274gD (lanes 1, 2, 11, 12), B/274gD (lanes 3, 4, 13, 14), T/274gD (lanes 5, 6, 15, 16) or BHK- (lanes 7, 8, 17, 18) or Vero- (lanes 9, 10, 19, 20) propagated HSV1716. Mock infected Vero cell extract is shown in lane 21 and lane M indicates the molecular size markers.

Figure 14:
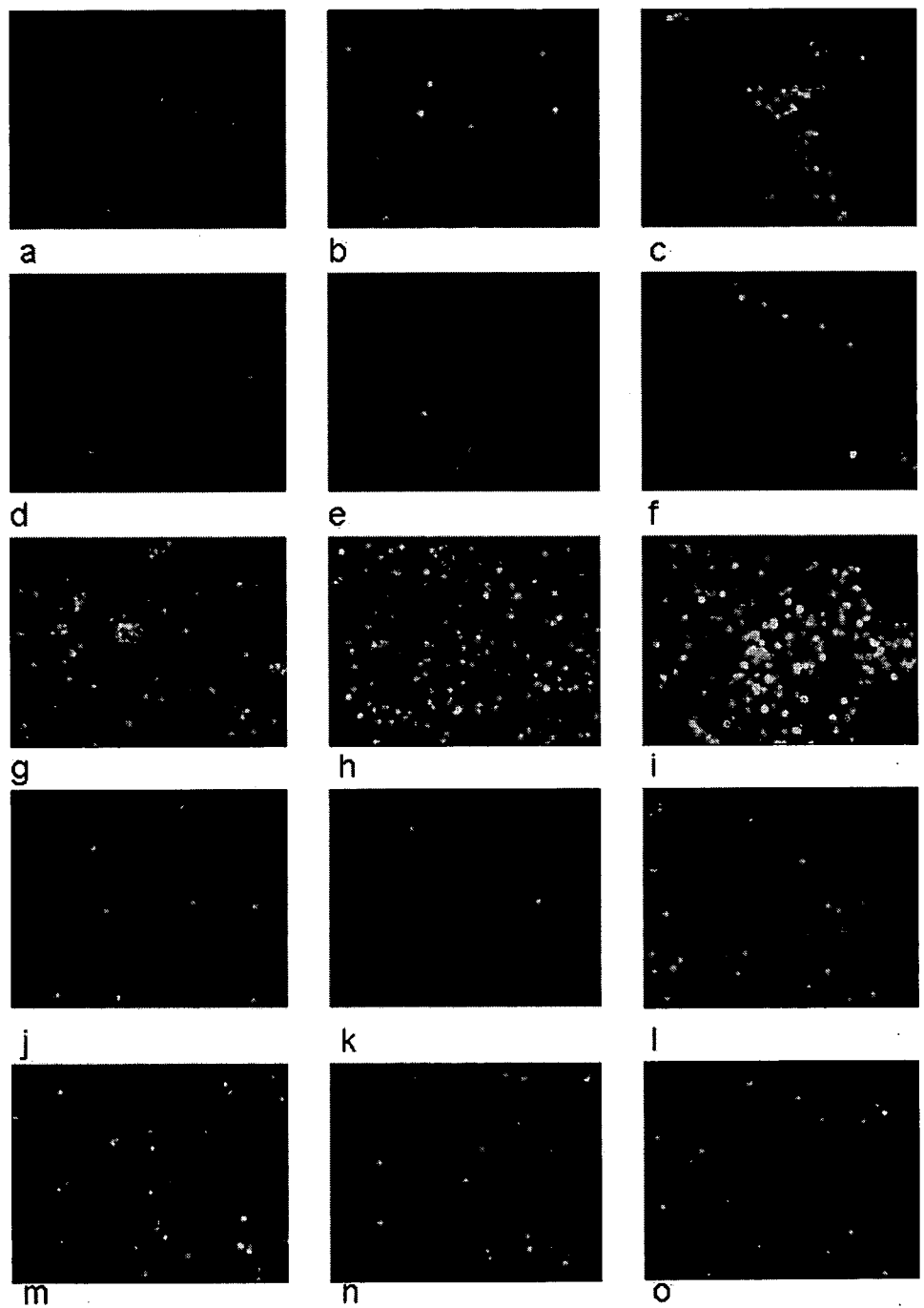

FIG. 14 shows the results of fluorescence microscopy experiments, demonstrating levels of SupT (a, d, g, j, m), THP-1 (b, e, h, k, n) or TolB (c, f, i, l, o) cell infection by Vero cell propagated HSV1716 variants expressing 5/274gD (a-c), 5/274gDopp (d-f), T/274gD (g-i) 8/274gD (j-l) or B/274gD (m-o).

Figure 15:
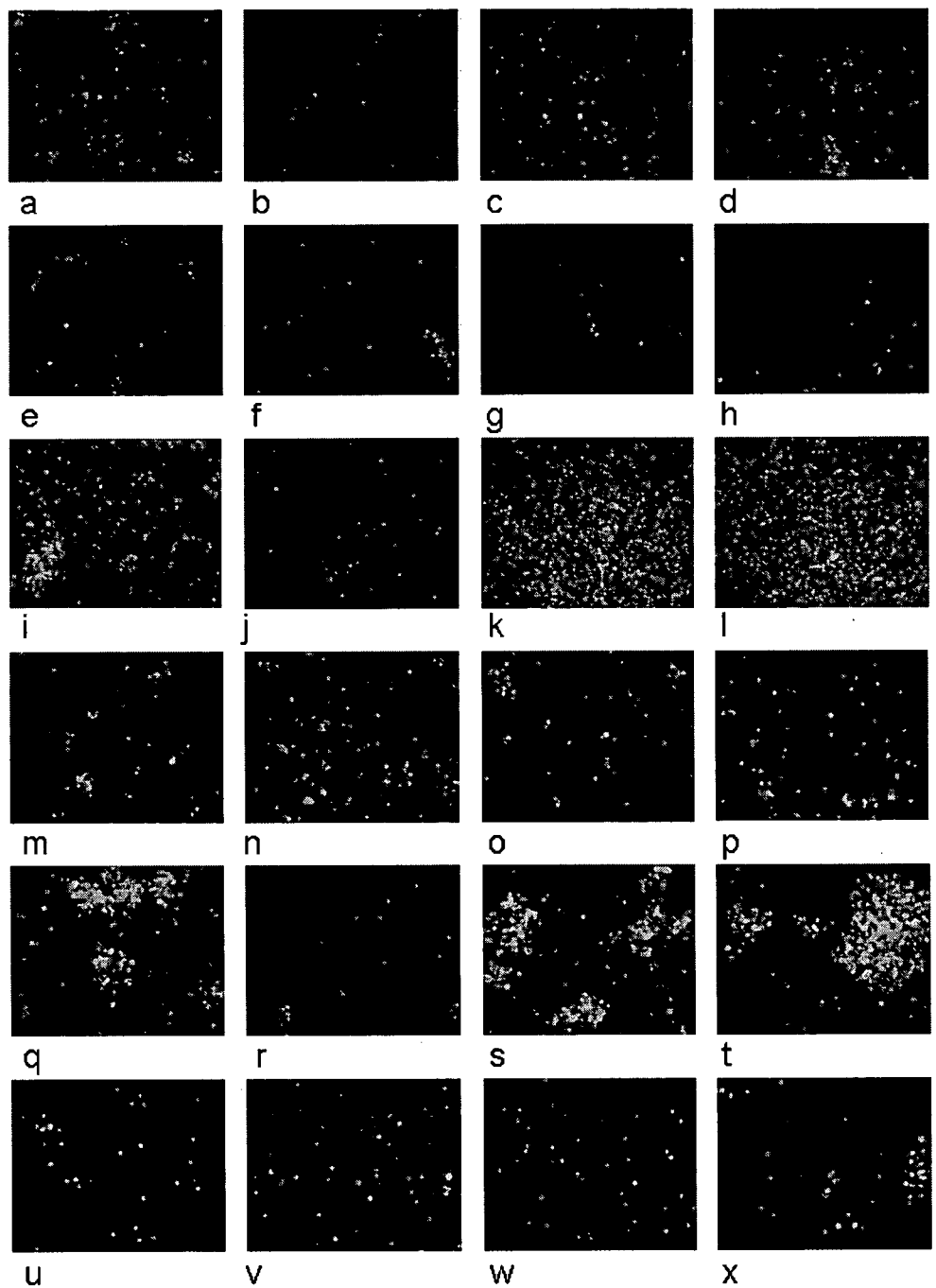

FIG. 15 shows the results of fluorescence microscopy experiments, demonstrating levels of SupT (a-h), THP-1 (i-p) or TolB (q-x) cell infection by Vero propagated HSV1716 variants expressing T/274gD (a-d, i-l, q-t), 8/274gD (e-h), B/274gD (m-p) or 5/274gD (u-x). Cells were preincubated in Mab5 (a, e, i, q), MabT (b, f, j, r), Mab8 (c, g, k, s) or MabB (d, h, l, t).

Figure 16:
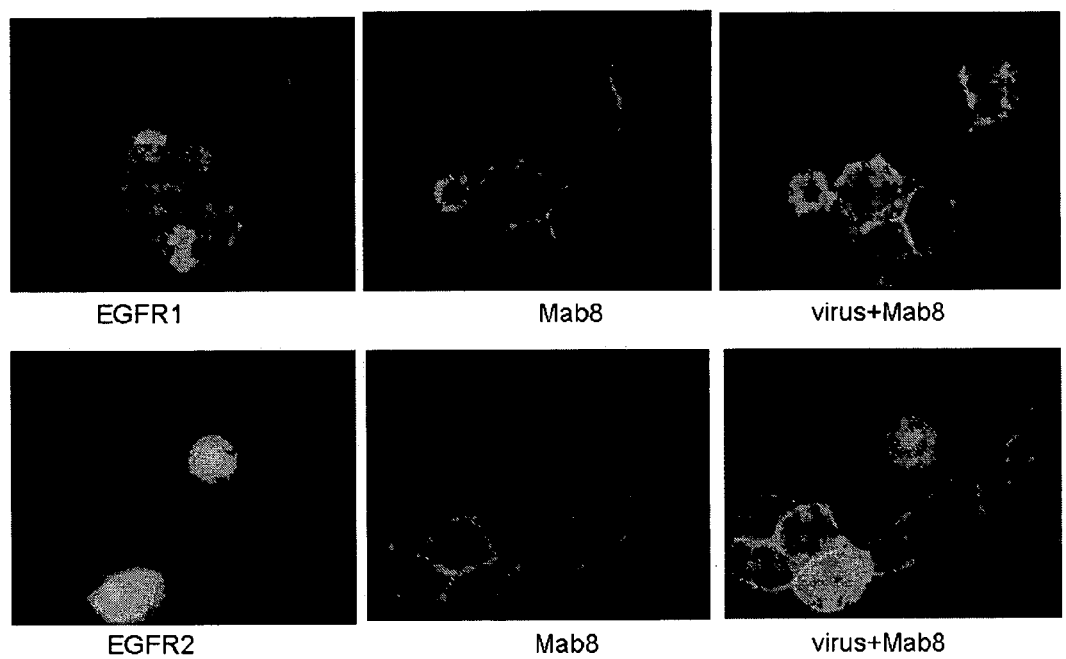

FIG. 16 shows the results of fluorescence microscopy experiments, demonstrating presence of EGFR and infection by HSV1716EGFR1 and EGFR2 (two independently isolated variants of HSV1716 expressing 8/274gD) of A431 cells. Human squamous cell carcinoma (SCC) cells (A431) react with anti-EGFR Mab and are infected with viruses displaying anti-EGFR scFv.

Figure 17A:
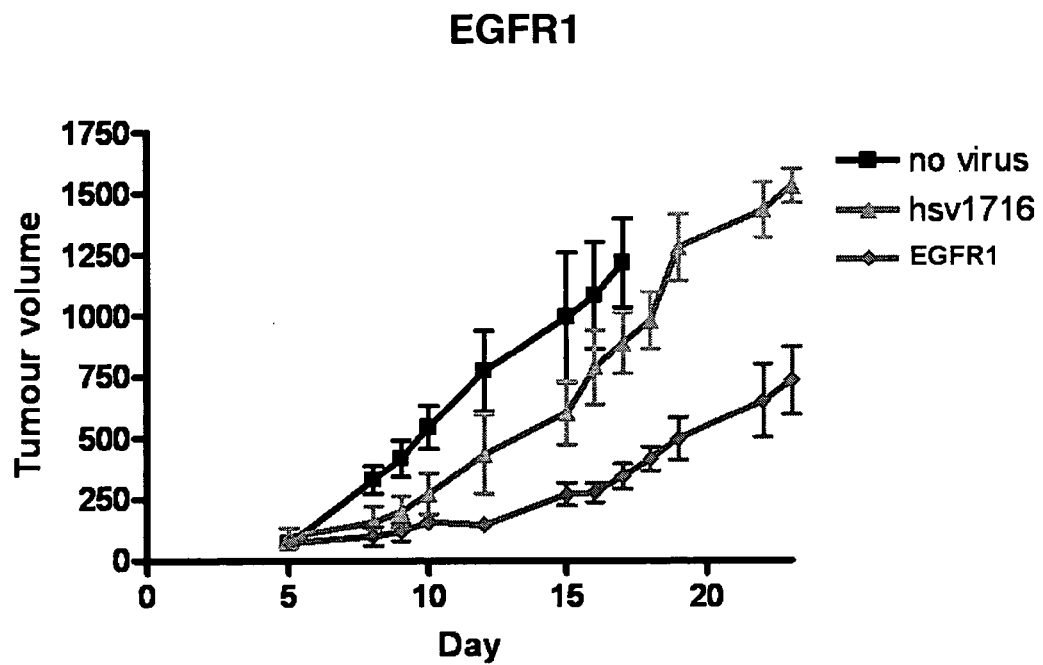
Figure 17B:
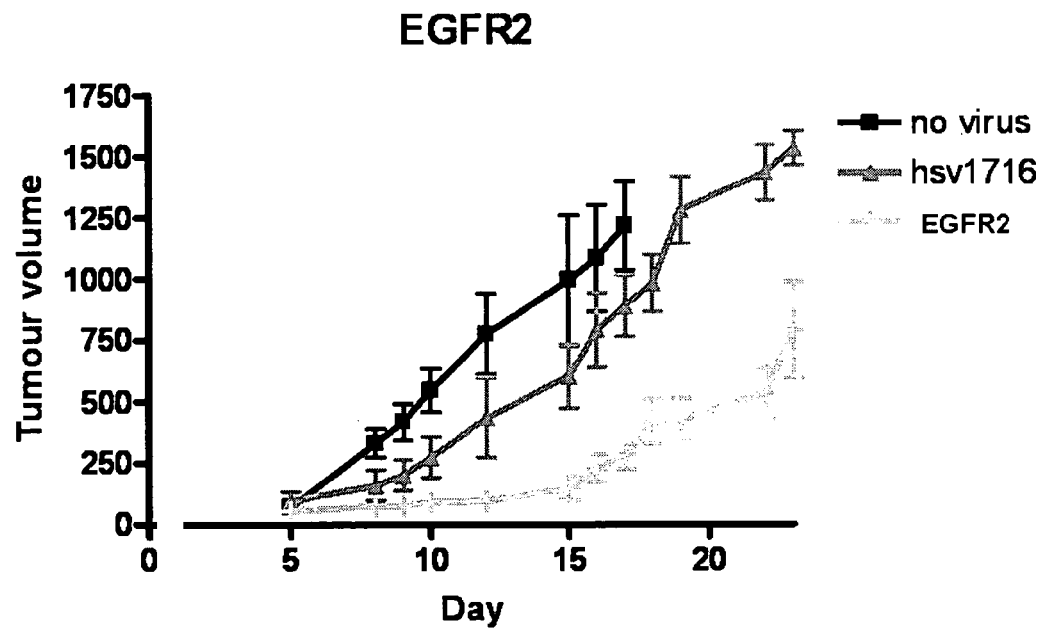

FIG. 17 shows the average tumour volumes of nude mice bearing subcutaneous A431 tumours after intravenous injection of PBS (no virus), HSV1716, HSV1716EGFR1 (a) or HSV1716EGFR2 (b). Intravenously injected EGFR-targeted HSV1716 viruses reduced average tumour volumes of subcutaneous SCC (A431) tumours compared to untargeted HSV1716.

Figure 18:
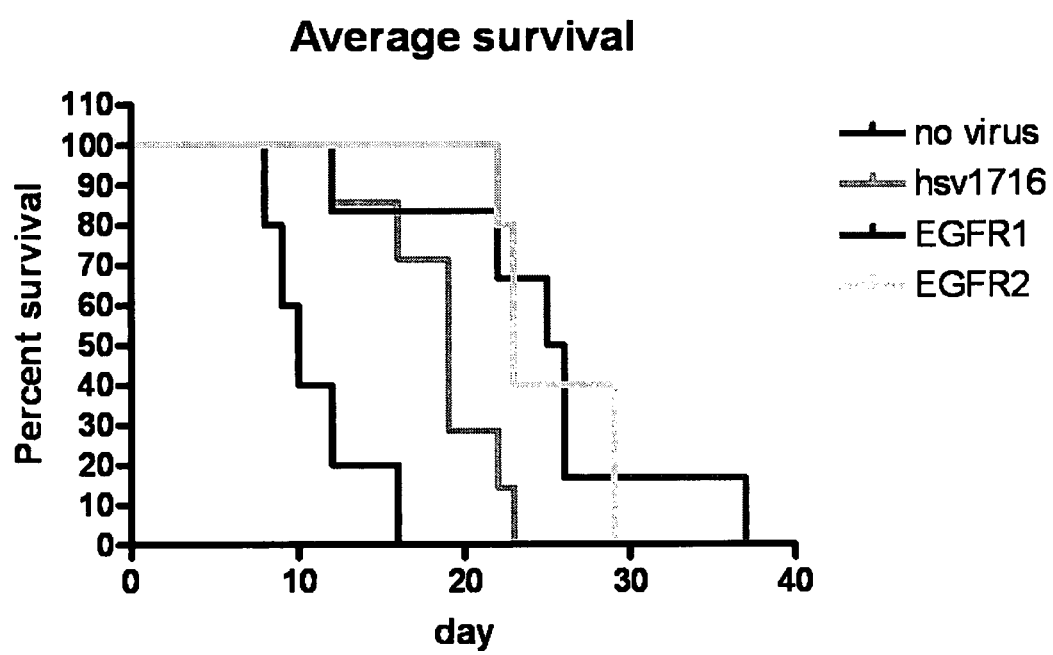

FIG. 18 shows survival data from nude mice bearing subcutaneous A431 tumours after intravenous injection of PBS (no virus), HSV1716, HSV1716EGFR1 or HSV1716EGFR2. Intravenously injected EGFR-targeted HSV1716 viruses prolonged survival of mice with subcutaneous SCC (A431) tumours compared to untargeted HSV1716.

Figure 19:
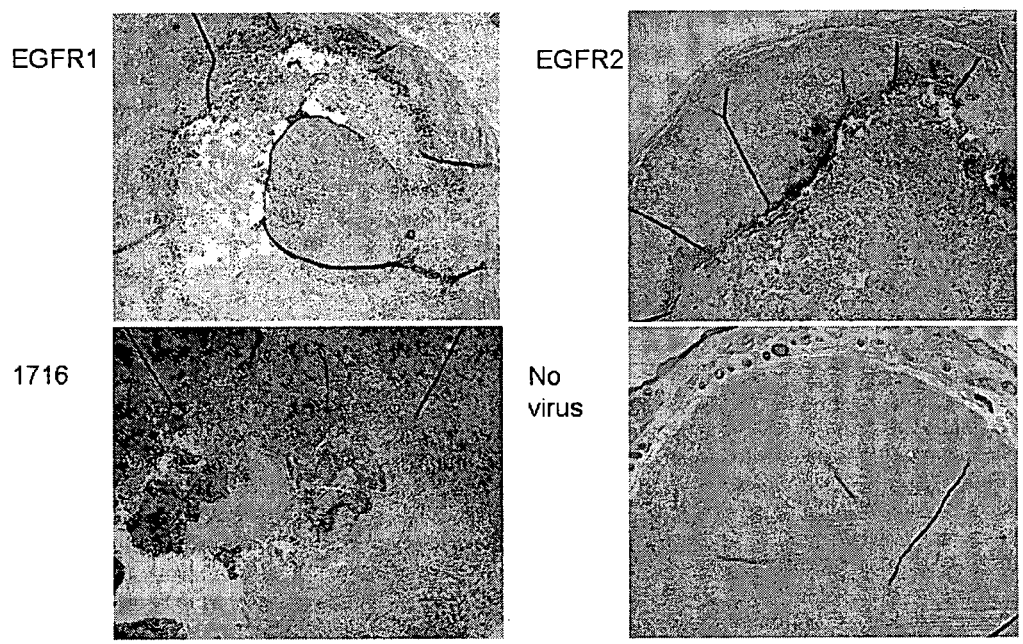

FIG. 19 shows the results of immunohistochemistry experiments using an anti-HSV-1 antiserum of tumours from nude mice bearing subcutaneous A431 tumours after intravenous injection of PBS (no virus), HSV1716, HSV1716EGFR1 or HSV1716EGFR2. Intravenously injected EGFR-targeted HSV1716 viruses show improved tumour localisation to subcutaneous SCC (A431) tumours compared to untargeted HSV1716.

Figure 20A:
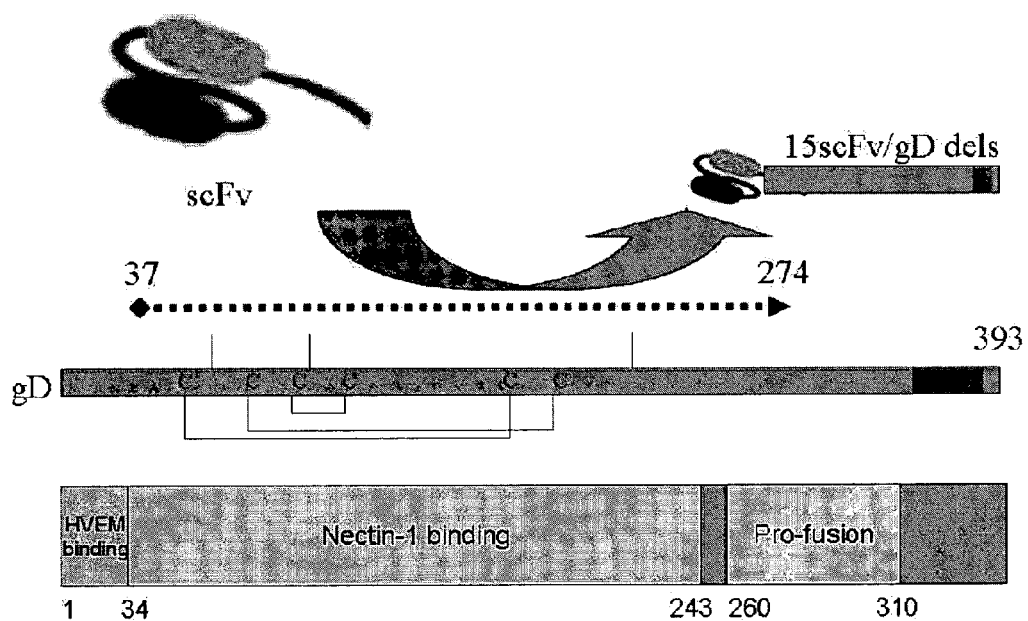
Figure 20B:
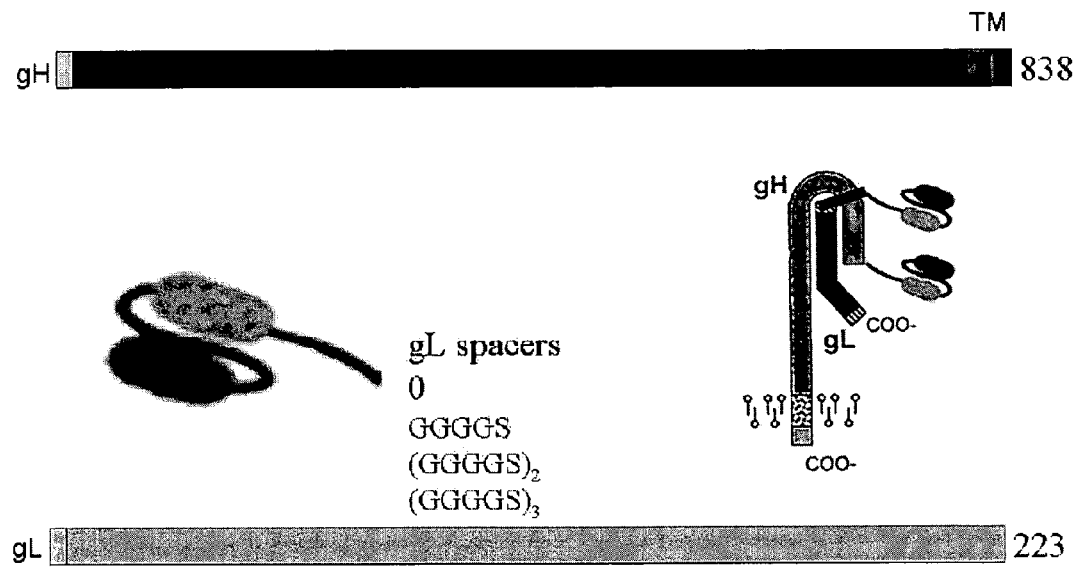

FIG. 20 shows strategies for production of scFv-gD and scFv-gH/gL fusion proteins. (a)(i) shows a schematic diagram showing the construction of the gD truncates. The scFv were genetically fused to 15 sequentially deleted N-terminal truncations of gD generated by PCR from within the region spanning residues 37-274. (ii) shows a linear representation of gD showing the location of carbohydrate moieties (above), disulphide bridges (below) and the transmembrane region (in darker shading), all 15 N-terminal deletions were created between amino acids 37-274 as indicated. (iii) shows a linear representation of gD showing important functional regions of the extracellular domains. (b) shows linear representations of gH and gL (not to scale) and a cartoon depicting the gH/gL heterodimer formed by scFv/gH and scFv/gL fusion proteins.

FIG. 21 shows the nucleic acid sequences and the amino acid sequences of the glycoproteins used in the experiments reported herein. (a) shows gD (SEQ ID NO: 1), (b) shows gH (SEQ ID NO: 2), (c) shows gL (SEQ ID NO: 3). (d) shows the gD nucleic acid sequence (SEQ ID NO: 4), (e) shows the gH complement nucleic acid sequence, (f) shows the gL nucleic acid sequence. These sequences correspond to those under NCBI database accession number X14112.1 (GI:1944536).

DETAILED DESCRIPTION OF THE INVENTION

Specific details of the best mode contemplated by the inventors for carrying out the invention are set forth below, by way of example. It will be apparent to one skilled in the art that the present invention may be practiced without limitation to these specific details.

Results

Figure 1:
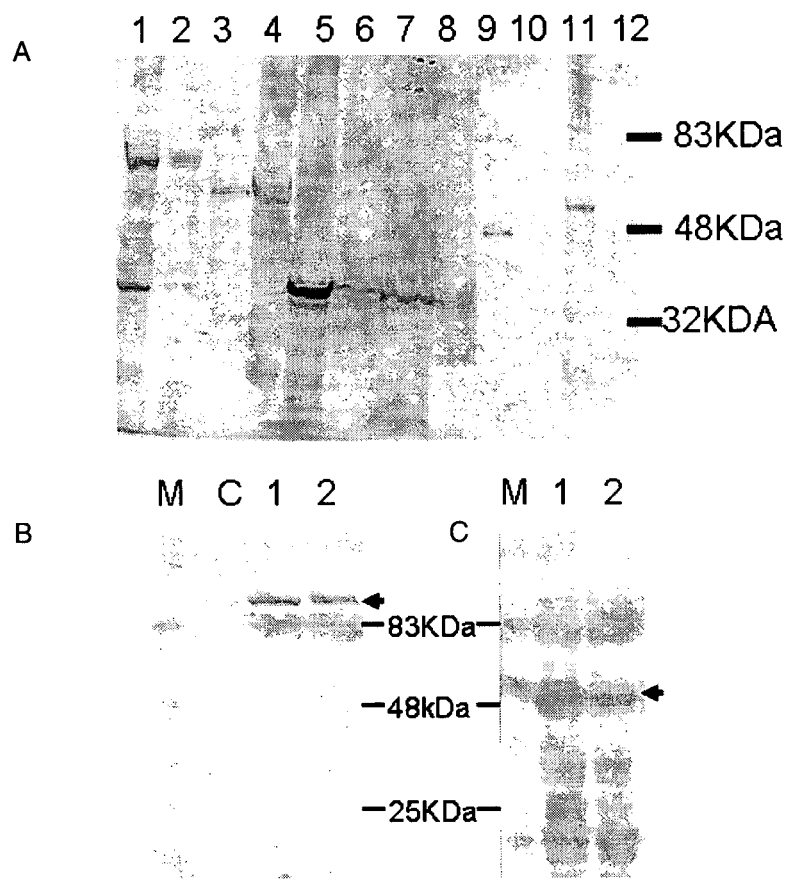
FIG. 1A shows a Western blot probed with anti-myc tag monoclonal antibody demonstrating expression of R24/gD fusion proteins in Vero cells (lanes 1, 4, 5, 7, 9, 11) and their presence in viruses derived from infection of the Vero cell line with HSV1716gfp (lanes 2, 3, 6, 8, 10, 12). Lanes 1 and 2—R24/37gD, lanes 3 and 4—R24/78gD, lanes 5 and 6—R24/260gD, lanes 7 and 8—R24/274gD, lanes 9 and 10—R24/231gD, lanes 11 and 12—R24/164gD and lane M molecular size markers. b) and c).
FIGS. 1B and 1C show Western blot probed with anti-HA tag (B) and anti-myc tag (C) demonstrating expression of R24/gH (B, lane 1) and R24/gL3 (C, lane 1) in the same Vero cell extract and their combined incorporation into a virion preparation from the same cell line infected with HSV1716gfp (B and C, lane 2). Lane C is a control Vero cell extract and lane M is molecular size markers.

To analyse the effects of the scFv/gD or scFv/gH/gL glycoprotein fusion proteins on tropism, infection of non-permissive CHO cells by viruses propagated on stable Vero cell lines expressing the glycoprotein fusion proteins was assessed. Gangliosides are ubiquitous components of cell membranes and GD3 was present on CHO cells as determined by R24 binding (data not shown). All 15 gD deletions were linked to the R24 scFv and stable Vero cell lines expressing these scFv/gD fusion proteins created. Expression of the myc-tagged fusion proteins was demonstrated by immunofluorescence and Western blotting. (FIG. 1, Table 2).

FIG. 1A demonstrates expression of various R24/gD fusion proteins and their subsequent incorporation into virus preparations following infection of the cell line with HSV1716gfp. The results for all R24/gD fusion proteins are presented in Table 2. In FIG. 1A, apart from R24/37gD (lane 1) and R24/260gD (lane 5) which were expressed at high levels, the other constructs, R24/78gD (lane 4), R24/164gD (lane 11), R24/231gD (lane 9) and R24/274gD (lane 7) all showed an intermediate level of expression. Two expressed constructs, R24/164gD (lane 12) and R24/231gD (lane 10) were not incorporated into virus whereas R24/37gD (lane 2), R24/78gD (lane 3), R24/260gD (lane 6) and R24/274gD (lane 8) were detected at intermediate levels in virus preparations. R24/58gD and R24/105gD were not expressed and R24/92gD, R24/128gD, R24/139gD, R24/179gD, R24/191gD, R24/207gD and R24/239gD showed intermediate levels of expression. Of these, R24/92gD and R24/128gD demonstrated intermediate levels of incorporation into virus with the remainder incorporated at low levels (Table 2).

Combined transfection and dual selection with zeocin and hygromycin of Vero cells with R24/gH and each of the R24/gL, R24/gL1, R24/gL2 or R24/gL3 fusion protein constructs resulted in stable cell lines expressing both gH and gL fusion proteins. Following infection with HSV1716gfp, the R24/gH and R24/gL proteins were detected in purified virus preparations. The Western blots shown in FIG. 1B (anti-HA tag) and C (anti-myc tag) demonstrate expression of R24/gH (FIG. 1B, lane 1) and R24/gL3 (1C, lane 1) in the same Vero cell extract and their combined incorporation into a virion preparation after infection with HSV1716gfp (FIGS. 1B and C, lane 2). Similar results were obtained with the R24/gH/gL, R24gH/gL1 and R24/gH/gL2 cell lines (data not shown).

Figure 2:
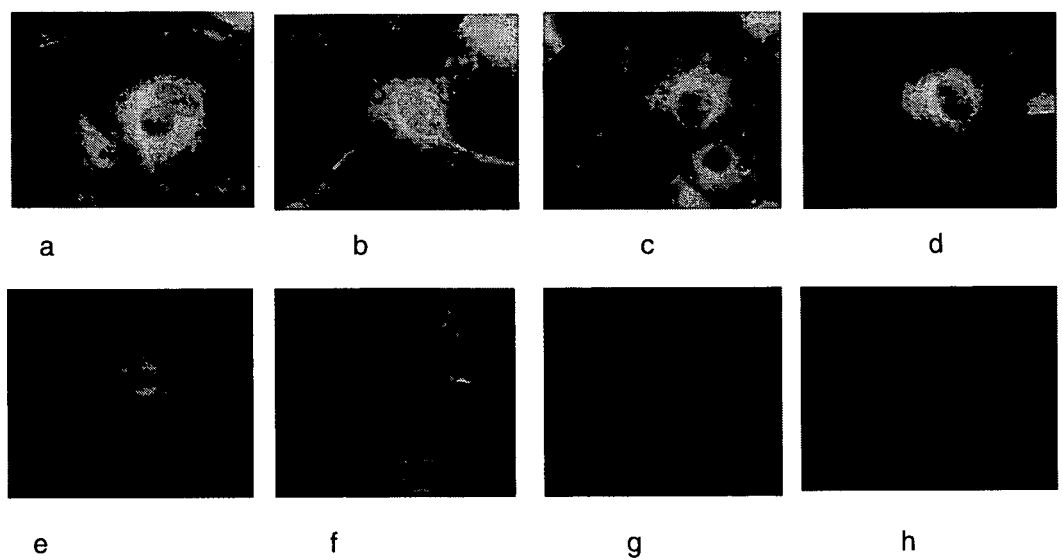
FIG. 2 shows the results of immunofluorescence experiments with anti-myc tag (a-d, f, g) or anti-HA tag (e and h), demonstrating cellular localization of R24/gD and R24/gH/gL fusion proteins in the Vero cell lines expressing R24/37gD (a), R24/128gD (b), R24/191gD (c), R24/274gD (d), R24/gH (e) and R24/gL (f) Anti-myc tag (g) and anti-HA tag (h) monoclonal antibodies failed to stain normal Vero cells.

The cellular localization of the R24/gD and R24/gH/gL fusion proteins was investigated in the Vero cell lines by immunofluorescence using either the anti-myc tag (gD, gL) or anti-HA tag (gH) monoclonal antibodies. All of the expressed R24/gD fusion proteins demonstrated similar perinuclear localizations (Table 2) as shown for R24/37gD (FIG. 2a), R24/128gD (FIG. 2b), R24/191gD (FIG. 2c) or R24/274gD (FIG. 2d). Similarly, FIGS. 2e and f respectively show the same perinuclear localization for R24/gH and R24/gL in the same Vero cell line and this localization was identical for the other R24/gH/gL1-3 expressing cell lines (data not shown). Anti-myc tag and anti-HA tag monoclonal antibodies failed to stain normal Vero cells (FIGS. 2g and h respectively) and no fluorescence was observed in cells that failed to express fusion protein constructs (data not shown). Thus, the cellular localization of the R24/gD and R24/gH/gL fusion proteins was very similar and consistent with an accumulation in the nuclear membrane/endoplasmic reticulum/Golgi apparatus.

Figure 3:
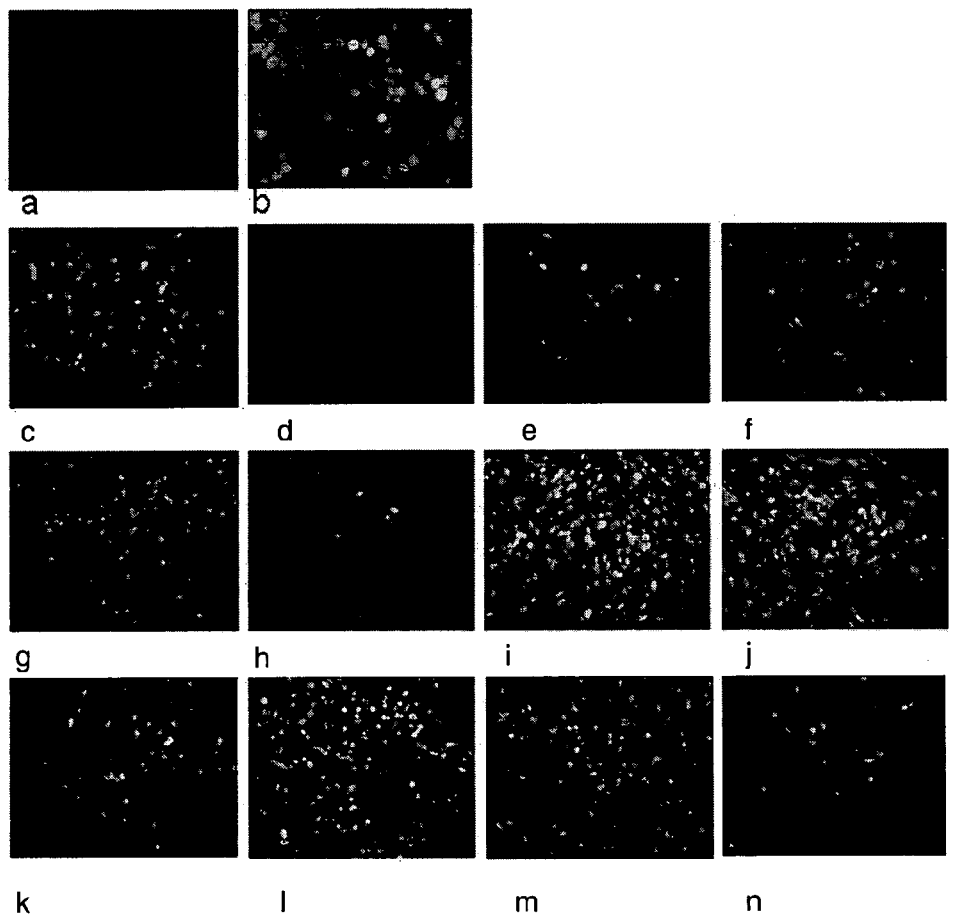
FIG. 3 shows fluorescent micrographs of CHO cells infected with HSV1716gfp propagated on Vero (a) or BHK (b) cells or stable Vero cell lines expressing R24 linked to 37gD (c), 139gD (d), 78gD (e), 92gD (f), 128gD (g) 179gD (h), 260gD (i), 274gD (j), gH/gL (k), gH/gL1 (l), gH/gL2 (m) or gH/gL3 (n).
Figure 4:
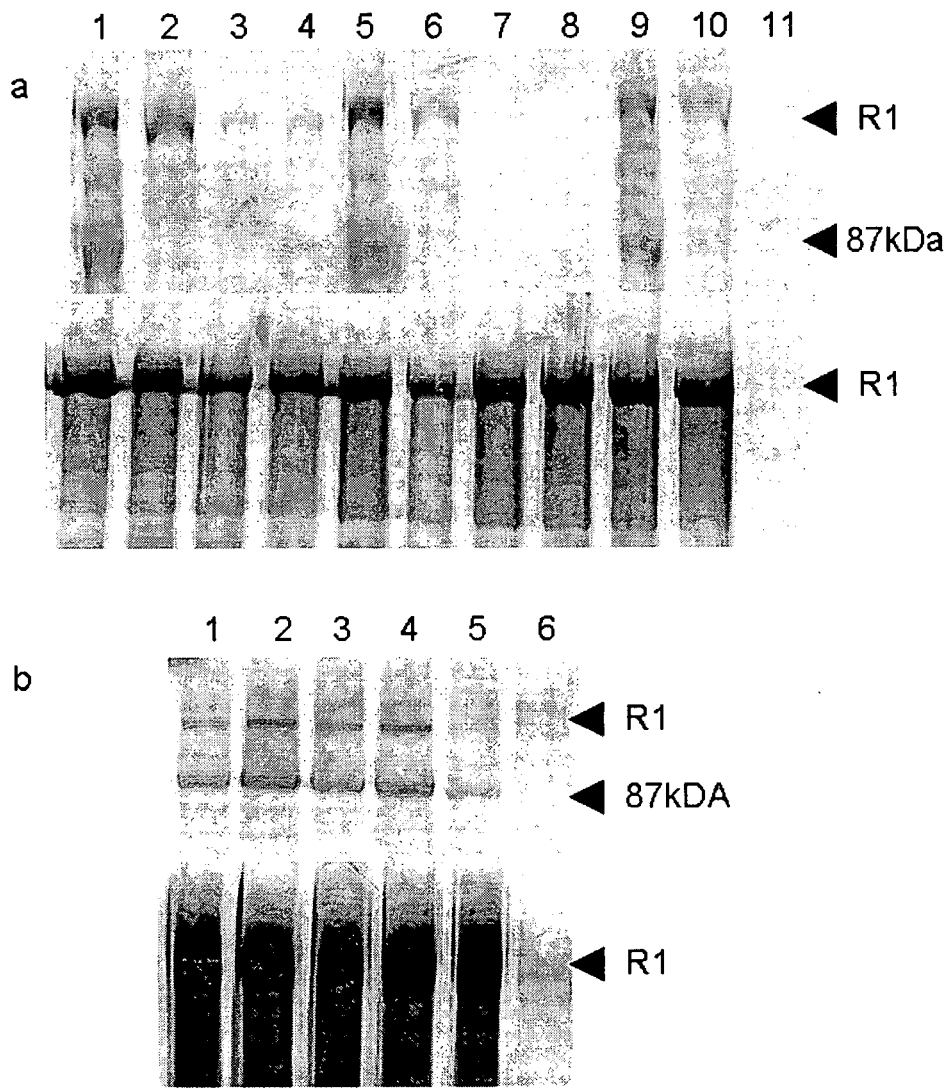
FIG. 4 shows Western blots probed with antiserum 106 against HSV-1 R1 of whole cell extracts from CHO (upper panels a and b) or Vero (lower panels a and b) cells infected with HSV1716gfp viruses obtained from propagation on various Vero cell lines expressing R24/gD or R24gH/gL glycoprotein fusion protein. (a) shows HSV1716gfp propagated on BHK cells (lane 1) or viruses propagated on Vero cells expressing R24/37gD (lane 2), R24/78gD (lane 3), R24/179gD (lane 4), R24/128gD (lane 5), R24/92gD (lane 6), R24/191gD (lane 7), R24/207gD (lane 8), R24/260gD (lane 9), R24/274gD (lane 10) or mock infected cell extracts (lane 11). (b) shows HSV1716gfp propagated on Vero cells expressing R24/gH in tandem with R24/gL (lane 1), R24/gL1 (lane 2), R24/gL2 (lane 3) or R24/gL3 (lane 4), normal Vero cells (lane 5) or mock infected (lane 6).
Figure 5:
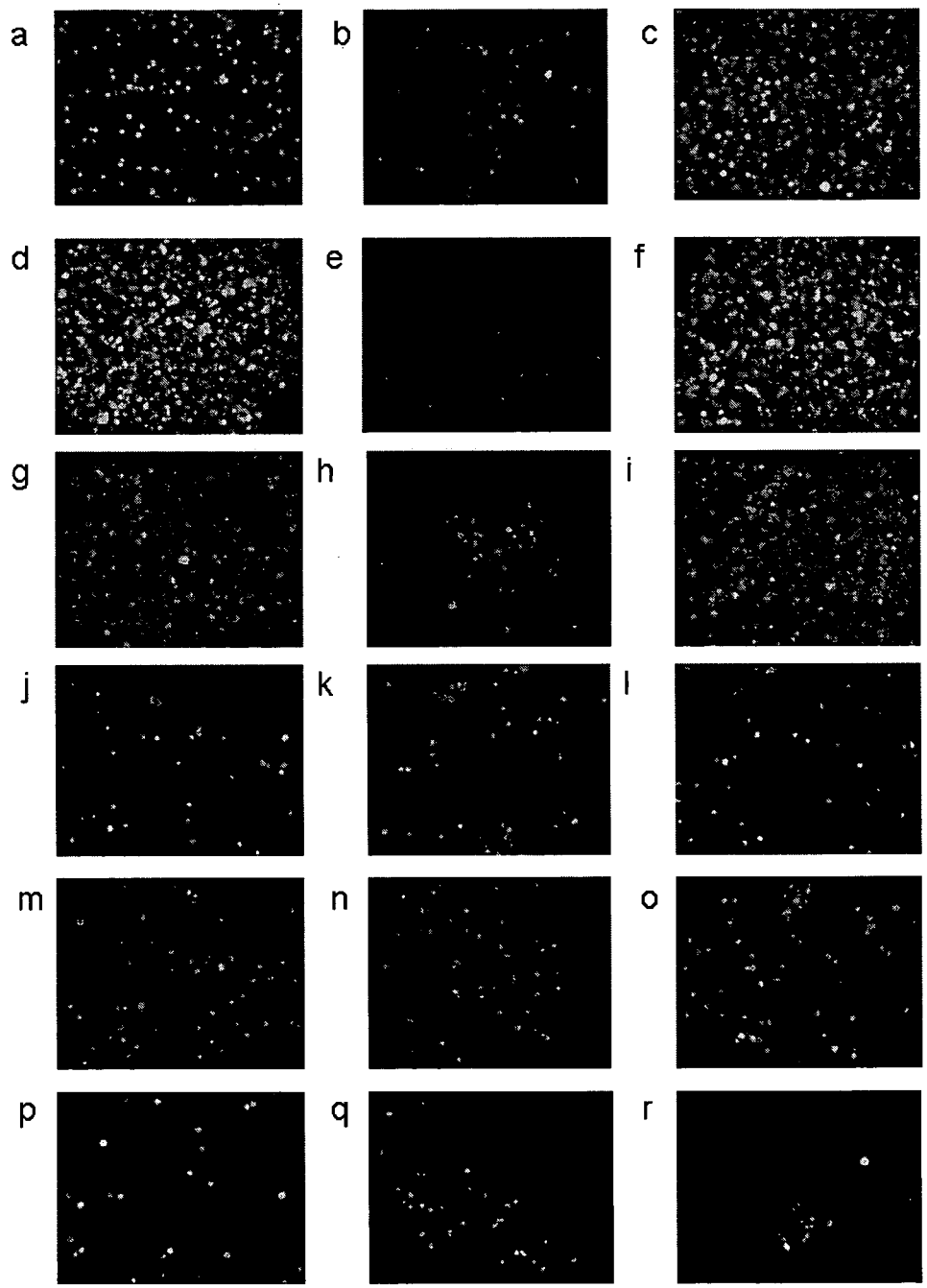
FIG. 5 shows the results of fluorescence microscopy experiments, showing levels of THP-1 cell infectivity by viruses derived from Vero cell lines expressing T/37gD (a, b, c), T/260gD (d, e, f), T/gH/gL2 (g, h, i), 5/37gD (j, k, l), 5/260gD (m, n, o) or 5/gH/gL2 (p, q, r). Prior to infection, THP-1 cells were preincubated in control medium (a, d, g, j, m, p), MabT (b, e, h, k, n, q) or Mab5 (c, f, i, l, o, r).
Figure 6:
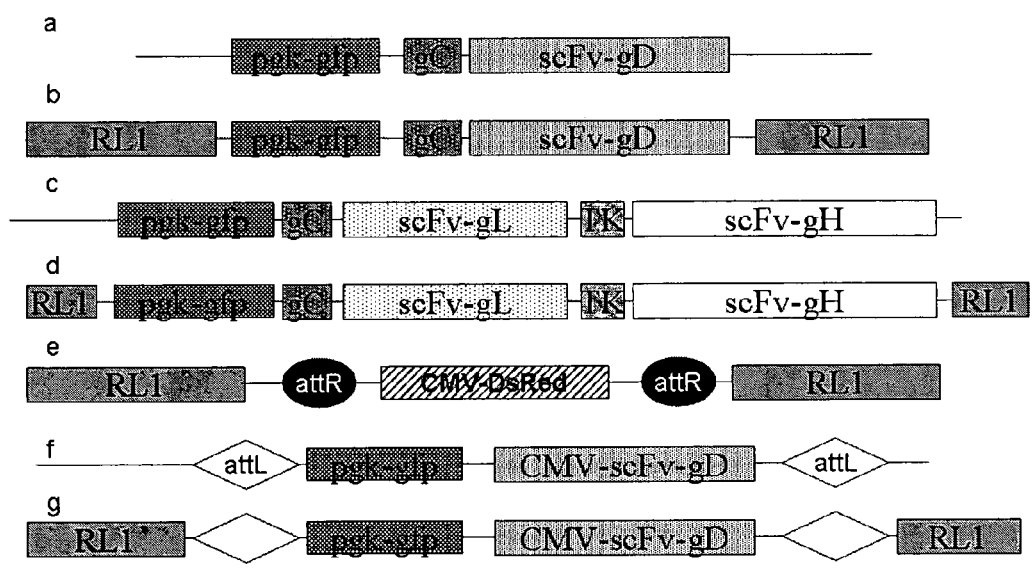
FIG. 6 shows linear representations of key plasmids and genomic structures of viruses at RL1.

CHO cells, normally resistant to HSV1716 infection when the virus is propagated on Vero cells, were infected with 1 pfu/cell HSV1716gfp derived from infection of the R24/gD, R24/gH/gL fusion protein expressing cell lines and the percentages of infected cell determined by fluorescence microscopy (FIG. 3, Table 2). HSV1716gfp propagated on Vero cells failed to infect CHO cells (FIG. 3a) and this contrasts with HSV1716gfp propagated on BHK cells which infects approximately 30% of CHO cells (FIG. 3b).

A number of HSV1716gfp viruses propagated on Vero cell lines expressing R24/gD fusion proteins were able to infect CHO cells at levels similar to or greater than those obtained with HSV1716gfp propagated on BHK cells. Examples are shown in FIG. 3(c-j) and the results summarized in Table 2.

R24/37gD (FIG. 3c), R24/77gD (FIG. 3e), R24/92gD (FIG. 3f), R24/128gD (FIG. 3k), R24/260gD (FIG. 3i) and R24/274gD (FIG. 3j) infected 30%, 10%, 20%, 20%, 60% and 50% respectively of CHO cells compared to only occasionally infected CHO cells (<1%) for the other R24/gD fusion proteins (FIG. 3d, example shown is R24/139gD) apart from R24/178gD (FIG. 3l) which consistently infected between 3-5%. All of the R24/gH/gL heterodimeric fusion proteins were able to infect CHO cells (FIG. 3k-n) with varying efficiencies. R24/gH/gL, with no spacer linking the scFv to the N terminus of gL, infected ~20% (FIG. 3k) compared to 40%, 30%

In addition to the human monocytic cell line THP-1, which we have demonstrated by immunofluorescence to express CD38 but not CD20, we also used two other human leukaemic cell lines, SupT, a T-cell line that expresses CD38 (FIG. 7e) but not CD20 (FIG. 7f) and TolB, a B-cell line that expresses both CD38 (FIG. 7g) and CD20 (FIG. 7h). The weak fluorescence observed with Mab5/TolB suggests that this protein is expressed at lower levels compared to CD38 expression in this and the other lines. We also created a CHO cell line (CHO/DAF) that constitutively expressed human DAF (CD55) as demonstrated by immunofluorescence with MabB (FIG. 7i) and a recombinant minibody version of MabB comprising two scFvs binding sites dimerised via a human IgG1 Fc region (FIG. 7j). Both of these antibodies identified intense membrane staining of CD55 in the modified CHO cells but neither stained normal CHO cells (FIGS. 7k and l). The abilities of the targeted HSV1716 variants to infect these cell lines were analysed by fluorescent microscopy with the results summarized in Table 4. Examples of their infectivities in the presence or absence of various monoclonal antibodies are shown in FIGS. 8-10.

As previously reported (Conner et al 2005), HSV1716 propagated in Vero cells (HSV1716V) was unable to infect CHO/DAF cells compared with HSV1716 propagated in BHK cells (HSV1716B) which was able to infect approximately 20% of CHO/DAF cells (FIGS. 8a and b respectively). Significantly, approximately 50% of CHO/DAF cells were infected by an HSV1716 variant expressing the B/274gD fusion protein (FIG. 8c) and this level of infectivity was reduced to approximately 5% by preincubating the CHO/DAF cells either in MabB (FIG. 8d) or the recombinant minibody form of MabB (FIG. 8e) but was unaffected by preincubation of the cells in either Mab5 (FIG. 8f) or MabT (FIG. 8g). The ability of HSV1716B to infect CHO/DAF cells was unaffected by either Mab5 (FIG. 8h) or recombinant MabB (FIG. 8i). As the HSV1716 variant expressing B/274gD used in these experiments was propagated in Vero cells, it only infected approximately 5% of normal CHO cells (FIG. 8j). The HSV1716 variants expressing 5/260gD (FIG. 8k) and 5/274gD (FIG. 8l) and propagated on Vero cells were also able to infect only 1-5% of CHO/DAF cells.

Three human leukaemic cell lines, all of which display CD38 and one of which also displays CD20, were semi-permissive for HSV1716 infection as shown in FIG. 9. HSV1716V infected approximately 10% of both SupT and THP-1 cells (FIGS. 9a and b) at 1 pfu/cell compared to approximately 20% of SupT or THP-1 cells infected with 1 pfu/cell HSV1716B (FIGS. 9d and e). A higher proportion of TolB cells were infected with approximately 20% of cell infected by HSV1716V (FIG. 9c) compared with 50% infected by HSV1716B (FIG. 9f). Using 1 pfu/cell of the Vero cell propagated HSV1716 variant expressing T/260gD, approximately 30% SupT (FIG. 9g), 50% THP-1 (FIG. 9h) and 50% TolB (FIG. 9i) cells were infected. Similarly, the Vero cell propagated HSV1716 variant expressing T/274gD infected 50% SupT (FIG. 9j), 50% THP-1 (FIG. 9k) and 70% TolB (FIG. 9l) which, when compared to the Vero cell propagated HSV1716 variant expressing 5/260gD that was only able to infect 5% SupT (FIG. 9m), 5% THP-1 (FIG. 9n) or 20% TolB (FIG. 9o), demonstrates that viruses displaying scFvT have enhanced infectivity for these three cell lines via CD38. This was confirmed using the same viruses to infect SupT, THP-1 and TolB cells that were preincubated with Mab5, MabB or MabT.

Infection of SupT cells by a Vero cell propagated HSV1716 variant expressing 5/260gD was unaffected by preincubation of the cells in Mab5 (FIG. 10a), MabT (FIG. 10b) or MabB (FIG. 10c) with approximately 20% of cells infected in each case, which, in this experiment, was similar to HSV1716V infection of SupT cells preincubated with each of these monoclonal antibodies (data not shown). In contrast, a Vero cell propagated HSV1716 variant expressing T/260gD infected 40% or 50% of SupT cells when preincubated in Mab5 (FIG. 10d) or MabB (FIG. 10f) respectively and this higher level of infectivity was reduced to 5% when the SupT cells were preincubated in MabT (FIG. 10e). Similarly, the Vero cell propagated HSV1716 variant expressing T/274gD infected 50% and 40% of SupT cells preincubated with either Mab5 or MabB respectively and this was reduced to 10% by preincubation of the cells in MabT (data not shown). The Vero cell propagated HSV1716 variant expressing 5/274gD infected approximately 10% of SupT cells incubated in Mab5, MabT or MabB (data not shown).

THP-1 infection by a Vero cell propagated HSV1716 variant expressing 5/260gD was unaffected by preincubation of the cells in Mab5 (FIG. 10g), MabT (FIG. 10h) or MabB (FIG. 10i) with approximately 5% of cells infected in each case whereas HSV1716V infection of THP-1 cells preincubated with each of these monoclonal antibodies was approximately 10% (data not shown). Significantly, levels of THP-1 infection by a Vero cell-propagated HSV1716 variant expressing T/260gD were 50-60% when cells were preincubated in Mab5 (FIG. 10j) or MabB (FIG. 10l) respectively and this higher level of infectivity was reduced to 20% when the THP-1 cells were preincubated in MabT (FIG. 10k). Similarly, the Vero cell propagated HSV1716 variant expressing T/274gD infected 50-60% of THP-1 cells preincubated with either Mab5 or MabB respectively and this was reduced to approximately 20% by preincubation of the cells in MabT (data not shown). The Vero cell propagated HSV1716 variant expressing 5/274gD infected 10% of THP-1 cells irrespective of whether the cells were preincubated in Mab5, MabT or MabB (data not shown).

Infection of TolB cells by the Vero cell propagated HSV1716 variant expressing 5/260gD was unaffected by preincubation of the cells in Mab5 (FIG. 10m), MabT (FIG. 10n) or MabB (FIG. 10o) with approximately 20-30% of cells infected in each case, which, in this experiment, was similar to HSV1716V infection of TolB cells preincubated with each of these monoclonal antibodies (data not shown). In contrast, the Vero cell propagated HSV1716 variant expressing T/260gD infected 50-60% of TolB cells when preincubated in Mab5 (FIG. 10p) or MabB (FIG. 10r) respectively and this higher level of infectivity was reduced to 10% when the TolB cells were preincubated in MabT (FIG. 10q). Similarly, the Vero cell propagated HSV1716 variant expressing T/274gD infected approximately 40% of TolB cells preincubated with either Mab5 (FIG. 10v) or MabB (FIG. 10x) and this was reduced to 20% by preincubation of the cells in MabT (FIG. 10w). In contrast, the Vero cell propagated HSV1716 variant expressing 5/274gD only infected 10-20% of TolB cells preincubated in Mab5 (FIG. 10s), MabT (FIG. 10t) or MabB (10u).

We also designed a series of targeted viruses which, under control of the constitutively active CMV-IE promoter, endogenously expressed scFvs 5, T, B or 8 fused to 274gD. These HSV1716 variants were generated using our novel HSV1716GateRed site-specific recombination system and their genomic structures at the RL1 loci were confirmed by PCR using primers that amplify across the HSV1716 ICP34.5 deleted region (FIG. 11a). PCR, using F13/R13 primers, with wild type HSV-1 17+ DNA as template generated an c880bp band (FIG. 11a, lane 8) compared to HSV1716 DNA which generated a 125bp product (FIG. 11a, lane 7). As the targeted HSV1716 variants contained both PGK-gfp and CMV-scFv/274gD expression cassettes in the RL1 loci, the DNAs from the HSV1716 variants expressing 5/274gD, T/274gD, 8/274gD and B/274gD generated 3500 bp products (FIG. 11a, lanes 1 and 3-5 respectively). A 3,500 bp product was also obtained from an HSV1716 variant in which the 5/274gD expression cassette was in the opposite orientation (FIG. 11a, lane 2) relative to PGK-gfp but no products were obtained using DNA extracted from mock-infected BHK cells (FIG. 11a, lane 6).

Expression of the scFv/274gD fusion proteins following infection of BHK cells was confirmed by Western blotting of whole cell extracts using an anti-myc tag monoclonal antibody (FIG. 11b). A prominent 45 kDa protein was detected in whole cell extracts obtained after infection of BHK cells with HSV1716 variants expressing 5/274gD (FIG. 11b, lane 2), B/274gD (FIG. 11b, lane 3), T/274gD (FIG. 11b, lane 4) and 8/274gD (FIG. 11b, lane 5) which was absent from mock-infected (FIG. 11b, lane 11) or BHK cells infected with HSV1716 (FIG. 11b, lane 12). The HSV1716 variant in which the 5/274gD expression cassette was in the opposite orientation (5/274gDopp) relative to PGK-gfp failed to express a detectable protein product (FIG. 11b, lane 1). SDS-PAGE/Western blotting was also performed using the anti-myc monoclonal antibody on $1 \times 10^6$ pfu HSV1716 variants expressing 5/274gD (FIG. 11b, lane 6), B/274gD (FIG. 11b, lane 8), T/274gD (FIG. 11b, lane 9) and 8/274gD (FIG. 11b, lane 10) and also 5/274gDopp (FIG. 11b, lane 7) with prominent 45 kDa bands detected in all but 5/274gDopp.

Expression of the scFv/274gD protein in infected cells was also demonstrated by immunoflourescence with FIG. 11c-n clearly showing both gfp expression resulting from viral infection and, using the anti-myc tag monoclonal antibody, cytoplasmic/perinuclear distributions of 5/274gD (FIGS. 11c and d), B/274gD (FIGS. 11e and f), T/274gD (FIGS. 11g and h) and 8/274gD (FIGS. 11i and j). Only gfp expression was observed in cells infected with HSV1716gfp (data not shown) and with the variant 5/274gDopp (FIGS. 11k and l) which failed to produce a protein product. Mock infected BHK cells are shown in FIGS. 11m and n. These viruses, along with HSV1716B, at 1 pfu/cell were used to infect CHO, CHO/DAF, SupT, THP-1 and TolB cells either in the presence or absence of Mab5, MabT, MabB or Mab8 and levels of infection were determined by fluorescence microscopy. THP-1 and SupT are respectively monocyte and T-cell lines that expresses CD38 (FIGS. 12a and b) but not CD20 (FIGS. 12d and e) and TolB is a B-cell line that expresses both CD38 (FIG. 12c) and CD20 (FIG. 12f). The weak fluorescence observed with Mab5/TolB suggests that CD20 is expressed at lower levels compared to CD38 in this and the other lines. We also created a CHO cell line (CHO/DAF) that constitutively expressed human DAF (CD55) as demonstrated by immunofluorescence with MabB (FIG. 12g) and a recombinant minibody version of MabB (FIG. 12h) with intense membrane staining of CD55 in the modified CHO cells which was not detected in normal CHO cells (FIG. 12i).

Only a small number of CHO cells were infected by the HSV1716 variants expressing 5/274gD, T/274gD, B/274gD or 8/274gD (FIG. 12j-m respectively) compared to approximately 20% of CHO cells with HSV1716B (FIG. 12n). Compared to CHO cells, 5/274gD (FIG. 12o), T/274gD (FIG. 12p) and 8/274gD (FIG. 12r) were better able to infect CHO/DAF cells but the numbers of infected cells were still much lower (<5%) than the 30% of cells infected by HSV1716B (FIG. 12s). Significantly, the HSV1716 variant expressing B/274gD was able to infect approximately 50% of CHO/DAF cells (FIG. 12q) and, by preincubating the CHO/DAF cells in MabB (FIG. 12v) or the recombinant minibody B (FIG. 12w), this level of infectivity was reduced to approximately 5%. Preincubation of CHO/DAF cells in Mab5 (FIG. 12t), MabT (FIG. 12u) or Mab8 (not shown) had no effect on the infectivity of the HSV1716 variant expressing B/274gD with approximately 50-60% of cells infected and preincubation in MabB failed to compromise the infectivity of HSV1716B for CHO/DAF cells (FIG. 12x).

The fluorescence microscopy data was confirmed by Western blotting using an anti-HSV-1 R1 antiserum to probe whole cell extracts from CHO/DAF cells (FIG. 13). R1 expression was only detected in CHO/DAF cells infected with 1 or 5 pfu/cell of the HSV1716 variant expressing B/274gD (lanes 3, 4) or HSV1716 propagated on BHK cells (lanes 7, 8) with little or no expression detected in CHO/DAF cells infected with HSV1716 variants expressing 8/274gD (lanes 1, 2), T/274gD (lanes 5, 6), or HSV1716 propagated on Vero cells (lanes 9, 10). Prominent R1 bands were detected when all of these viruses were used to infect Vero cells (lanes 11-20) and no band was observed in mock-infected Vero cells (lane 21). Thus, viruses that display a targeting moiety against DAF are better able to infect CHO cells with membrane exposed DAF than viruses that do not display a targeting moiety or display targeting moieties directed against CD20, CD38 or EGFR not present on CHO or CHO/DAF cells.

The HSV1716 variant expressing 5/274gD was able to infect approximately 5% of SupT cells (FIG. 14a), 5% of THP-1 cells (FIG. 14b) and 10% of TolB (FIG. 14c) and these levels were similar to those obtained using 5/274gDopp which infected similar numbers of SupT (FIG. 14d), THP-1 (FIG. 14e) and TolB (FIG. 14f). Significantly, the HSV1716 variant expressing T/274gD was able to infect 20%, 50% or 50% respectively of SupT (FIG. 14g), THP-1 (FIG. 14h) or TolB (FIG. 14i) cells suggesting that the incorporation of the CD38 targeting moiety in this virus improves its ability to infect CD38 positive cells. In contrast the HSV1716 variants expressing either 8/274gD or B/274gD were respectively able to infect only 5% or 10% of SupT cells (FIGS. 14j and m), 5% or 10% of THP-1 cells (FIGS. 14k and n) or 20% or 10% of TolB cells (FIGS. 14l and o). In this experiment, HSV1716V and HSV1716B respectively infected 10% or 20% SupT, 10% or 20% THP-1 or 20% or 40% TolB cells (data not shown). Further evidence that the presence of scFvT enhanced infectivity of CD38 positive cells was provided using the above viruses to infect SupT, THP-1 or TolB cells preincubated in Mab5, MabT, Mab8 or MabB with the results respectively summarized in Tables 5-7 and some examples shown in FIG. 15. The abilities of HSV1716 variants expressing 5/274gD, B/274gD or 8/274gD were all within the ranges obtained with the control viruses 5/274gDopp, HSV1716V or HSV1716B for SupT, THP-1 or TolB cells and theses low levels of infection were not affected by preincubating the cells in Mab5, MabT, MabB, Mab8 or control medium (Tables 5-7). Only the HSV1716 variant expressing T/274gD showed increased levels of infectivity for each of the SupT, THP-1 or TolB cells lines and, although this level of infectivity was unaffected by prior incubation of the cells in Mab5, MabB, Mab8 or control medium, it was compromised by preincubation in MabT. For example, in FIG. 15, approximately 25-30% of SupT cells were infected with the HSV1716 variant expressing T/274gD and this level of infection was unaffected by preincubation in Mab5 (FIG. 15a), Mab8 (FIG. 15c) or MabB (FIG. 15d) but was reduced to only 5% by preincubation in MabT (FIG. 15b). In contrast, approximately 10% of SupT cells were infected by the HSV1716 variant expressing 8/274gD and this level of infectivity was unaffected by preincubation in Mab5, MabT, Mab8 or MabB (FIG. 15e-h respectively).

Similarly, approximately 60-80% of THP-1 cells were infected with the HSV1716 variant expressing T/274gD and this high infectivity was not compromised by preincubation in Mab5 (FIG. 15*i*), Mab8 (FIG. 15*k*) or MabB (FIG. 15*l*) but was reduced to approximately 20% by preincubation in MabT (FIG. 15*j*). In contrast, approximately 20-30% of THP-1 cells were infected by the HSV1716 variant expressing B/274gD and this level of infectivity was unaffected by preincubation in Mab5, MabT, Mab8 or MabB (FIG. 15*m-p* respectively). For TolB cells, approximately 50-60% were infected with the HSV1716 variant expressing T/274gD and this level of infection was unaffected by preincubation in Mab5 (FIG. 15*q*), Mab8 (FIG. 15*s*) or MabB (FIG. 15*t*) but was reduced to approximately 10% by preincubation in MabT (FIG. 15*r*). In contrast, approximately 20% of TolB cells were infected by the HSV1716 variant expressing 5/274gD and this level of infectivity was unaffected by preincubation in Mab5, MabT, Mab8 or MabB (FIG. 10*u-x* respectively). Thus, evidence that antibody binding sites displayed on the HSV1716 envelope significantly alter tropism is provided by the HSV1716 variant displaying scFvT which demonstrated enhanced infectivity for CD38 positive cell lines with these augmented infection levels specifically inhibited by the corresponding monoclonal antibody.

The anti-EGFR scFv, derived from monoclonal antibody 8, was linked to 274gD and the resulting construct was used to create an HSV1716 variant that expressed the scFv8/274gD targeting moiety by site-specific recombination using HSV1716GateRed DNA. Two independent isolates, HSV1716EGFR1 and HSV1716EGFR2 were prepared.

The human epidermoid carcinoma cell line A431 expresses EGFR as shown by immunofluorescence with Mab 8 (FIG. 16) and was readily infected by HSV1716 (not shown) and by HSV1716EGFR1 and HSV1716EGFR2 (FIG. 16). The A431 cells were used to form subcutaneous tumours in nude mice and, once established, the mice were systemically injected in the tail vein with PBS or $1\times10^6$ pfu HSV1716, HSV1716EGFR1 or HSV1716EGFR2 on days 1 and 3. Tumours were measured daily and once they had reached 15 mm diameter the mice were sacrificed and tumour tissue obtained for immunohistochemistry with an anti-HSV-1 antiserum.

Mice that received the control PBS injection had more rapidly growing tumours than mice that received $1\times10^6$ pfu HSV1716 (FIGS. 17*a* and *b*) and were sacrificed sooner (FIG. 18). Significantly, mice that received $1\times10^6$ pfu HSV1716EGFR1 (FIG. 17*a*) or HSV1716EGFR2 (FIG. 17*b*) had more slowly growing tumours than those which were injected with HSV1716 (FIGS. 17*a* and *b*) and therefore survived longer (FIG. 18). The mean survival times for no virus, HSV1716, HSV1716EGFR1 and HSV1716EGFR2 were 10, 19, 25.5 and 23 days respectively indicating that the targeted viruses were better able to reduce tumour burdens and therefore enhance survival. Interestingly, after sacrifice and excision, the tumours on mice receiving intravenously injected HSV1716EGFR1 and EGFR2 were actually much smaller than measurements suggested as they formed a capsule-like structure, the majority of which was cellular debris, presumably a consequence of rampant viral lysis. Consistent with this, large amounts of virus were extracted from tumours of mice injected with HSV1716EGFR1 compared to HSV1716-injected mice. Thus, $3.1\times10^5$, $5.2\times10^6$ or $8.7\times10^6$ pfu were extracted from tumours of mice sacrificed on days 16, 23 or 24 respectively after HSV1716EGFR1 injection compared to 0, 0 or $4.1\times10^3$ pfu extracted from HSV1716-injected mouse tumours on days 16, 17 or 17 respectively. The failure to detect any virus in ⅔ HSV1716-injected tumour extracts is consistent with the small localized foci of virus replication observed immunohistochemically in these tumours (see below, FIG. 19*c*) or, alternatively, after intravenous injection, little or no unmodified HSV1716 lodged in these tumours. No virus was extracted from the skin, heart, liver, gut, lung, brain, bone, spleen or kidney of several mice injected with HSV1716EGFR1 and this lack of virus in these organs was confirmed using an HSV-1 specific PCR with DNA extracted from these tissues as template.

Immunohistochemistry (FIG. 19) confirmed this by demonstrating exceedingly high levels of HSV1716EGFR1 and HSV1716EGFR2 replication within tumours when compared with HSV1716. Immunohistochemical analysis of excised tumours clearly demonstrated widespread virus replication following injection of HSV1716EGFR1 and 2 (FIGS. 19*a* and *b*) compared to the more localized foci of unmodified HSV1716 replication (FIG. 19*c*) with no virus replication detected in the PBS-injected control (FIG. 19*d*). Thus, systemic delivery of tumour targeted HSV1716 is more effective at reducing tumour burdens and enhancing survival than untargeted HSV1716.

Further evidence of the ability of 8/274gD to target HSV1716EGFR1 was provided by intraperitoneal injection of nude mice bearing subcutaneous A431 tumours. On days 1, 3, 5, 6 and 9 the mice were injected with PBS or $2\times10^6$ pfu HSV1716 or HSV1716EGFR1. When injected by this route, HSV1716 was ineffective as the median survival time for both PBS- and HSV1716-injected mice was 18.5 days. At this time, the tumours on HSV1716EGFR1 mice were significantly smaller (e.g. on day 17; HSV1716=736±156 mm vs HSV1716EGFR1=244±60 mm, p value=0.033 and on day 20; HSV1716=843±142 mm vs HSV1716EGFR1=388±107 mm, p value=0.04) resulting in a prolonged median survival of 28 days for the HSV1716EGFR1-injected mice. Thus, by intraperitoneal injection, presumably, insufficient or no HSV1716 must reach the subcutaneous tumours to have any effect on tumour growth whereas targeting the virus to EGFR on the tumour cell surface promoted tumour uptake and prolonged survival.

Discussion

Recent Phase 1 clinical trials have demonstrated an excellent safety profile following direct intratumoral injection of oncolytic HSV1716 and the efficacy of this virus is being investigated currently in a Phase II/III trial for the treatment of recurrent glioma. It is clear, however, that the therapeutic usefulness of HSV1716 will be greatly facilitated if the virus can be administered via the circulation. In addition, the platform of tumour indications viz haematological tumours and metastatic disease, susceptible to oncolytic viral therapy could be greatly expanded. Incorporation of tumour-targeting moieties into the virus structure is a prerequisite for such strategies.

We have analysed the suitability of various glycoprotein fragments to direct the incorporation of N-terminally fused single chain antibodies into the HSV-1 envelope and assessed the abilities of incorporated fusion proteins to alter the tropism of the virus. Although scFv/glycoprotein fusion proteins have been used to redirect the tropism of various different viruses, including HSV-1 (Menotti et al 2006), these studies have used the scFv linked to almost full length glycoproteins close to the N terminus and optimization of incorporation and targeting ability have not been analysed. We linked a scFv from the well-characterised anti-GD3 ganglioside monoclonal antibody, R24 to 15 sequentially deleted gD fragments and to full length gH and gL which form a heterodimer with both proteins required for its correct folding and membrane presentation.[44] Linking the scFvs to both gH and gL could result in the formation of dimeric scFvs with enhanced avidity and to promote this, the size of the linker between the scFv and the N terminus of gL was varied.

All of the constructs were created in mammalian cell expression vectors for stable cell line production with the plasmids used for tandem expression of gH and gL fusion proteins providing different antibiotic resistances. The resultant R24/glycoprotein fusion proteins were incorporated into virus by infecting the cell lines with HSV1716 expressing green fluorescent protein and epitope tagging of the fusion proteins allowed estimations of their levels of expression and incorporation into virus. The infectivity of the viruses derived from stable cell lines was assessed using fluorescence microscopy to monitor gfp expression in CHO cells which stained positively with R24. Since CHO cells are non-permissive for Vero cell propagated HSV1716 infection, they provided an excellent system to assess alterations to viral tropism.[45] HSV-1 is endocytosed by CHO cells but infection requires that the cells express an HSV-1 receptor such as nectin-1.[46,47] In normal CHO cells, endocytosed HSV-1 is destroyed but this process is prevented by the presence of the HSV-1 receptor and the virion glycoproteins gB, gD and gH/gL in the cells.

Using an anti-myc monoclonal antibody in Western blotting to probe extracts from stably expressing Vero cell lines, only 2/15 R24/gD fusion protein constructs failed to produce detectable amounts of protein. This is presumed to be due to scFv fusion to this gD residue resulting in unstable proteins that are rapidly degraded. Of the expressed R24/gD fusion proteins, only two gD chimaeras were not detected in virus despite both incorporated and excluded glycoprotein fusion proteins having the same apparent cellular localizations. This is likely to be due to some structural defect in the non-incorporated proteins which prevented their assimilation into the viral envelope.

Both R24 and anti-CD38 scFvs linked to a number of gD deletions and also independently incorporated into gH/gL heterodimers were able to redirect HSV1716 infectivity. Out of 11 R24/gD fusion proteins which showed virus incorporation, six, in which R24 was linked to residues 37, 78, 92, 128, 260 and 274 were able to influence viral tropism with between 10% and 60% of normally non-permissive CHO cells infected compared to less than 1% with the remaining R24/gD. A greater influence on CHO cell infectivity was observed using viruses displaying R24 linked to gD residues 260 and 274. These smaller polypeptides may represent the minimum gD fragments required for optimum membrane incorporation and display of the receptor-binding scFv. However, as there was considerable variation in infection levels amongst the six R24/gD fusion proteins that mediated CHO cell penetration, other factors, such as scFv conformation and stability and antigen binding site display and accessibility, must also be involved. Attachment of the scFv to a number of different residues within gD region 139-239 resulted in fusion proteins which were poorly incorporated into virus and failed to significantly redirect HSV1716 tropism. Thus, either the low levels of fusion proteins with R24 linked to 139gD, 179gD, 191gD, 207gD or 239gD were insufficient to instigate receptor mediated penetration or scFv attachment to these amino acids resulted in structural destabilization and loss of antigen binding.

Although the ability of a subset of R24/gD fusion proteins to direct CHO cell infection strongly suggests that these chimaeric proteins alter HSV1716 tropism, conclusive proof was not obtained as CHO cell infectivity could not be blocked specifically using the parental R24 monoclonal antibody. Although preincubation with the R24 Mab greatly reduced CHO cell infectivity mediated by the six R24/gD fusion proteins, it also reduced the levels of CHO cell infectivity by HSV1716 propagated on BHK cells and we were unable therefore to distinguish between a specific or non-specific inhibition of viral entry by R24 bound to GD3 ganglioside on the cell surface. However, in subsequent experiments using an anti-CD38 monoclonal antibody and CD38-expressing THP-1 cells a specific inhibition of infection was demonstrated.

It has been shown that the tropism of an oncolytic measles virus was redesigned using scFvs to CD38 or CD20 linked to the measles virus envelope glycoprotein H.[20-21] The human monocyte cell line THP-1 is CD38 positive but CD20 negative and is semi-permissive for HSV-1 infection with 10-20% of cells infected by 1 pfu/cell HSV1716. ScFvs were derived from monoclonal antibodies that recognize CD20 (scFv5) or CD38 (scFvT) and viruses were propagated on stable Vero cell lines constitutively expressing either scFv5 or scFvT linked to gD residues 37, 128, 260 or 274. The number of THP-1 cells infected by viruses displaying 5/37gD, 5/128gD, 5/260gD or 5/274gD was similar to the numbers infected by HSV1716 propagated on Vero cells and these levels of infection were unaffected by preincubation of the cells in Mab5, MabT or control medium. Higher levels of THP-1 cell infection resulted from viruses displaying scFvT linked to gD residues 37, 128, 260 or 274 indicating that these viruses were able to use CD38 as a receptor for viral entry and, significantly, preincubation of THP-1 cells in MabT but not in Mab5 or control medium greatly reduced their infection rates. Thus, although HSV1716 can infect some THP-1 cells, indicating the presence of an HSV-1 receptor, most likely HVEM, receptor-binding sites must be limited either because of low levels of the receptor or poor accessibility on the cell surface. The presence of a CD38-binding moiety displayed on the virus coupled with the cognate antigen on the cellular membrane, must increase the proportion of specific virus/cellular interactions which result in augmented infection. As with the R24/gD fusion proteins, T/260gD and T/274gD were better targeting moieties than T/37gD or T/128gD fusion proteins indicating that these small gD fragments are sufficient to ensure efficient membrane incorporation and appropriate scFv display.

Previous reports have identified gC and gD fusion proteins which have altered HSV-1 tropism but, to the best of our knowledge, this is the first description of the construction of receptor-binding fusion proteins based on the gH/gL heterodimer. By linking the scFv to the N terminus of full length gH and gL and by varying the size of the spacer arm linkage between the scFv and gL, fusion proteins that overcame the non- and semi-permissivity of CHO and THP-1 cells were produced. We postulated that during formation of the gH/gL complex, the N-terminal scFvs may form dimers that would increase the avidity for cognate antigen binding leading to enhanced infectivity. Certainly, there was some variability in the CHO cell infection levels of the R24/gL constructs with 0, 1, 2 or 3 copies of the Gly-Gly-Gly-Gly-Ser spacer and the highest levels of infection were obtained using the R24/gL fusion proteins with 1 or 2 copies of the spacer.

However, the 30-40% of CHO cells infected by viruses displaying either the R24/gH/gL1 or R24gH/gL2 fusion protein heterodimers was lower than the 50-60% of CHO cells infected by viruses displaying either R24/260gD or R24/274gD suggests that the gH/gL heterodimer is less efficient than the small gD fragments at scFv display/presentation. Possibly, the R24/gH/gL heterodimers are present at lower concentrations in the viral envelope than the R24/260gD or R24/274gD fusion proteins or alternatively, the scFv stability or accessibility in the gH/gL heterodimer is sub-optimal. As with the R24/gD fusion proteins, a virus displaying scFvT in the gH/gL heterodimer infected higher numbers of THP-1 cells compared to a similar virus displaying scFv5 and the level of infection was reduced by MabT but not by Mab5 or control medium and the T/gH/gL2 heterodimer was less efficient at directing THP-1 cell infection than either T/260gD or T/274gD. Despite this, scFv displayed as part of the gH/gL heterodimer were able to influence the tropism of HSV1716 and may provide an additional/alternative targeting route.

Our initial analysis using infection of Vero cell lines to achieve viral assimilation of targeting moieties identified an efficient scFv mediated route to influence HSV1716 tropism. However, although this cell-based system was a convenient method to analyse a large number of different fusion protein constructs, production of targeted viruses is restricted to propagation on the appropriate cell line. Recombinant viruses expressing the targeting moieties during infection will be required and we produced a series of recombinant HSV1716 viruses expressing scFvs 5, T, 8 and B linked to 274gD. These viruses were created using an efficient and rapid site-specific recombination protocol based on the Gateway cloning system. A single in vitro recombination reaction circumvented the need for any in vivo recombination in bacteria or tissue culture cells and variants were typically isolated in 5-7 days. Also the efficiency of the in vitro recombination reaction was not compromised by the large 3 kbp inserts used in this study and other advantages include the use of very small amounts of viral DNA/entry plasmid and easy detection of contaminating non-recombinant DsRed viruses by fluorescence microscopy. PCR confirmed the genomic structure at the RL1 loci of the HSV1716 variants with inserted 5/274gD, T/274gD, B/274gD and 8/274gD transgenes and Western blotting confirmed both expression of the 45 kDa fusion proteins and their incorporation into virus. The orientation of the scFv/274gD expression cassette relative to the PGK-gfp expression cassette was important as one virus, in which 5/274gD was in reverse orientation resulting in the close juxtaposition of the CMV-IE and PGK promoters, failed to express the scFv/gD fusion protein. Elements of the PGK promoter immediately adjacent to the CMV-IE promoter must inhibit its transcriptional ability.

HSV1716 variants that express scFvB and scFvT, linked to 274gD, redirected the tropism of the virus allowing infection of non-permissive, DAF-positive CHO cells and semi-permissive CD38-positive SupT, THP-1 and TolB cells respectively. Viruses displaying an anti-EGFR scFv linked to 274gD were unable to infect EGFR negative CHO/DAF, SupT, THP-1 and TolB cells. Infection mediated by scFvB was dependent on specific antibody/antigen interactions as MabB or a recombinant MabB minibody specifically blocked infection of CHO/DAF cells by the HSV1716 variant expressing B/274gD whereas unrelated Mabs T, 8 or 5 had no effect. Similarly, increased infection levels of SupT, THP-1 and TolB cells by the HSV1716 variant expressing T/274gD were specifically inhibited by MabT but not by Mabs 5, 8 or B.

We attempted to produce other HSV1716 recombinants with redirected tropism using scFv 5, T, B or 8 each linked to gD residues 37, 92 and 128 but the resultant viruses had impaired replication and were difficult to plaque purify (data not shown). Structurally, the gD extracellular domain (amino acids 1-315) consists of N- and C-terminal extensions flanking a central Ig-folded core comprising residues 56-184 with HVEM or nectin-1 binding respectively requiring residues 1-34 or 34-243.[98-51] Therefore, apart possibly from scFv/37gD, none of these scFv/gD fusion proteins will be able to bind either HVEM or nectin-1 and their incorporation into virus at the expense of native gD or other essential membrane glycoproteins probably prevented the formation of infectious progeny. Propagation of the targeted viruses on BHK cells engineered to express the targeted antigen may circumvent this restriction. We were able to produce HSV1716 variants expressing scFvB and T linked to 260gD and these, similar to viruses expressing B/274gD and T/274gD were able to infect efficiently CHO/DAF and SupT/THP-1/TolB cells respectively. We also attempted to produce HSV1716 variants expressing scFvs 5, T, 8 or B linked directly to the N-terminus of gH and to gL via 1, 2 or 3 copies of the linker but, again, these viruses replicated poorly and were difficult to purify (data not shown). Possibly, the addition of 12 kbp to the viral genome by insertion of the PGK-gfp, scFv/gL and scFv/gH expression cassettes into both copies of RL1 reduced stability and packaging efficiency or, more likely, the expression/incorporation of scFv/gH and scFv/gL prevented normal assimilation of essential membrane glycoproteins and the resultant progeny were non-viable. Again, growth of the scFv/gH/gL viruses on modified BHK cells that express the targeted antigen may alleviate this restriction.

Using the EGFR-positive human squamous cell carcinoma cell line A431 to form subcutaneous tumours in nude mice, we were able to demonstrate that systemically delivered HSV1716 targeted to EGFR by an anti-EGFR scFv linked to 274gD was better able to destroy tumours and promote survival than unmodified HSV1716. Thus, two independently isolated variants of HSV1716 expressing 8/274gD reduced the tumour burden and prolonged survival compared to HSV1716. Indeed, the targeted viruses performed better than our data suggests as a number of mice which received HSV1716EGFR1 and HSV1716EGFR2 were killed prematurely because, although their apparent tumour diameters were 15 mm, when the tumours were excised after sacrifice the bulk of the mass consisted of cellular detritus surrounding a much reduced tumour. Presumably, the EGFR binding capability of the targeted HSV1716 variants augmented greatly the number of viruses locating to the tumour compared to the untargeted HSV1716 and this initial higher dose of virus adsorbed from the circulation was responsible for greatly enhanced tumour destruction. Immunohistochemical and virus titration analysis of excised tumours confirmed this as levels of virus replication in mice injected intravenously with HSV1716 expressing 8/274gD were much higher than in mice receiving unmodified HSV1716. Further evidence of the efficacy of tumour targeting was provided using intraperitoneal injection. By this route of administration, HSV1716 had no discernable effect on tumour growth whereas HSV1716EGFR significantly reduced tumour growth and prolonged survival.

Although an HSV1716 variant expressing scFv5 linked to 274gD was produced, no data demonstrating its abilities to alter tropism was generated. The HSV1716 variant expressing 5/274gD did not enhance infection of the CD20 positive TolB cells although possibly, as Mab5 only reacted weakly with TolB cells, there was insufficient CD20 available to mediate viral penetration or, alternatively, as the recombinant minibody version of Mab5 did not react with TolB cells (data not shown), there was a loss of binding affinity or specificity during conversion to the single chain format.

These studies were performed to identify a reliable method for redesigning the tropism of oncolytic herpes simplex virus such that systemically delivered virus will be more effectively targeted to tumour cells. We have developed a plasmid-based system to link a monoclonal antibody-derived scFv to gD residue 274 and recombinant viruses which display the targeting scFv are produced rapidly using a novel in vitro site-specific recombination system. ScFvs have been used previously to target HSV-1 with an anti-EGFR scFv linked to the gD-binding domain of nectin-1 creating a soluble bridging molecule capable of attaching the virus to CHO cells displaying EGFR on their surface and insertion of an anti-HER2/neu scFv at gD residue 24 to target the virus to CHO cells expressing the HER2/neu receptor.[35, 36] The soluble bridging molecule required gD to link virus and cell but the virus expressing the anti-HER2/neu scFv/gD fusion protein was gD negative. However, insertion of the scFv at residue 24 will only ablate HVEM binding and the chimaeric protein was still able to use nectin-1 as a receptor. Here, HSV1716 variants that express an anti-DAF scFv or an anti-CD38 scFv linked to gD residue 274 mediated infection via cognate antigen binding although the recombinant viruses retained gD and were still able to infect cells using either HVEM or nectin-1. Possibly, the fusion proteins can function as the sole receptor-binding protein to mediate infection of targeted cells as the scFv will mimic the specific interaction required to tether the virus closely to the cellular membrane and membrane fusion will be elicited via the remaining membrane-proximal residues of gD which form a pro-fusion domain required for recruitment of gB and gH/gL.[52] Currently, we are attempting to create a gD-negative HSV1716 variant but it is interesting to speculate whether a gD-negative virus is mandatory to achieve optimal tumour targeting. Certainly, the targeted HSV1716 expressing both full length gD and 8/274gD demonstrated enhanced tumour uptake and destruction compared to unmodified HSV1716 suggesting that adsorption by non tumour cells of the systemically injected HSV1716 variants is not a major issue. Neutralising antibodies that target gD may be a problem for such systemically administered HSV1716 variants and ablation of the gD ORF will prevent this. However, with such a virus, once a tumour has been infected, viral spread to other tumour cells in the mass will be totally dependent on a specific scFv/antigen interaction. As heterogeneity is a feature of many tumour types, not all cells will display the specific membrane protein and will therefore avoid infection. Perhaps, the presence of both scFv/gD fusion protein and gD in the virus envelope is a better configuration to allow efficient tumour targeting and optimum infection rates. Currently, the abilities of systemically delivered HSV1716 variants expressing various targeting scFvs to destroy tumour xenografts in mice are being assessed.

Materials and Methods

Cells and Viruses

BHK cells, CHO-K1 and Vero cells were grown as previously described.[45] Hybridomas MabR24, MabIF5 (Mab5), MabTHB-7 (MabT) and Mab108 (Mab8), expressing monoclonal antibodies against the ganglioside GD3, CD20, CD38 and EGFR respectively and the human leukaemic SupT, THP-1 and TolB cell lines, were obtained from ATCC/LGCpromochem, London, UK and were cultured in RPMI1640 medium supplemented with 10% NCS. Hybridoma HD1B (MabB) which expresses a monoclonal antibody that recognizes human decay accelerating factor (DAF/CD55), a kind gift from Dr Claire Harris, Dept. of Medical Biochemistry, University of Wales College of Medicine, Cardiff, UK, was also maintained in RPMI1640 medium supplemented with 10% NCS. HSV1716gfp is described in Harland et al and production of virus stocks is described in Conner et al.[6, 45]

Preparation of scFvs from Hybridoma Cells

Hybridoma cells were grown to high density and cell pellets obtained by centrifugation at 1000×g for 5 mins. Total RNA was extracted using the SV Total RNA kit (Promega, Southampton, UK) and cDNA prepared using the ImProm II Reverse Transcription System (Promega). Recombinant scFv variants of the monoclonal antibodies were derived from these cDNAs using the protocols and PCR primers described by Pope et al.[54] ScFv-encoding DNAs for each monoclonal antibody were prepared by RT-PCR amplification and linkage of antibody VH and VL sequences with the resultant scFv DNAs cloned into pGEM-Teasy (Promega) for DNA sequencing. The scFv-encoding DNAs were amplified using PCR primers that incorporate SfiI and NotI restriction enzymes sites at the 5' and 3' ends respectively for cloning in the phagemid vector pCANTAB6. Competent *E. coli* cells (strain HB2151) were transformed with the phagemid vectors and scFv expression by IPTG induction was confirmed by Western blotting (data not shown); scFvs expressed from pCANTAB6 have myc tags for detection.

Construction of pEL4, a Vector for scFv/Glycoprotein Fusion Protein Production

Plasmid pEL4 for expression of scFv/glycoprotein fusion proteins was created to allow PCR-amplified scFv DNAs to be cloned in-frame downstream of an IgG heavy chain leader sequence as SfiI/Not/fragments and in-frame upstream of a PCR-amplified HSV-1 glycoprotein DNA fragment. Initially, using pCANTAB6 with an R24 scFv insert as template, the scFv DNA was amplified using primers ELsfifor and R24notrev. Primer ELsfifor is a 99-base oligonucleotide [GAATTCATGGGATGGAGCTGTATCATCCTCTTCTT GGTAGCAACAGCTACAGGTGTCCACTCCGCGGC CCAGCCGGCCGATGTGCAACTGGTGGAGTCT] (SEQ ID NO: 7) that has a 5' EcoR1 site (in bold) then 63 bases (underlined) encode the R24 IgG heavy chain leader sequence followed by the R24 scFv 5' sequence with an intervening SfiI site (in bold and underlined). PCR with ELsfifor and R24notrev [GAGTCATTCTGCGGCCGC-CCGTTTTATCTCCAGCTTGGT] (SEQ ID NO: 8), the antisense primer exactly matching the 3' end of the R24 scFv with a NotI site (in bold), generated the R24 scFv DNA for cloning into the EcoR1/Not1 sites in the mammalian expression plasmid pCDNA4myc/HisA (Invitrogen, Paisley, UK) to generate pEL4. The presence of the IgG leader in this plasmid was confirmed by sequencing. The R24 scFv component in pEL4 can be readily exchanged with an alternative scFv, amplified by PCR using primers that provide flanking SfiI/NotI sites (Pope et al 1996).

Since each of the scFvs created in this study has a unique RsaI fingerprint, any scFv exchange was confirmed by PCR amplification of the scFv DNA and RsaI digestion (data not shown). Each fusion protein construct assembled in pEL4 consisted of a secretory leader sequence and N-terminal antibody domains for binding to a targeting ligand linked to C-terminal viral glycoprotein domains for virus incorporation.

Construction of Vectors for the Expression of scFv/Glycoprotein Fusion Proteins

Three HSV-1 glycoproteins, gD, gH and gL were used for fusion protein construction and the DNA fragments were PCR amplified from HSV1716 DNA.

For HSV-1 gD which comprises 393 amino acids with the TM domain located between aa 342-364, 15 random deletions sequentially removing aa 1-273 were PCR amplified using the 15 forward and common reverse primers shown in Table 1. The gD forward primers are identified by the extent of the N-terminal deletion (e.g. 108gD amplified a gD DNA fragment which starts at nucleotide 109 and encodes a gD polypeptide with 36 amino acids deleted from the N terminus). An additional A nucleotide between the Not1 site (in bold) and the gD sequences (underlined) ensured that the gD and scFv DNAs were cloned in frame; the Not1 site plus the additional A inserts an Ala-Ala-Ala linker between the scFv and glycoprotein domains of the fusion protein. The gD reverse primer lacked a stop codon and the XhoI site used for cloning ensured that the inserted fragment was in-frame with the Myc/His tags provided by the pCDNA4 parent vector. After PCR amplification from viral DNA, the gD fragments were sequentially digested with NotI followed by XhoI and ligated into the likewise digested pEL4 containing 5, T, B or 8 scFv DNAs. In some instances, the gD PCR fragments were cloned into pGEMT-easy and sequenced to confirm their identity (data not shown).

HSV-1 gH (838 amino acids) and gL (224 amino acids) form a heterodimer in the virus envelope and the complete coding sequences minus signal peptides for both these proteins were PCR amplified for cloning into pEL4. HSV-1 gH was amplified using the forward primer GGCCGCGGC-CGCAGTCCACGACTGGACTGAGCAGA (SEQ ID NO: 9), which amplifies from nucleotide 58 (gH sequence underlined) and incorporates a NotI site (bold) upstream for cloning in frame with the scFv of pEL4. The reverse primer, GGGCCCCTCGAG TTAGGCGTAGTCCGGGACATCATAGGGGTATTCGC GTCTCCAAAAAAACGGGAC (SEQ ID NO: 10), has a XhoI site (bold) for cloning and, in frame with the 3' gH sequence (underlined) minus stop codon, the primer incorporated an HA-tag sequence with stop codon (in bold and underlined). PCR amplified gH was sequentially digested with NotI followed by XhoI and ligated into the likewise digested pEL4 containing scFv 5, T, B or 8. To allow the antibody domains in the gH/gL heterodimer to interact, the scFv was tethered to the gL N terminus directly or by a flexible linker comprising 1, 2, or 3 copies of a Gly-Gly-Gly-Gly-Ser spacer. HSV-1 gL downstream of nucleotide 60 was PCR amplified using the forward and reverse primers shown in Table 1 which incorporate 5' NotI and 3' XbaI restriction enzyme sites for cloning into pEL4. The forward primers gL for 0, gL for 1, gL for 2 and gL for 3 respectively incorporate 0, 1, 2 or 3 copies of Gly-Gly-Gly-Gly-Ser to the N terminus of the gL and gLrev has no stop codon but is in-frame with the pEL4 Myc/His tags. PCR amplified gL DNAs were sequentially digested with NotI followed by XbaI and ligated into the likewise digested pEL4 with 5, T, B or 8 scFv inserts. For dual expression in the same cell, scFv/gH constructs were transferred as HindIII/XhoI fragments into p3.Hygro (Invitrogen), a vector which provides a CMV promoter and a hygromycin selection gene and the scFv/gL constructs were transferred as HindIII/PmeI fragments into pEF4Myc/His (Invitrogen), a vector with an EF-1a promoter and a zeocin selection gene.

For gD deletions, the scFv fusion proteins were designated according to the scFv used to make the construct with Mabs R24, 5, T, B and 8 providing the prefixes followed by the amino acid of gD to which it is linked. For example R24/128gD (amplified using primer 381gD) comprises the R24 scFv against GD3 linked to gD amino acid 128 with amino acids 1-127 deleted. For gH and gL fusion protein designation, 5gH/gL and 5gH/gL3 are the heterodimers comprising scFv5, against CD20, linked directly to gH and to gL either directly or with a 3x(Gly-Gly-Gly-Gly-Ser) spacer arm.

Production of Stable Cell Lines Expressing scFv/Glycoprotein Fusion Proteins

Vero cells were transfected with 50 ug scFv/gD fusion protein-encoding plasmids mixed with 10 ul lipofectamine 2000 (Invitrogen) in 250 ul of serum free DMEM/F12 medium. After 48-72 hours of transfection, cells were trypsinized and plated out with growth medium containing 1 mg/ml zeocin (Invitrogen). Cells were selected with the zeocin antibiotic for 2-3 weeks after which time individual clones were clearly visible. Cells were trysinized and cloned by limiting dilutions in 24-well plates. Clones were expanded and maintained in appropriate medium containing 1 mg/ml zeocin. For Vero cells expressing scFv/gH and scFv/gL fusion proteins, 50 ug of each plasmid was transfected in 20 ul lipofectamine 2000 in 250 ul serum free DMEM/F12 and, after trypsinisation and plating out, selection was achieved using 0.5 mg/ml zeocin/hygromycin in combination. Expression of scFv/glycoprotein fusion proteins was confirmed either by Western blotting or by immunofluorescence using either anti-myc or anti-HA monoclonal antibodies (New England Biolabs, Hitchin, UK).

For production of virus stocks, confluent monolayers of stable cell lines were infected with $1\times10^5$ pfu HSV1716gfp and, after 3-4 days of infection, total virus was harvested, purified by high-speed centrifugation and titrated on BHK cells. All yields were within the range obtained for HSV1716gfp infection of normal Vero cells (data not shown). The presence of scFv/glycoprotein fusion proteins in the virion was confirmed by Western blotting using either anti-myc or anti-HA monoclonal antibodies.

Production of Recombinant Viruses Expressing scFv/Glycoprotein Fusion Proteins by Homologous Recombination Previous analysis of results from stable cell lines identified potential tropism-altering constructs for recombinant virus production and the pEL4 constructs were used in two ways to generate HSV1716 variants expressing the relevant scFv/glycoprotein fusion proteins. In the first series of targeted viruses, plasmid sp73 (Promega) was used to assemble constructs prior to recombinant virus production. Initially, a gfp expression cassette was inserted into sp73 using the 1.3 kbp blunt-ended EcoRI/AflII fragment that contains the PGK promoter/gfp gene obtained by restriction digestion, followed by Klenow in-filling from the vector pSNRG (OligoEngine, Seattle, Wash., USA) and ligation into the sp73 vector cut with EcoRV then alkaline phosphatase treated. Successful insertion of the PGK/gfp DNA to create the vector sp73gfp was confirmed by XhoI/BglII digestion and the orientation of the inserted DNA identified using the unique XhoI site in sp73 and the unique BsrGI site at the 3' end of PGK/gfp.

The gC promoter was amplified from HSV-1 DNA by PCR as a SacI/KpnI fragment using primers gCforsac (GT-GAGCTCCCGAAGACCGCCGGTGTG (SEQ ID NO: 11), SacI in bold, gC promoter 5' sequence underlined) and gCrevkpn (AGGGTACCGGCAAAGCGAGACCGGG (SEQ ID NO: 12), KpnI site in bold, gC promoter 3' sequence underlined). After sequential SacI/KpnI digestion, the promoter DNA was ligated into SacI/KpnI digested sp73gfp to create the vector gCp73gfp. The TK promoter was amplified from HSV-1 DNA by PCR as a SalI/PstI fragment using primers TKforsal (AGAAGTCGACTAT GATGACA-CAAACCCCGCC (SEQ ID NO: 13), SalI site in bold, TK promoter 5' sequence underlined) and TKrevpst (GACTG-CAGTGCGGCACGCTGTTGACGCT (SEQ ID NO: 14), PstI site in bold, TK promoter 3' sequence underlined). After sequential SalI/PstI digestion, the promoter DNA was ligated into the likewise digested gCp73gfp to create the dual promoter vector gC/TKp73gfp.

The gD DNA components from the selected scFv/gD fusion protein constructs were re-amplified by PCR from HSV-1 DNA using the appropriate forward primers (Table 1 and the reverse primer GGCCCTCGAGGCATGC GCACCCATTAAGGGGGGGTATCTAGTAAAACAAGG GCTGGTGCGAG GA (SEQ ID NO: 15), which incorporates the gD stop codon and the 21 nucleotides immediately downstream of the gD stop codon in the HSV-1 genome (underlined in bold). The reverse primer also incorporates a XhoI site (in bold) and the NotI/XhoI-digested gD DNA was ligated into the likewise digested appropriate scFv-containing pEL4 to recreate the scFv/gD fusion protein. This was excised from the pEL4 plasmid by HindIII/XhoI digestion and ligated into the likewise digested gCp73gfp such that expression of the scFv/gD fusion protein is controlled by the HSV-1 gC promoter.

To construct a plasmid suitable for generating HSV1716 variants expressing scFv/glycoprotein fusion proteins, a shuttle vector for the insertion of transgenes in the RL1 loci, termed RL1-del was used. RL1-del was designed as a promoterless cloning vector suitable for generating ICP34.5 null HSV-1 and consists of an HSV-1 DNA fragment containing the RL1 gene and its flanking sequences with the majority of the ICP34.5 open reading frame removed and replaced with a multi-cloning sequence (MCS). The transgene to be inserted into the RL1 loci was ligated into the MCS of RL1-del and homologous recombination with HSV-1 DNA, driven by the RL1 flanking sequences, results in concomitant deletion of the ICP34.5 gene and incorporation of the desired transgene. RL1-del contains the HSV-1 BamHI k DNA fragment (123459-129403) which includes the RL1 gene and its flanking sequences cloned into the BamHI site of plasmid pGem-3Zf (Promega). The 477 bp PflMI/BstEII fragment from the RL1 ORF (125292-125769) has been removed to inactivate the ICP34.5 gene and replaced with a MCS providing unique restriction enzymes sites for BglII, NruI and XhoI.

The scFv/gD fusion protein and gfp expression cassettes were excised from their appropriate gCp73/gfp plasmids by BglII/XhoI digestion and ligated into RL1-del which was also BglII/XhoI digested. The AseI sites which flank the MCS of sp73 were used to excise the 6kbp DNA fragment containing the PGK/gfp, gCp/scFv/gL and TKp/scFv/gH expression cassettes from the relevant gC/TKp73gfp vectors and, after blunt ending with Klenow, the fragment was ligated into RL1-del digested with NruI and alkaline phosphatase treated. For any scFvs that contained AseI sites, the alternative DrdI sites flanking the sp73 MCS were used to excise the PGK/gfp, gCp/scFv/gL and TKp/scFv/gH expression cassettes. Approximately 50 ug of RL1-del plasmid with scFv/gD or scFv/gH/gL fusion protein inserts were linearized by XmnI digestion. After clean-up using a GFX kit (GE Healthcare, Little Chalfont, UK), the linearised plasmids were used in conjunction with HSV-1 DNA to cotransfect BHK cells.

RL1-del and viral DNA (100 ug) were mixed with 20 ul lipofectamine 2000 in 250 ul DMEM/F12 serum-free medium and added to a 60 mm plate which contained 50% confluent BHK cells. After 4 hours of incubation at 37° C., the medium was removed and the cells shocked for exactly 4 minutes with 25% DMSO. After 3 washes with 5 ml culture medium the cells were returned to 37° C. with 5 ml BHK medium and left for 72 hours. Cells were scraped into the supernatant, the mixture sonicated for 2 minutes and stored at −70° C. until required. Serial dilutions were plated out on Vero cells in 60 mm plates, individual green fluorescent plaques were picked, added to 1 ml culture medium and sonicated for 2 minutes before serial dilutions were again plated out on Vero cells. Plaque purification was repeated 6-10 times before stocks of HSV1716-scFv/gD or HSV1716-scFv/gL/gH were produced. The presence of either the scFv/gD or scFv/gL/gH expression cassettes in the RL1 loci of HSV1716 was confirmed by Southern blotting using the AluI/RsaI ICP34.5 fragment from plasmid pGEM34.5 (McKie et al 1994). Incorporation of these cassettes into RL1 alters the size of HSV-1 BamHI k fragment dependent on orientation of the insert relevant to the RL1 flanking sequences (scFv/gH/gL only) and/or the numbers of additional BamHI sites in the inserts (data not shown). In each of the viruses constructed, fusion protein expression was controlled by endogenous HSV-1 early (TK-scFv/gH) or late (gC-scFv/gD or -scFv/gL) promoters and although the expressed scFv/gH fusion protein retained its HA tag, the scFv/gD and scFv/gL fusion proteins lacked the vector-derived myc tags.

Production of Viruses Expressing scFv/gD Fusion Proteins by Site-Specific Recombination A series of targeted viruses was constructed using scFvs linked to myc-tagged 274gD using a novel in vitro site-specific recombination system. Central to this method was production of HSV1716GateRed, an HSV1716 variant, which contained Gateway destination sites located within each of the ICP34.5 deleted regions. The Gateway® Vector Conversion system (Invitrogen, Paisley, UK) provided DNA with attR site-specific recombination sequences for insertion into a vector of choice and was ligated into the EcoRV-digested and alkaline phosphatase-treated plasmid sp73 to create sp73gate. Once inserted in the plasmid, the DNA between the attR sites, encoding chloramphenicol resistance and the ccdB gene, was removed by Not1/BstXI digestion. The vector backbone was then blunt-ended with Klenow and alkaline phosphatase treated. The 1.3 kbp CMV-DSred expression cassette was excised from the plasmid pCMV-DsRed-Express (BD Biosciences, Cowley, UK) by AflII/NsiI digestion, blunt ended by Klenow and ligated into the sp73gate backbone to create the plasmid sp73gatered. The DNA consisting of the attR sites flanking the CMV-DSred expression cassette was excised from sp73gatered by BglII/XhoI digestion, blunt-ended with Klenow and ligated into the blunt-ended, alkaline phosphatase-treated BglII site in the plasmid RL1-del used for the production of HSV1716 variants by homologous recombination. RL1-del consists of the HSV-1 BamHI k DNA fragment (123459-129403) which includes the RL1 gene and its flanking sequences cloned into the BamHI site of plasmid pGem-3Zf (Promega). The 477 bp PflMI/BstEII fragment from the RL1 ORF (125292-125769) has been removed to inactivate the ICP34.5 gene and replaced with a MCS providing unique restriction enzymes sites for BglII, NruI and XhoI. The transgene to be inserted into the RL1 loci is ligated into the MCS of RL1-del and homologous recombination with HSV-1 DNA, driven by the RL1 flanking sequences, results in concomitant deletion of the ICP34.5 gene and incorporation of the desired transgene. Southern blotting confirmed that the Gateway destination sites flanking the DsRed expression cassette was cloned into both RL1 loci (data not shown).

The Gateway entry vector, pENTR1A was modified for use in our HSV1716 site-specific recombination system as follows. The DNA between the attL sites in pENTR1A was removed by EcoR1 digestion and the resulting vector backbone was blunt-ended and alkaline phosphatase treated. A green fluorescent protein expression cassette was inserted into the pENTR1A backbone by ligating it with the 1.3 kbp blunt-ended EcoRI/AflII fragment that contains the PGK promoter/gfp gene excised from the vector pSNRG (a kind gift from Dr B. Singh (MSKCC, New York, USA)). Although EcoR1 digestion removed the ccdB gene from pENTR1A, a number of other restriction sites between the attL flanking sequences were retained for insertion of additional gene/DNA sequences of interest to be cloned into HSV1716 alongside the PGK-gfp expression cassette.

Novel HSV1716 variants were created in vitro by incubating HSV1716GateRed DNA with the appropriate gene/DNA sequence of interest inserted in pENTR1A-gfp. HSV1716GateRed DNA was obtained by phenol/chloroform extraction of BHK cells 24 hours after infection with the HSV1716GateRed virus and, after 70% isoprpopanol precipitation, the DNA was resuspended in 1 ml nuclease free water. The expression cassettes for the scFv/274gD fusion proteins were excised directly from the appropriate pEL4 constructs as 2.5 kbp SspI/PvuII fragments which contained the CMV-IE promoter, the scFv/gD encoding DNA and the BGH polyadenylation signal. These fragments were ligated directly into the plasmid pENT1A-gfp, which had been BamHI digested, blunt ended with Klenow and alkaline phosphatase treated. For site-specific recombination reactions using these pENTR1A-gfp constructs, 5 ug plasmids and 3 ug HSV1716GateRed DNA were incubated overnight with LR clonase. After enzyme inactivation by Proteinase K digestion, the entire reaction mix (11 ul) was added to 25 µl of serum free DMEM/F12 (Invitrogen) medium containing 10 µl lipofectamine 2000 and used to transfect 50% confluent BHK cells in a 60 mm dish. After 4-6 hours the cells were shocked in 25% DMSO/PBS, washed and cultured in 5 ml of GMEM at 37° C. for 48-72 hours. Cells were harvested by scraping into the medium and, after 2 minutes sonication, 5 sequential 10-fold dilutions were plated out on Vero cells. The in vitro site-specific recombination reaction was very efficient and converted up to 90% of viral DNA from DsRed to gfp expression such that, a single plaque picked from the serially diluted plates was 100% pure with no DsRed virus contamination and was used for HSV1716 recombinant stock production as described. All yields were within the range obtained for HSV1716gfp infection of normal Vero cells (data not shown).

PCR, with primers that amplify across the ICP34.5 deleted region was used to confirm the appropriate genomic structure at the RL1 loci of these viruses. Viral DNA was prepared using a Wizard SV genomic DNA kit from BHK cells 24 hours after infection with the relevant viruses at 5 pfu/cell and 2 ul extracted DNA was used as template for amplification by RL1 PCR. In addition to the viral DNA, the 50 ul PCR mix contained 2 uM primer R13, 14 uM primer F3, 1 mM $Mg^{2+}$, 200 uM each of dATP, dGTP, dCTP, dTTP, 200 uM deazaGTP and 1.25U Platinum Pfx DNA polymerase (Invitrogen). The F3 primer sequence is CAGGCACGGCCCGATGACCGC-CTC (SEQ ID NO: 16) corresponding to bases 125172-125195 and complementary to bases 1176-1199 of the HSV strain 17+ sequence. Primer R13 sequence is GGCCA-GACGCCGAAAACG (SEQ ID NO: 17), complementary to bases 126035-126052 and corresponding to bases 319-336 of the HSV strain 17+ sequence. Primer F3 is positioned in the ICP34.5 coding region towards the 3'-end which is still present in HSV1716 and primer R13 lies outside the ICP34.5 ORF within the a sequence. The conditions for PCR were 94° C. for 2 minutes then 35 cycles of 94° C. for 15 seconds, 72° C. for 1 minute and 72° C. for 1 minute with a final extension of 72° C. for 2 minutes. Samples were then analysed on 1% agarose gels.

Production of CHO Cell Lines Expressing Human CD55 and a Recombinant MabB Minibody Plasmid pDAF, which contains a mammalian expression cassette for human CD55 with a hygromycin selectable marker, was a kind gift from Dr Claire Harris and was used to transfect CHO cells. Plasmid (50 ug) was mixed with 0.25 ml serum free DMEM/F12 medium containing 10 ul lipofectamine 2000 was added to CHO cells and, after 48 hours in culture, cells were trysinised and plated out in a T75 flask in growth medium supplemented with 0.5 mg/ml hygromycin. After 14 days in culture individual colonies of cells were trypsinised and, after cloning by limiting dilution, a stable hygromycin-resistant CHO cell line, termed CHO/DAF, which expressed CD55, as assessed by Western blotting using MabB, was produced. The CHO/DAF cell line was maintained in DMEM/F12 supplemented with 10% NCS and 0.5 mg/ml hygromycin.

Using the MabB scFv DNA cloned into pEL4, an expression cassette for a minibody construct comprising the scFv DNA linked to the human IgG1 CH2/CH3 (Fc) region DNA was prepared. The resultant expressed protein was able to dimerise via the IgG1 Fc region and was secreted into the medium from a stable CHO cell line isolated using the zeocin resistance gene of pEL4. The 5' and 3' primers for the amplification of the human IgG1 Fc DNA, which incorporate Not1 and Xho1 restriction sites (underlined), were respectively ACCTTGCA<u>GCGGCCGC</u>AAGACCCAAATCTTGT GACAAAACTC (SEQ ID NO: 18) and GATCACGT <u>CTCGAG</u>TTATCATTTACCCGGAGACAGGGAGAGGC TCTTTCTG (SEQ ID NO: 19) and these were used to amplify the 700 bp IgG1 Fc region from peripheral blood mononuclear cell total RNA by RT-PCR. The amplified fragment was cloned directly after RT-PCR into the PCR cloning vector pGEM-Teasy (Promega) and was sequenced to confirm its identity. The PCR fragment was digested sequentially using Not1 followed by Xho1 and ligated into the pEL4 plasmid containing scFvB to generate a plasmid that expresses the scFvB linked to the human IgG1 Fc region. CHO cells were transfected and selected as described above except that the growth medium contained 1 mg/ml zeocin for selection rather than hygromycin. Medium from zeocin-resistant stable cell lines was harvested after 5 days in culture and expression of the MabB minibody was confirmed by denaturing and non-denaturing PAGE/Western blotting using an anti-human IgG Fc antibody which identified respective 55kDa and 110kDa proteins (data not shown).

Fluorescence Microscopy/Western Blotting/Immunofluorescence

As HSV1716 variants used in this study expressed gfp, the infectivity of progeny viruses was assessed by fluorescence microscopy as described in Conner et al.[45] For Western blotting, the stable cell lines expressing scFv/glycoprotein fusion proteins were plated out in 35 mm plates and incubated for 24 hours at 37° C. in 5% $CO_2$. Cell lines to be infected with the various HSV1716 variants expressing scFv/274gD fusion proteins were plated out in 35 mm plates and incubated for 24 hours at 37° C. in 5% $CO_2$ before infection. For harvesting, cells were washed once with 1 ml PBS and whole cell extracts obtained by the direct addition of 0.2 ml SDS PAGE sample buffer. After SDS PAGE and transfer to nitrocellulose membranes, blots were probed with either anti-myc or anti-HA monoclonal antibodies diluted 1:1000. To determine the presence of scFv/glycoprotein fusion proteins in virions, $1 \times 10^6$ pfu purified virus were mixed with SDS PAGE sample buffer and analysed as described above. To assess infectivity of targeted viruses, confluent monolayers of cells were infected with $1 \times 10^7$ pfu virus and incubated for 8-24 hours before cells were harvested as described above. Blots were probed with a polyclonal antibody to the R1 subunit of the viral ribonucleotide reductase.[55] For immunofluorescence to detect scFv/glycoprotein fusion protein expression, the stable cell lines were plated out on glass coverslips and, after 18 hours in culture, cells were fixed in 4% paraformaldehyde. For immunofluorescence to detect scFv/274gD fusion protein expression by HSV1716 variants, BHK cells were plated out on glass coverslips and, cells were infected with the appropriate virus at 1 pfu/cell for 24 hours and fixed as described above. After blocking for 1 hour in 2% normal horse serum, cells were incubated overnight in either anti-myc or anti-HA monoclonal antibodies diluted 1:1,000, washed 4 times in PBS with 0.05% Tween (PBST) and incubated for 2-4 hours in anti-mouse IgG/FITC or IgG/Texas Red conjugates (Vector Laboratories Ltd) diluted 1:200. For recombinant minibody B, an anti-human Fc/FITC conjugate at 1:1000 was used After 4 washes in PBST, coverslips were mounted and analysed by fluorescence microscopy.

In Vivo Tumour Reduction Studies

Female 6-8 week old athyimic nude mice (Charles River Labs, UK) were maintained under specific pathogen free conditions. Actively growing A431 cells were harvested and after resuspension in PBS, 1×10⁶ cells per mouse were injected subcutaneously. When tumours reached 5 mm in diameter, the mice were injected either intravenously via the tail vein or intraperitoneally with PBS, HSV1716 or HSV1716EGFR1 or 2. Mice were inspected daily, when tumour volumes reached 15 mm they were sacrificed and the tumour xenograft removed for immunohistochemistry/viral extraction. The viral load in tumours and various organs was assessed by plaque forming assay on BHK cells. Extracted intact tumours/organs were frozen immediately at −70° C. and, after thawing, the tissues were mechanically homogenized in a Retsch homogenizer in 1 ml PBS prior to titration.

Immunohistochemistry for HSV-1

Prior to immunohistochemistry tumour samples were fixed for at least 24 hours in 4% paraformaldehyde before embedding and sectioning using standard protocols. Briefly, paraffin embedded sections were dewaxed, dehydrated and endogenous peroxidase activity quenched. Sections were blocked with 10% normal goat serum before incubation in an anti-HSV-1 polyclonal primary antibody (DakoCytomation, Ely, UK) diluted 1:1000. A biotinylated secondary antibody at 1:500 dilution, an avidin/biotin complex solution and the chromogen DAB (all from Vector Labs, Peterborough, UK) were then used to detect the primary antibody binding to tissue. The slides were counterstained, dehydrated mounted and analysed using light microscopy.

TABLE 1

Table 1 shows sequences of primers used for the PCR amplification of sequentially deleted gD fragments and for amplification of gL with 0, 1, 2 or 3 copies of the Gly-Gly-Gly-Gly-Ser spacer. Restriction sites are in bold and HSV-1 glycoprotein sequences are underlined.

| gD forward primers | | |
|---|---|---|
| 108gD | GGATCCGCGGCCGCAGCCGACCCCAATCGCTTTCGCGGC | (SEQ ID NO: 20) |
| 171gD | GGATCCGCGG CCGCAGGGGTCCGGCGCGTGTACCACATC | (SEQ ID NO: 21) |
| 231gD | GGATCCGCGGCCGCACTCCCGATCACGGTTTACTACGCC | (SEQ ID NO: 22) |
| 273gD | GGATCCGCGG CCGCACTCCCGATCACGGTTTACTACGCC | (SEQ ID NO: 23) |
| 312gD | GGATCCGCGGCCGCAATTGT CCGCGGGCC TCCGAAGAC | (SEQ ID NO: 24) |
| 381gD | GGATCCGCGGCCGCAGGAGGCAACTGTGCTATCCCCATC | (SEQ ID NO: 25) |
| 414gD | GGATCCGCGGCCGCAGAGTA CACCGAATGC TCCTACAAC | (SEQ ID NO: 26) |
| 489gD | GGATCCGCGGCCGCAGACAGCTTCAGCGCCGTCAGCGAG | (SEQ ID NO: 27) |
| 534gD | GGATCCGCGGCCGCACACGCCCCCGCGTTTGAGACCGCC | (SEQ ID NO: 28) |
| 570gD | GGATCCGCGGCCGCACGGCTCGTGAAGATAAACGACTGG | (SEQ ID NO: 29) |
| 618gD | GGATCCGCGGCCGCAGAGCACCGAGCCAAGGGCTCCTGT | (SEQ ID NO: 30) |
| 690gD | GGATCCGCGGCCGCACAGGCCTACCAGCAGGGGGTGACG | (SEQ ID NO: 31) |
| 714gD | GGATCCGCGGCCGCAGTGGACAGCATCGGGATGCTGCCC | (SEQ ID NO: 32) |
| 777gD | GGATCCGCGGCCGCAAGCTTGAAGATCGCCGGGTGGCAC | (SEQ ID NO: 33) |
| 819gD | GGATCCGCGGCCGCAACGAG CACCCTGCTG CCCCCGGAG | (SEQ ID NO: 34) |
| gD reverse primer | | |
| GGCCAAGCTTCTCGAGTCTAGAGTAAAACAAGGGCTGGTG CGAGGA | | (SEQ ID NO: 35) |
| gL forward primers | | |
| gLfor0 | GGCCGCGGCCGCATTGTCTTCAACCGAATATGTTAT | (SEQ ID NO: 36) |
| gLfor1 | GGATCCGCGGCCGCAGGTGGAGGCGGTTCA TTGTCTTCAA CCAATATGTTATT | (SEQ ID NO: 37) |
| gLfor2 | GGATCCGCGGCCGCAGGTGGAGGCGGTTCAGGTGGAGGCGGTTCA TTGTCTTCAACCGAATATGTTATT | (SEQ ID NO: 38) |
| gLfor3 | GGATCCGCGGCCGCAGGTGGAGGCGGTTCAGGTGGAGGCGGTTC AGGTGGAGGCGGTTCATTGTCTTCAACCGAATATGTTATT | (SEQ ID NO: 39) |
| gL reverse primer | | |
| GGCCAAGCTTGGGCCCTCTAGAGAGGCGCCGGGACTGGGGTCGTCG | | (SEQ ID NO: 40) |

TABLE 2

Table 2 shows expression and CHO cell infection data from R24 scFv linked to 15 N-terminal deletions of HSV-1 gD.

| Construct | Approx Mr (KDa) * | Vero cell expression ** | Virus incorp ** | Localization in Vero cells | CHO cell infectivity *** |
|---|---|---|---|---|---|
| R24/37gD† | 70 | ++ | ++ | perinuclear | 30% |
| R24/58gD | 67 | n.d. | n.d. | n.d. | <1 |
| R24/78gD† | 65 | ++ | ++ | perinuclear | 10% |
| R24/92gD | 64 | ++ | ++ | perinuclear | 20% |
| R24/105gD | 61 | n.d. | n.d | n.d. | <1 |
| R24/128gD | 60 | ++ | ++ | perinuclear | 20% |
| R24/139gD | 59 | ++ | + | perinuclear | <1 |
| R24/164gD† | 56 | ++ | n.d. | perinuclear | <1 |
| R24/179gD | 55 | ++ | + | perinuclear | 3 |
| R24/191gD | 54 | ++ | + | perinuclear | <1 |
| R24/207gD | 52 | ++ | + | perinuclear | <1 |
| R24/231gD† | 49 | ++ | n.d. | perinuclear | <1 |
| R24/239gD | 48 | ++ | + | perinuclear | <1 |

TABLE 2-continued

Table 2 shows expression and CHO cell infection data from R24 scFv linked to 15 N-terminal deletions of HSV-1 gD.

| Construct | Approx Mr (KDa) * | Vero cell expression ** | Virus incorp ** | Localization in Vero cells | CHO cell infectivity *** |
|---|---|---|---|---|---|
| R24/260gD† | 45 | +++ | ++ | perinuclear | 60% |
| R24/274gD† | 43 | ++ | ++ | perinuclear | 50% |

* Fusion protein Mr = scFv (30 kDa) + gD amino acids,
** Band intensity from Western blots; high = +++, intermediate = ++, low = +, n.d. = not detected,
† indicates fusion protein shown in FIG. 1b,
*** Percentage of CHO cells infected

TABLE 3

Table 3 shows infection of THP-1 cells by HSV1716 variants that display scFv either against CD20 or CD38 glycoprotein fusion proteins.

| Protein/virus | Localization in Vero cells*** | THP-1 infectivity | THP-1 infectivity + MabT | THP-1 infectivity + Mab5 |
|---|---|---|---|---|
| 5/37gD | perinuclear | 10% | 10% | 10% |
| 5/128gD | perinuclear | 15% | 10% | 10% |
| 5/260gD | perinuclear | 15% | 15% | 15% |
| 5/274gD | perinuclear | 10% | 10% | 15% |
| T/37gD | perinuclear | 30% | 10% | 40% |
| T/128gD | perinuclear | 20% | 15% | 15% |
| T/260gD | perinuclear | 60% | 20% | 50% |
| T/274gD | perinuclear | 40% | 10% | 30% |
| 5gH/gL2 | perinuclear | 10% | 10% | 10% |
| TgHgL2 | perinuclear | 30% | 15% | 30% |
| 1716V* | n/a | 5% | 10% | 10% |
| 1716B** | n/a | 20% | 30% | 20% |

*HSV1716 propagated on Vero cells,
**HSV1716 propagated on BHK cells,
***immunofluorescence on stably transformed cell lines with anti-myc (gC, gD, gL) or anti-HA (gH) monoclonal antibodies.

TABLE 4

Table 4 shows the ability of various HSV1716 variants with targeting moieties to infect a variety of different permissive, semi-permissive and non-permissive cell lines.

| Virus (1) | Titre (2) | BHK inf (3) | Vero inf (3) | CHO inf (4) | CHODAF inf (4) | THP-1 inf (5) | SupT inf (5) | TolB inf (5) |
|---|---|---|---|---|---|---|---|---|
| T/260gD | $1.8 \times 10^{10}$ pfu | 100 | 100 | 0 | 3 | 30 | 50 | 50 |
| T/274gD | $1.6 \times 10^{10}$ pfu | 100 | 100 | 1 | 5 | 50 | 50 | 70 |
| B/274gD | $6.6 \times 10^{9}$ pfu | 100 | 100 | 5 | 50 | 10 | 20 | 10 |
| 1716V (6) | $4.0 \times 10^{10}$ pfu | 100 | 100 | 0 | 0 | 10 | 10 | 30 |
| 17168 (7) | $9.8 \times 10^{9}$ pfu | 100 | 100 | 20 | 20 | 20 | 20 | 50 |

Notes on Table 4
(1) all HSV1716 variants with targeting moieties were propagated on Vero cells
(2) all viruses were titrated on BHK cells, and total yield from 4xT175 flasks is reported
(3) approximate percentage of cells infected as determined by fluorescence microscopy from a number of different experiments at 1 pfu/cell, BHK and Vero cells are fully permissive for HSV1716 infection.
(4) CHO and CHO/DAF cells are non-permisssive for HSV1716 infection when the virus is propagated on Vero cells but is semi-permissive when HSV1716 is propagated on BHK cells, CHO/DAF are CHO cells modified to constitutively express human CD55 (DAF)
(5) Cell lines which are semi-permissive for HSV1716 infection with the level of infectivity dependent on whether the cells are propagated on Vero or BHK cells. THP-1 is a human monocytic cell line which is CD38 positive and CD20 negative as determined by IF using MabT and Mab5. SupT is a human T-cell line which is CD38 positive and CD20 negative as determined by IF using MabT or Mab5, TolB is a human B-cell line which is positive for CD38 and weakly positive for CD20 as determined by IF using MabT or Mab5
(6) HSV1716 propagated on Vero cells is the control virus for the targeted variants
(7) HSV1716 propagated on BHK cells is better able to infect CHO, CHODAF, THP-1, SupT and TolB cells

TABLE 5

Table 5 shows effects of monoclonal antibodies on the abilities of targeted HSV1716 variants to infect SupT cells. Percentages of cells infected by the various viruses at 1 pfu/cell are reported

| Virus | Mab5 | MabT | Mab8 | MabB | Medium |
|---|---|---|---|---|---|
| 5/274gD | 10 | 20 | 10 | 10 | 5 |
| 5/274gDopp | 5 | 10 | 5 | 5 | 5 |
| T/274gD | 25 | 5 | 25 | 30 | 30 |
| B/274gD | 10 | 10 | 10 | 10 | 10 |
| 8/274gD | 10 | 10 | 10 | 10 | 10 |
| HSV1716V | 5 | 15 | 5 | 5 | 5 |
| HSV1716B | 10 | 20 | 10 | 10 | 10 |

TABLE 6

Table 6 shows effects of monoclonal antibodies on the abilities of targeted HSV1716 variants to infect THP-1 cells. Percentages of cells infected by the various viruses at 1 pfu/cell are reported

| Virus | Mab5 | MabT | Mab8 | MabB | Medium |
|---|---|---|---|---|---|
| 5/274gD | 20 | 20 | 20 | 10 | 20 |
| 5/274gDopp | 20 | 20 | 20 | 20 | 10 |
| T/274gD | 60 | 20 | 80 | 80 | 60 |
| B/274gD | 20 | 30 | 20 | 30 | 30 |
| 8/274gD | 10 | 20 | 20 | 10 | 20 |
| HSV1716V | 10 | 20 | 20 | 20 | 15 |
| HSV1716B | 15 | 30 | 25 | 10 | 30 |

TABLE 7

Table 7 shows effects of monoclonal antibodies on the abilities of targeted HSV1716 variants to infect TolB cells. Percentages of cells infected by the various viruses at 1 pfu/cell are reported

| Virus | Mab5 | MabT | Mab8 | MabB | Medium |
|---|---|---|---|---|---|
| 5/274gD | 20 | 20 | 20 | 20 | 20 |
| 5/274gDopp | 10 | 10 | 10 | 15 | 20 |
| T/274gD | 60 | 10 | 60 | 65 | 65 |
| B/274gD | 20 | 30 | 20 | 30 | 30 |
| 8/274gD | 30 | 20 | 20 | 20 | 30 |
| HSV1716V | 20 | 30 | 30 | 30 | 20 |
| HSV1716B | 40 | 30 | 40 | 30 | 30 |

REFERENCES

1 Aghi, M and Martuza, R L Oncolytic viral therapies—the clinical experience. *Oncogene* 2005; 24: 7802-7816.

2 Chiocca, E. A. (2002) Oncolytic Viruses. *Nature Reviews Cancer* 2002; 2: 938-950.

3 MacLean, A. R., Fareed, M U, Robertson, L., Harland, J. and Brown, S M Herpes simplex virus type 1 deletion variants 1714 and 1716 pinpoint neurovirulence related sequences in Glasgow strain 17+ between immediate early gene 1 and the "a" sequence. *J. Gen Virol* 1991; 72: 631-639.

4 Brown, S M, Harland, J., MacLean, A R, Podlech, J. and Clements, J B. (1994) Cell type and cell state determine differentiated in vitro growth of non-neuroviulent ICP34.5-negative herpes simplex virus. *J. Gen Virol.* 1994; 75: 2367-2377.

5 Brown, S. M., MacLean, A. R., McKie, E. A. and Harland, J. The herpes simplex virus virulence factor ICP34.5 and the cellular protein MyD116 complex with proliferating cell nuclear antigen through the 63-amino acid domain conserved in ICP34.5, MyD116 and GADD34. *J. Virol.* 1997; 71: 9442-9449.

6 Harland, J., Dunn, P., Cameron, E., Conner, J. and Brown, S. M. The herpes simplex virus (HSV) protein ICP34.5 is a virion component that forms a DNA-binding complex with proliferating cell nuclear antigen and HSV replication proteins. *J. Neurovirol.* 2003; 9: 477-488.

7 Rampling, R, Cruikshank, G, Papanastassiou, V, Nicoll, J, Hadley, D, Brennan, D, et al. Toxicity evaluation of replication-competent herpes simplex virus (ICP 34.5 null mutant 1716) in patients with recurrent malignant glioma. *Gene Therapy* 2000; 7:859-866.

8 Papanastassiou V, Rampling R, Fraser M, Petty R, Hadley D, Nicoll J, et al. The potential for efficacy of the modified (ICP 34.5(−)) herpes simplex virus HSV1716 following intratumoural injection into human malignant glioma: a proof of principle study. *Gene Therapy* 2002: 9: 398-406.

9 Harrow, S., Papanastassiou, V., Harland, J., Mabbs, R., Petty, R., Fraser, M. et al. HSV1716 injection into the brain adjacent to tumour following surgical resection of high-grade glioma: safety data and long term survival. *Gene Therapy* 2004; 11: 1648-1658.

10 MacKie, R M, Stewart, B and Brown, S M. Intralesional injection of herpes simplex virus 1716 in metastatic melanoma. *The Lancet* 2001; 357: 525-526.

11 McCormick, F. Future prospects for oncolytic therapy. *Oncogene* 2005; 24: 7817-7819.

12 Wickham, T. J. Ligand-directed targeting of genes to the site of disease. *Nature Medicine* 2003; 9: 135-139.

13 Galmiche, M. C., Rindisbacher, L., Wels, W., Wittek, R. and Buchegger, F. Expression of a functional single chain antibody on the surface of extracellular enveloped vaccinia virus as a step towards selective tumour cell targeting. *J. Gen. Virol.* 1997; 78: 3019-3027.

14 Chowdhury, S., Chester, K. A., Bridgewater, J., Collons, M. K. and Martin, F. Efficient retroviral vector targeting of cancinoembryonic antigen-positive tumours. *Molecular Therapy* 2004; 9: 85-92.

15 Khare, P. D., Shao-Xi, L., Kuroki, M., Hirose, Y., Arakawa, F., Nakamura, K et al. Specifically targeted killing of Cancinoembryonic Antigen (CEA)-expressing cells by a retroviral vector displaying single chain variable fragmented antibody to CEA and carrying the gene for inducible nitric oxide synthase. *Cancer Research* 2001; 61: 370-375.

16 Nguyen, T. H., Loux, N., Bagher, I., Vons, C., Carey, K., Briand, P. et al. Improved gene transfer selectivity to hepatocarcinoma cell by retrovirus vector displaying single-chain variable fragment antibody against c-Met. *Cancer Gene Therapy* 2003; 10: 840-849.

17 Marin, M., Noel, D., Valsesia-Mittman, S., Brockly, F., Etienne-Julan, M., Russell, S. et al. Targeted infection of human cells via major histocompatibility complex class 1 molecules by Moloney Murine Leukemia virus-derived viruses displaying single-chain antibody fragment-envelope fusion proteins. *J. Virol.* 1996; 70: 2957-2962.

18 Aires Da Silva, F., Costa, M. J. L., Corte-Real, S. And Goncalves, J. Cell type-specific targeting with Sindbis pseudotyped lentiviral vectors displaying anti-CCR5 single-chain antibodies. *Human Gene Therapy* 2005; 16: 223-234.

19 Martin, F., Neil, S., Kupsch, J., Maurice, M., Cosset, F-L. and Collins, M. Retrovirus targeting by tropism restriction to melanoma cells. *J. Virol.* 1999; 73: 6923-6929.

20 Bucheit, A. D., Kumar, S., Grote, D. M., Lin, Y., von Messling, V., Cattaneo, R. B. et al. An oncolytic measles virus engineered to enter cells through the CD20 antigen. *Molecular Therapy* 2003; 7: 62-72.

21 Peng, K-W., Donovan, K. A., Schneider, U., Cattaneo, R., Lust, J. A. and Russell, S. J. Oncolytic measles viruses displaying a single chain antibody against CD38, a myeloma cell marker. *Blood* 2003; 101: 2557-2562.

22 Watkins, S. J., Mesyanzhinov, V. V., Kurochkina, L. P. and Hawkins, R. E. The 'adenobody' approach to viral targeting: specific and enhanced adenoviral gene delivery. *Gene Therapy* 1997; 4: 1004-1012.

23 Haisma, H. J., Grill, J., Curiel, D. T., Hoogeland, S., van Beusechem, V. W., Pinedo, H. M. and Gerritsen, W. R. (2000) Targeting of adenoviral vectors through a bispecific single chain antibody. *Cancer Gene Therapy* 2000; 7: 901-904.

24 Nettelbeck, D. M., Miller, D. W., Jerome, V., Zuzarte, M., Watkins, S. J., Hawkins, R. E. et al. Targeting of adenovirus 24. to endothelial cells by a bispecific single-chain diabody directed against the adenovirus fiber knob domain and human endoglin (CD105). *Molecular Therapy* 2001; 3: 882-891.
25. Pereboev, A. V., Asiedu, C. K., Kawakami, Y., Dong, S. S., Blackwell, J. L., Kashentseva, E. A. et al. Coxsackievirus-adenovirus receptor genetically fused to anti-human CD40 scFv enhances adenoviral transduction of dendritic cells. *Gene Therapy* 2002; 9: 1189-1193.
26. van Beusechem, V. W., Mastenbroek, D. C. J., van den Doel, P. B., Lamfers, M. L. M., Grill, J., Wurdinger, T. et al. Conditionally replicative adenovirus expressing a targeting adapter molecule exhibits enhanced oncolytic potency on CAR-deficient tumors. *Gene Therapy* 2003; 10: 1982-1991.
27. Nettelbeck, D. M., Rivera, A. A., Kupsch, J., Dieckmann, D., Douglas, J. T., Kontermann, R. E. et al. Retargeting of adenovirus infection to melanoma: combining genetic ablation of native tropism with a recombinant bispecific single-chain diabody (scDb) adapter that binds to Fiber knob and HMWMAA. *Int. J. Cancer* 2004; 108: 136-145.
28. Breidenbach, M., Rein, D. T., Everts, M., Glasgow, J. N., Wang, M., Passineau, M. J. et al. Mesothelin-mediated targeting of adenoviral vectors for ovarian cancer gene therapy. *Gene Therapy* 2005; 12: 187-193.
29. Laquerre, S., Anderson, D. B., Stolz, D. B. and Glorioso, J. C. (1998) Recombinant herpes simplex virus type 1 engineered for targeted binding to erythropoietin receptor-bearing cells. *J. Virol.* 1998; 72: 9683-9697.
30. Zhou, G., Ye, G-J., Debinski, W. and Roizman, B. (2002) Engineered herpes simplex virus type 1 is dependent on IL13Rα2 receptor for cell entry and independent of glycoprotein D receptor interaction. *PNAS* 2002; 99: 15124-15129.
31. Zhou, G. and Roizman, B. Characterization of a recombinant herpes simplex virus type 1 designed to enter cells via the IL13Rα2 receptor of malignant glioma cells. *J. Virol.* 2005; 79: 5272-5277.
32. Argnani, R., Boccafogli, L., Marconi, P. C. and Manservigi, R. Specific targeted binding of herpes simplex type 1 to hepatocytes via the human hepatitis B virus preS1 peptide. *Gene Therapy* 2004; 11: 1087-1098.
33. Kamiyama, H., Zhou, G. and Roizman, B. (2005) Herpes simplex virus 1 recombinant virions exhibiting the amino terminal fragment of urokinase-type plasminogen activator can enter cells via the cognate receptor. *Gene Therapy* 2005; 12: 1-9
34. Grandi, P., Wang, S., Schuback, D., Krasnykh, V., Spear, M., Curiel, D. T. et al. HSV-1 virions engineered for specific binding to cell surface receptors. *Molecular Therapy* 2004; 9: 419-427.
35. Nakano, K., Asano, R., Tsumoto, K., Kwon, H., Goins, W. F., Kumagai, I. et al. Herpes simplex virus targeting to the EGF receptor by a gD-specific soluble bridging molecule. *Molecular Therapy* 2005; 11: 617-626.
36. Menotti, L., Cerretani, A. and Campadelli-Fiume, G. A herpes simplex virus recombinant that exhibits a single chain antibody to HER2/neu enters cells through the mammary tumor receptor, independently of the gD receptors. *J. Virol.* 2006; 80: 5531-5539.
37. Spear, P. G. and Longnecker R. Herpesvirus entry: an update. *J. Virol.* 2003; 77:10179-10185.
38. Spear, P. G. Herpes simplex virus: receptors and ligands for cell entry. *Cell Microbiol.* 2004; 6: 401-410.
39. Cocchi, F., Menotti, L., Mirandola, P., Lopez, M. and Campadelli-Fiume, G. The ectodomain of a novel member of the immunoglobulin subfamily related to the poliovirus receptor has the attributes of a bona fide receptor for herpes simplex virus types 1 and 2 in human cells. *J. Virol.* 1998; 72: 9992-10000.
40. Haarr, L., Shukla, D., Rodahl, E., Dal Canto, M. C. and Spear, P. G. Transcription from the gene encoding the herpesvirus entry receptor nectin 1 (HveC) in nervous tissue of adult mouse. *Virology* 2001; 287: 301-309.
41. Mata, M., Zhang, M., Hu, X. and Fink, D. J. HveC (nectin-1) is expressed at high levels in sensory neurons, but not in motor neurons, of the rat peripheral nervous system. *J. Neurovirol.* 2001; 7: 476-480.
42. Richart, S. M., Simpson, S. A., Krummenacher, C., Whitbeck, J. C., Pizer, L. I., Cohen, G. H. et al. Entry of herpes simplex virus type 1 into primary sensory neurons in vitro is mediated by nectin-1/HveC. *J. Virol.* 2003; 77: 3307-3311.
43. Montgomery, R. I., Warner, M. S., Lum B. J. and Spear, P. G. 1996. Herpes simplex virus-1 entry into cells mediated by a novel member of the TNF/NGF receptor family. *Cell* 1996; 87: 427-436.
44. Peng, T., Ponce De Leon, M., Novotny, M. J., Jiang, H., Lambris, J. D., Dubin, G. et al. Structural and antigenic analysis of a truncated form of the herpes simplex virus glycoprotein gH-gL complex. *J. Virol.* 1998; 72: 6092-6103.
45. Conner, J., Rixon, F. J. and Brown, S. M. Herpes simplex virus type 1 strain HSV1716 grown in baby hamster kidney cells has altered tropism for nonpermissive Chinese hamster ovary cells compared to HSV1716 grown in Vero cells. *J. Virol.* 2005; 79: 9970-9981.
46. Nicola, A. V. A. M. McEvoy and S. E. Straus. Roles for endocytosis and low pH in herpes simplex virus entry into HeLa and Chinese hamster ovary cells. *J. Virol.* 2003; 77: 5324-5332.
47. Nicola, A. V. and Strauss, S. E. (2004) Cellular and viral requirements for rapid entry of herpes simplex virus. *J. Virol.* 2004; 78: 7508-7517.
48. Carfi, A., Willis, S. H., Whitbeck, J. C., Krummenacher, C., Cohen, G. H., Eisenberg, R. J. and Wiley, D. C. Herpes simplex virus glycoprotein D bound to the human receptor HveA. *Mol. Cell.* 2001; 8: 169-179.
49. Whitbeck, J. C., Muggeridge, M. I., Rux, A. H., Hou, W., Krummenacher, C., Lou, H. et al. The major neutralizing antigenic site on herpes simplex virus glycoprotein D overlaps a receptor binding domain. *J. Virol.* 1999; 73: 9879-9890.
50. Zhou, G., Avitabile, E., Campadelli-Fiume, G. and Roizman, B. The domains of glycoprotein D required to block apoptosis induced by herpes simplex virus 1 are largely distinct from those involved in cell-cell fusion and binding to nectin 1. *J. Virol.* 2003; 77: 3759-3767.
51. Milne, R. S., Hanna, S. L., Rux, A. H., Willis, S. H., Cohen, G. H. and Eisenberg, R. J. Function of herpes simplex virus type 1 gD mutants with different receptor binding affinities in virus entry and fusion. *J. Virol.* 2003; 77: 8962-8972.
52. Cocchi, F., Fusco, D., Menotti, L., Gianni, T., Eisenberg, R. J., Cohen, G. H. et al The soluble ectodomain of herpes simplex virus gD contains a membrane-proximal pro-fusion domain and suffices to mediate virus entry. *PNAS* 2004; 101: 7445-7450.
53. Pope, A. R., Embleton, M. J. and Mernaugh, R. (1996) Construction and use of antibody gene reportoires. In Antibody Engineering A Practical Approach, (eds J. McCafferty, H. R. Hoogenboom and D. J. Chiswell) IRL Press, Oxford. Pp 1-40.
54. Conner, J., J. Furlong, J. Murray, M. Meighan, A. Cross, H. Marsden et al. Herpes simplex virus type 1 ribonucleotide reductase large subunit: regions of the protein essential for subunit interaction and dimerization. *Biochemistry* 1993; 32:13,673-13,680.
55. PCT/GB2003/000603; WO 03/068809.
56. WO 2005/005637

57 Zhou, G., Roizman, B. Separation of receptor-binding and profusogenic domains of glycoprotein D of herpes simplex virus 1 into distinct interacting proteins. *PNAS* 2007; 104: 10 4142-4146.

58 Connolly, S. A. et al., Structure-Based Mutagenesis of Herpes Simlex virus Glycoprotein D defines three critical regions at the gD-HveA/HVEM Binding interface. J. Virol. 2003, 77:14 8127-8140

The invention claimed is:

1. A herpes simplex virus (HSV) comprising an N-terminally truncated glycoprotein D linked to a targeting agent, wherein the N-terminally truncated glycoprotein D has a truncation of at least up to position 260 of the full-length HSV-1 glycoprotein D, wherein the truncation is no greater than or equal to position 274 of the full-length HSV-1 glycoprotein D.

2. A HSV according to claim 1, wherein the N-terminally truncated glycoprotein D has an extracellular domain comprising at least 42 amino acids.

3. A HSV according to claim 1, wherein the N-terminally truncated glycoprotein D has an extracellular domain comprising a portion of amino acids corresponding to amino acids 274-315 of the full-length HSV-1 glycoprotein D.

4. A HSV according to claim 1, wherein targeting agent and the N-terminally truncated glycoprotein D are a fusion protein.

5. A HSV according to claim 1, wherein the targeting agent is an antibody binding domain.

6. A HSV according to claim 1, wherein the targeting agent and N-terminally truncated HSV-1 glycoprotein D are a fusion protein, and wherein the targeting agent is an antibody binding domain.

7. A HSV according to claim 1, wherein the N-terminally truncated glycoprotein D is an N-terminal truncate of a glycoprotein D having the amino acid sequence of SEQ ID NO: 1.

8. A HSV according to claim 1, wherein the targeting agent is specific for a target selected from the group consisting of GD3, CD38, CD55, CD20, EGRF, HER2/neu, CEA, squamous cell carcinoma antigens 1 and 2, ovarian carcinoma antigen CA125, Mucin 1, prostate-specific membrane antigen, melanoma-associated tumour antigen p97, 5T4 oncofoetal trophoblast glycoprotein, CA19-9, CA72-4 and CA195.

9. A HSV according to claim 1, wherein the HSV is a mutant of HSV-1.

10. A HSV according to claim 1, wherein the HSV is non-neurovirulent.

11. A HSV according to claim 1, wherein the HSV does not comprise an ICP34.5 gene that encodes a functional ICP34.5 gene product.

12. A HSV according to claim 1, wherein the HSV is a mutant of HSV1716.

* * * * *